US010792160B2

(12) United States Patent  
Katrana et al.

(10) Patent No.: US 10,792,160 B2  
(45) Date of Patent: Oct. 6, 2020

(54) ELBOW PROSTHESIS

(71) Applicant: Encore Medical, LP, Austin, TX (US)

(72) Inventors: Nicholas J. Katrana, Fort Wayne, IN (US); Brian K. Berelsman, Warsaw, IN (US); Nathan A. Winslow, Warsaw, IN (US)

(73) Assignee: Encore Medical, L.P., Austin, TX (US)

( * ) Notice: Subject to any disclaimer, the term of this patent is extended or adjusted under 35 U.S.C. 154(b) by 102 days.

(21) Appl. No.: 16/235,457

(22) Filed: Dec. 28, 2018

(65) Prior Publication Data

US 2019/0231541 A1   Aug. 1, 2019

Related U.S. Application Data

(60) Continuation of application No. 14/221,383, filed on Mar. 21, 2014, now Pat. No. 10,226,346, which is a (Continued)

(51) Int. Cl.
*A61F 2/38* (2006.01)
*A61F 2/30* (2006.01)

(52) U.S. Cl.
CPC .............. *A61F 2/38* (2013.01); *A61F 2/3094* (2013.01); *A61F 2/3804* (2013.01); (Continued)

(58) Field of Classification Search
CPC .. A61F 2/38; A61F 2/3804; A61F 2002/3809; A61F 2002/3813; (Continued)

(56) References Cited

U.S. PATENT DOCUMENTS 3,547,115 A   12/1970   Stevens  
3,694,821 A   10/1972   Moritz  
(Continued)

FOREIGN PATENT DOCUMENTS

DE   2806717   2/1978  
DE   3417923   11/1985  
(Continued)

OTHER PUBLICATIONS

Biomet Orthopedics, Inc., 1995, AGC Total Knee System (product brochure) 11 pp.
(Continued)

*Primary Examiner* — Suba Ganesan  
(74) *Attorney, Agent, or Firm* — Knobbe Martens Olson & Bear LLP

(57) ABSTRACT

A joint prosthesis is provided and may include first and second stem structures and first and second bearing members. The first stem structure may include a generally U-shaped portion having first and second legs. The second stem structure may include first and second bearing surfaces. The first bearing member may be removably coupled to the first leg and may include a first laterally facing bearing surface rotatably contacting the first bearing surface. The second bearing member may be removably coupled to the second leg and may include a second laterally facing bearing surface rotatably contacting the second bearing surface. The first laterally facing bearing surface may be disposed between the first leg and a first lateral side of the second stem. The second laterally facing bearing surface may be disposed between the second leg and a second lateral side of the second stem. The second lateral side may oppose the first lateral side.

18 Claims, 57 Drawing Sheets

Related U.S. Application Data division of application No. 12/780,424, filed on May 14, 2010, now Pat. No. 8,932,362, which is a continuation-in-part of application No. 12/562,616, filed on Sep. 18, 2009, now Pat. No. 9,561,110, which is a continuation-in-part of application No. 12/391,904, filed on Feb. 24, 2009, now Pat. No. 10,231,839, which is a continuation-in-part of application No. 11/384,943, filed on Mar. 17, 2006, now Pat. No. 8,585,768, which is a continuation of application No. 10/333,140, filed as application No. PCT/US01/22338 on Jul. 17, 2001, now Pat. No. 7,247,170.

(60) Provisional application No. 60/219,103, filed on Jul. 18, 2000.

(52) U.S. Cl.
CPC ........... *A61F 2002/30339* (2013.01); *A61F 2002/30367* (2013.01); *A61F 2002/30604* (2013.01); *A61F 2002/3809* (2013.01); *A61F 2002/3813* (2013.01); *A61F 2220/0033* (2013.01); *Y10T 29/49826* (2015.01)

(58) Field of Classification Search
CPC ...... A61F 2002/3818; A61F 2002/3822; A61F 2002/3827; A61F 2002/3831; A61F 2/42; A61F 2/4261
See application file for complete search history.

(56) References Cited

U.S. PATENT DOCUMENTS

| | | |
|---|---|---|
| 3,708,805 A | 1/1973 | Scales et al. |
| 3,816,854 A | 6/1974 | Schlein |
| 3,824,630 A | 7/1974 | Johnston |
| 3,852,831 A | 12/1974 | Dee |
| 3,919,725 A | 11/1975 | Swanson et al. |
| 3,939,496 A | 2/1976 | Ling et al. |
| 3,946,445 A | 3/1976 | Bentley et al. |
| 3,990,117 A | 11/1976 | Pritchard et al. |
| 3,991,425 A | 11/1976 | Martin et al. |
| 4,001,603 A | 1/1977 | Wilcox |
| 4,008,495 A | 2/1977 | Cavendish et al. |
| 4,038,704 A | 8/1977 | Ring |
| 4,079,469 A | 3/1978 | Wadsworth |
| 4,129,902 A | 12/1978 | Harmon |
| 4,131,956 A | 1/1979 | Treace |
| 4,131,957 A | 1/1979 | Bokros |
| 4,194,250 A | 3/1980 | Walker |
| 4,206,516 A | 6/1980 | Pilliar |
| 4,224,695 A | 9/1980 | Grundei et al. |
| 4,224,697 A | 9/1980 | Murray et al. |
| 4,242,758 A | 1/1981 | Amis et al. |
| 4,259,752 A | 4/1981 | Taleisnik |
| 4,280,231 A | 7/1981 | Swanson |
| 4,293,963 A | 10/1981 | Gold et al. |
| 4,301,552 A | 11/1981 | London |
| 4,352,212 A | 10/1982 | Greene et al. |
| 4,378,607 A | 4/1983 | Wadsworth |
| 4,383,337 A | 5/1983 | Volz et al. |
| 4,479,271 A | 10/1984 | Bolesky et al. |
| 4,538,306 A | 9/1985 | Dorre et al. |
| 4,659,331 A | 4/1987 | Matthews et al. |
| 4,725,280 A | 2/1988 | Laure |
| 4,759,768 A | 7/1988 | Hermann et al. |
| 4,790,854 A | 12/1988 | Harder et al. |
| 4,822,364 A | 4/1989 | Inglis et al. |
| 4,911,719 A | 3/1990 | Merle |
| 4,927,422 A | 5/1990 | Engelhardt |
| 4,936,853 A | 6/1990 | Fabian et al. |
| 5,024,670 A | 6/1991 | Smith et al. |
| 5,030,237 A | 7/1991 | Sorbie et al. |
| 5,108,442 A | 4/1992 | Smith et al. |
| 5,207,711 A | 5/1993 | Caspari et al. |
| 5,282,867 A | 2/1994 | Mikhail |
| 5,314,484 A | 5/1994 | Huene |
| 5,376,121 A | 12/1994 | Huene et al. |
| 5,380,334 A | 1/1995 | Torrie et al. |
| 5,411,555 A | 5/1995 | Nieder |
| 5,458,644 A | 10/1995 | Grundel |
| 5,507,821 A | 4/1996 | Sennwald et al. |
| 5,507,826 A | 4/1996 | Besselink et al. |
| 5,549,685 A | 8/1996 | Hayes |
| 5,584,835 A | 12/1996 | Greenfield |
| 5,665,087 A | 9/1997 | Huebner |
| 5,702,471 A | 12/1997 | Grundei et al. |
| 5,725,541 A | 3/1998 | Anspach, III et al. |
| 5,725,591 A | 3/1998 | DeCarlo, Jr. et al. |
| 5,782,923 A | 7/1998 | Engelbrecht et al. |
| 5,840,078 A | 11/1998 | Yerys |
| 5,879,395 A | 3/1999 | Tornier et al. |
| 5,928,285 A | 7/1999 | Bigliani et al. |
| 5,980,557 A | 11/1999 | Iserin et al. |
| 6,027,534 A | 2/2000 | Wack et al. |
| 6,120,543 A | 9/2000 | Kubein-Meesenburg et al. |
| 6,162,253 A | 12/2000 | Conzemius et al. |
| 6,290,725 B1 | 9/2001 | Weiss et al. |
| 6,306,171 B1 | 10/2001 | Conzemius |
| 6,379,387 B1 | 4/2002 | Tornier |
| 6,500,208 B1 | 12/2002 | Metzger et al. |
| 6,626,906 B1 | 9/2003 | Young |
| 6,656,225 B2 | 12/2003 | Martin |
| RE38,409 E | 1/2004 | Noiles |
| 6,699,290 B1 | 3/2004 | Wack et al. |
| 6,716,248 B2 | 4/2004 | Huene |
| 6,767,368 B2 | 7/2004 | Tornier et al. |
| 6,814,757 B2 | 11/2004 | Kopylov et al. |
| 6,890,357 B2 | 5/2005 | Tornier |
| 7,247,170 B2 | 7/2007 | Graham et al. |
| 7,527,650 B2 | 5/2009 | Johnson et al. |
| 7,604,666 B2 | 10/2009 | Berelsman et al. |
| 7,625,406 B2 | 12/2009 | Berelsman et al. |
| 8,585,768 B2 | 11/2013 | Berelsman et al. |
| 8,932,362 B2 | 1/2015 | Katrana et al. |
| 8,998,995 B2 | 4/2015 | Katrana et al. |
| 9,034,050 B2 | 5/2015 | Katrana et al. |
| 9,561,110 B2 | 2/2017 | Graham et al. |
| 9,901,453 B2 | 2/2018 | Katrana et al. |
| 10,149,766 B2 | 12/2018 | Katrana et al. |
| 2002/0055783 A1 | 5/2002 | Tallarida et al. |
| 2002/0165614 A1 | 11/2002 | Tornier |
| 2003/0208277 A1* | 11/2003 | Weiss .................. A61F 2/3804 623/20.12 |
| 2004/0186580 A1 | 9/2004 | Steinmann |
| 2004/0243243 A1 | 12/2004 | Tornier |
| 2004/0254574 A1 | 12/2004 | Morrison et al. |
| 2005/0049710 A1 | 3/2005 | O'Driscoll et al. |
| 2005/0216090 A1 | 9/2005 | O'Driscoll et al. |
| 2006/0224243 A1 | 10/2006 | Pare |
| 2006/0247786 A1 | 11/2006 | Ball |
| 2008/0154384 A1 | 6/2008 | Acker et al. |
| 2008/0183291 A1 | 7/2008 | Scheller et al. |
| 2008/0188942 A1 | 8/2008 | Brown et al. |
| 2009/0105839 A1 | 4/2009 | Ikegami et al. |
| 2010/0179661 A1 | 7/2010 | Berelsman et al. |
| 2010/0305710 A1 | 12/2010 | Metzger et al. |
| 2012/0136450 A1 | 5/2012 | Wendelburg et al. |
| 2013/0345818 A1 | 12/2013 | Wagner et al. |
| 2014/0324175 A1 | 10/2014 | Katrana et al. |
| 2017/0239057 A1 | 8/2017 | Katrana et al. |
| 2017/0367832 A1 | 12/2017 | Katrana et al. |

FOREIGN PATENT DOCUMENTS

| | | |
|---|---|---|
| DE | 3940728 | 6/1991 |
| EP | 1 051 954 | 11/2000 |
| EP | 1 481 653 | 12/2004 |
| FR | 2419718 | 10/1979 |
| FR | 2634373 | 1/1990 |
| GB | 1 520 162 | 8/1978 |
| SU | 1560-183 | 4/1990 |

(56) References Cited

FOREIGN PATENT DOCUMENTS

| SU | 1567-200 | 5/1990 |
|----|----------|--------|
| WO | WO 00/23012 | 4/2000 |
| WO | WO 13/006536 | 1/2013 |

OTHER PUBLICATIONS

DePuy Orthopaedics, Inc., 2000, Elbow Replacement Surgery, http://www.allaboutarthritis.com/AllAboutArthritis/layoutTemplates/html/en/contentdisplay/document/condition/arthritis/clinicalArticle/Elbow.s- ub.--Replacement.sub.--Surgery.htm, 3 pp.
Biomet Orthopedics, Inc., 2002, Discovery Elbow System Surgical Technique (product brochure), 20 pp.
DePuy Orthopaedics, Inc., 2000, Acclaim Total Elbow Replacement System: Overview, www.jointreplacement.com/xq/ASP.default/mn.local/pg.list/joint_id.2/list_id.59/newFont.2/joint_nm.Elbow/local_id.18/qx/default.htm, 3 pp.
DePuy Orthopaedics, Inc., 2000, Acclaim Total Elbow Replacement System: Surgery, www.jointreplacement.com/xq/ASP.default/mn.local/pg.list/joint_id.2/list_id.59/newFont.2/joint_nm.Elbow/local_id.18/qx/default.htm, 3 pp.
Tornier, Latitude®, Total Elbow Prosthesis: A New Generation Is Born Naturally Precise (product brochure), 4 pp. undated.
Tornier, Latitude® Total Elbow Prosthesis: Surgical Technique (product brochure), 40 pp., undated.
Wright Medical Technology, Inc., 2003, Extremities: Sorbie-Questor® Total Elbow System (product brochure), 1 p.
International Search Report for PCT/US01/22338 dated Jan. 3, 2002.
Non-final Office Action dated Apr. 13, 2010 in U.S. Appl. No. 11/384,943.
Final Office Action dated Oct. 27, 2010 in U.S. Appl. No. 11/384,943.
Non-final Office Action dated Apr. 12, 2011 in U.S. Appl. No. 11/384,943.
Final Office Action dated Dec. 12, 2011 in U.S. Appl. No. 11/384,943.
Office Action dated Nov. 1, 2012 in U.S. Appl. No. 12/391,904.
Office Action dated Mar. 27, 2015 in U.S. Appl. No. 12/391,904.
Non-Final Office Action regarding U.S. Appl. No. 12/562,616, dated May 17, 2012.
Office Action dated Apr. 9, 2014 in U.S. Appl. No. 12/562,616.
Office Action dated Dec. 29, 2014 in U.S. Appl. No. 12/562,616.
Office Action dated Jun. 26, 2015 in U.S. Appl. No. 12/562,616.
Non-Final Office Action regarding U.S. Appl. No. 12/780,424, dated Nov. 2, 2012.
Office Action dated Jun. 19, 2013 in U.S. Appl. No. 13/051,559.
Office Action dated Apr. 23, 2014 in U.S. Appl. No. 13/051,559.
Office Action dated Feb. 7, 2014 in U.S. Appl. No. 13/465,690.
Office Action dated Aug. 18, 2014 in U.S. Appl. No. 13/465,690.
International Search Report and Written Opinion for PCT/US2010/049314 dated Feb. 21, 2011.
International Search Report and Written Opinion for PCT/US2009/057449 dated Feb. 21, 2011.
International Preliminary Report on Patentability and Written Opinion for PCT/US2009/057449 dated Sep. 9, 2011.
International Search Report and Written Opinion of the International Searching Authority regarding International Application No. PCT/US2014/021970, dated May 12, 2014.
International Search Report and Written Opinion dated Nov. 8, 2012 in PCT/US12/045207.

\* cited by examiner

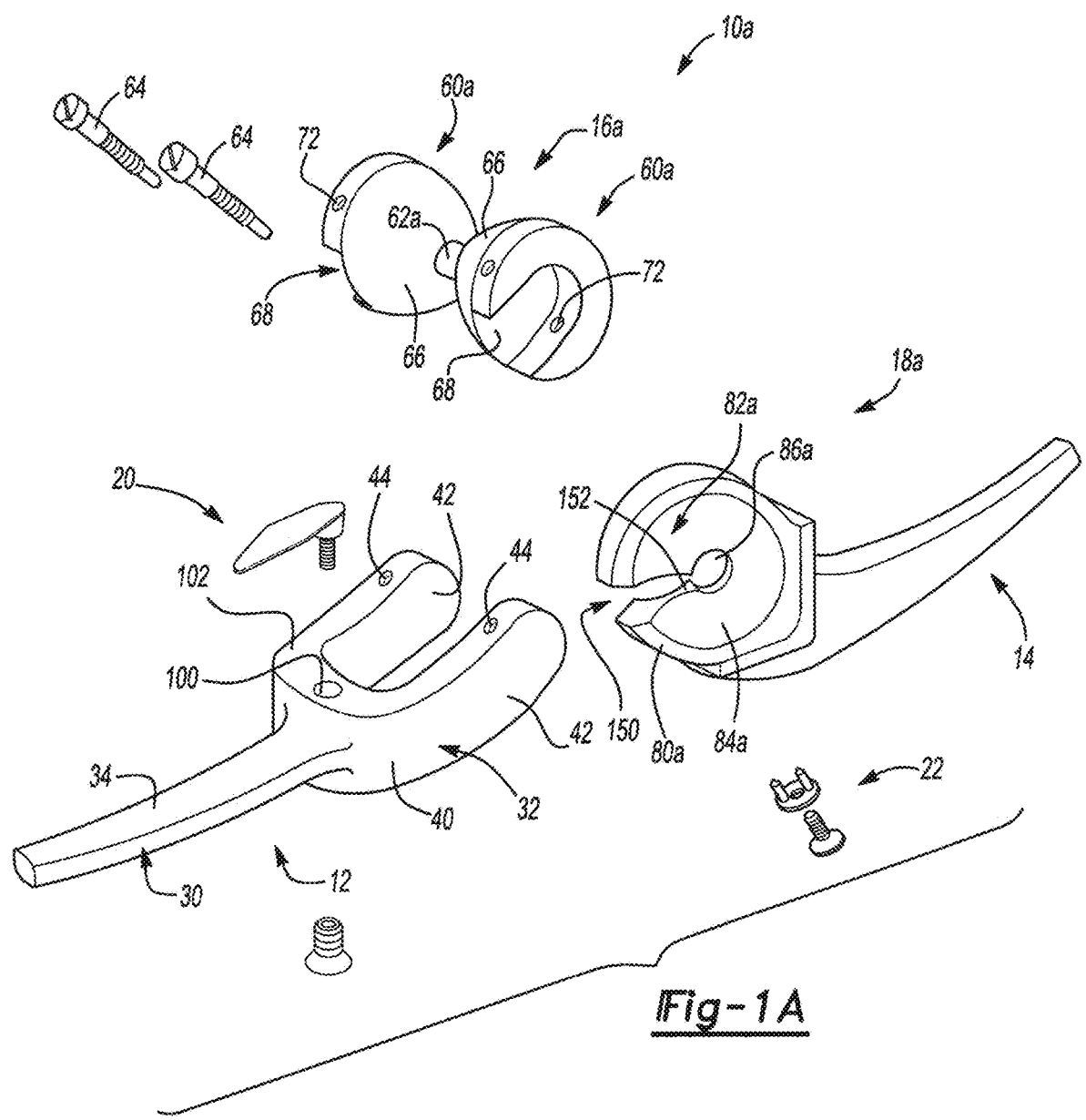

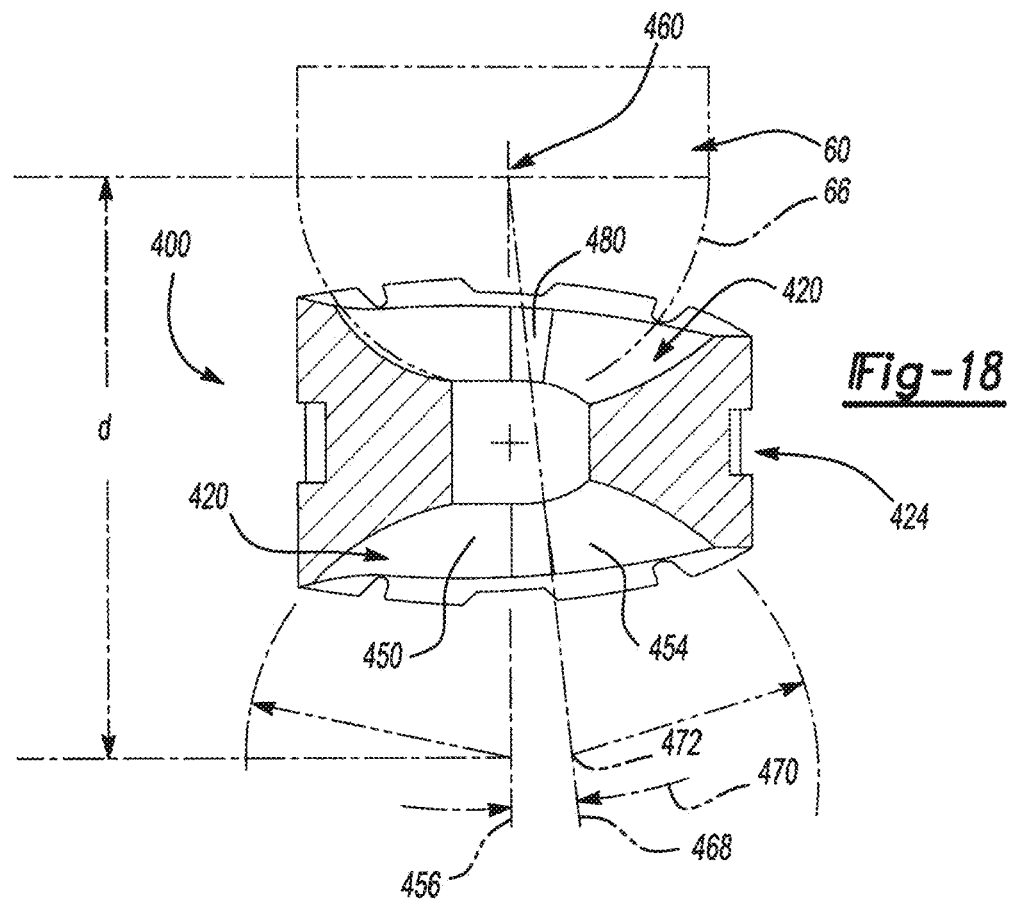
*Fig-18*
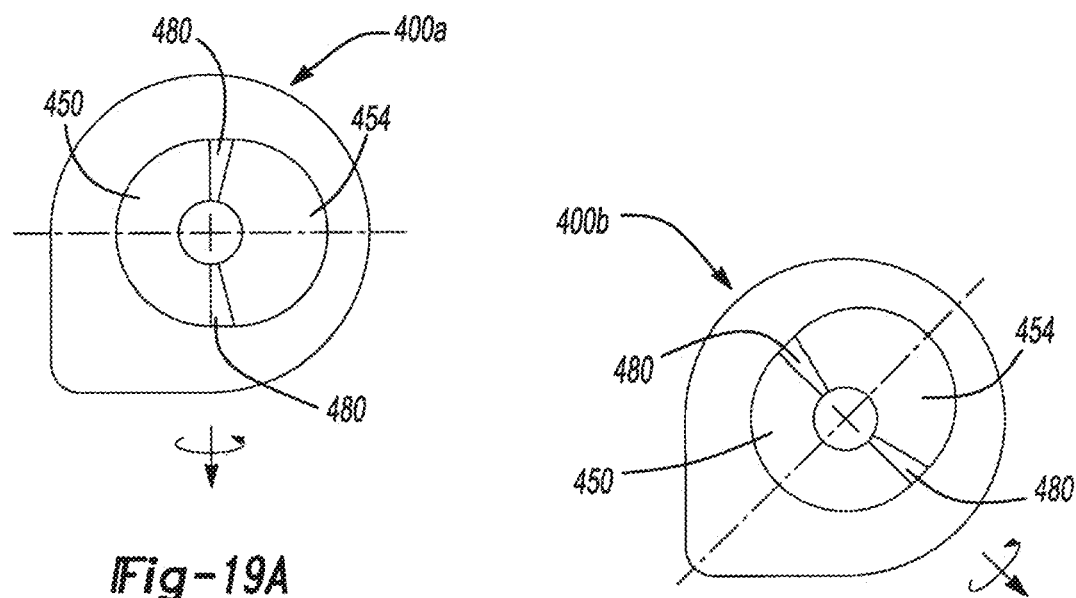
*Fig-19A*
*Fig-19B*

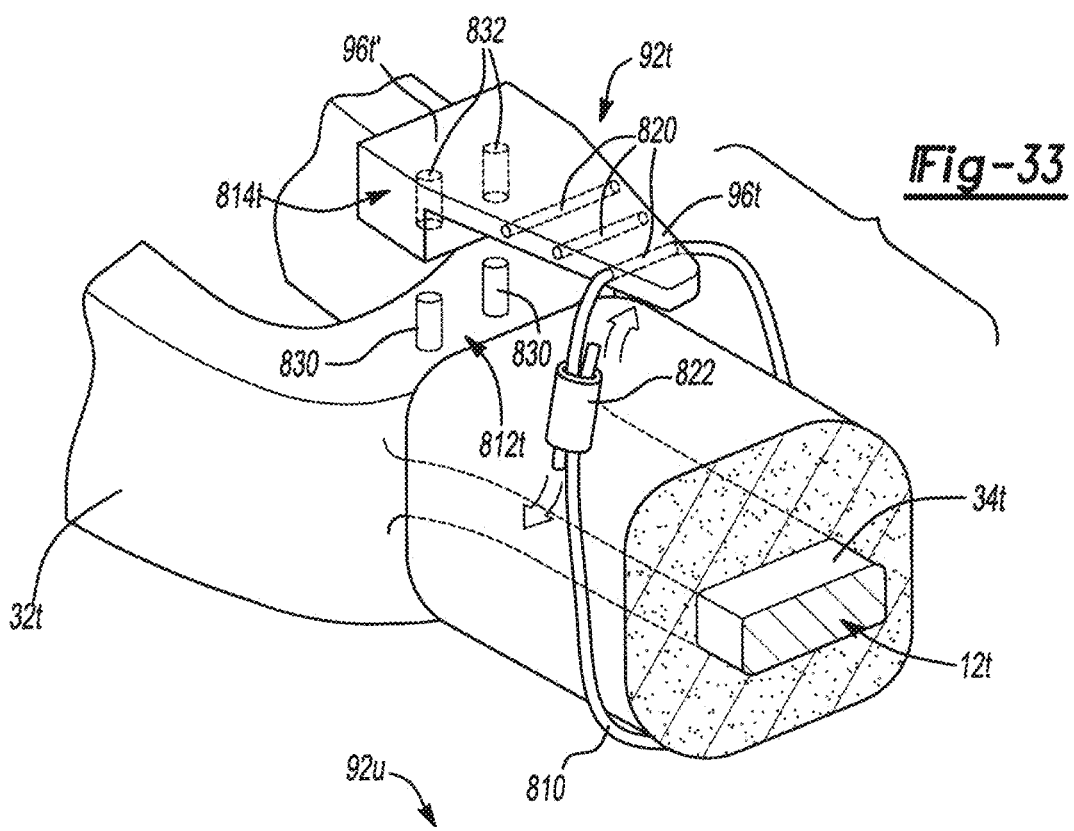
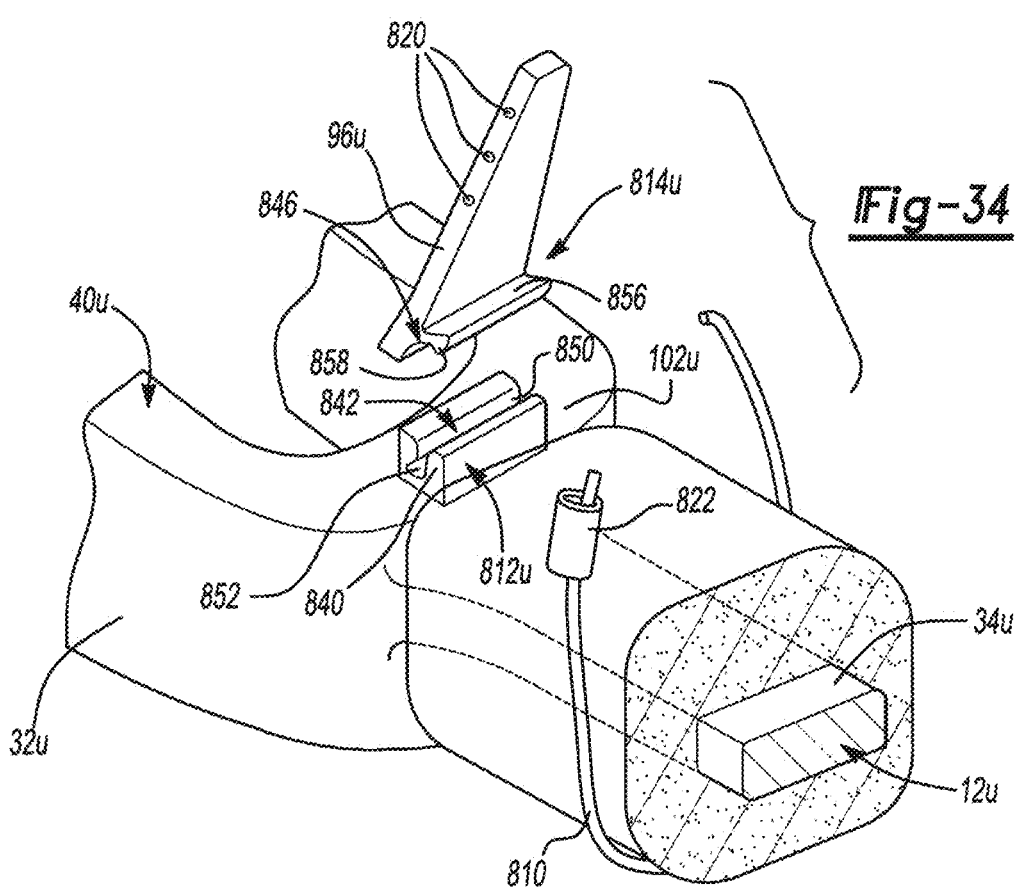

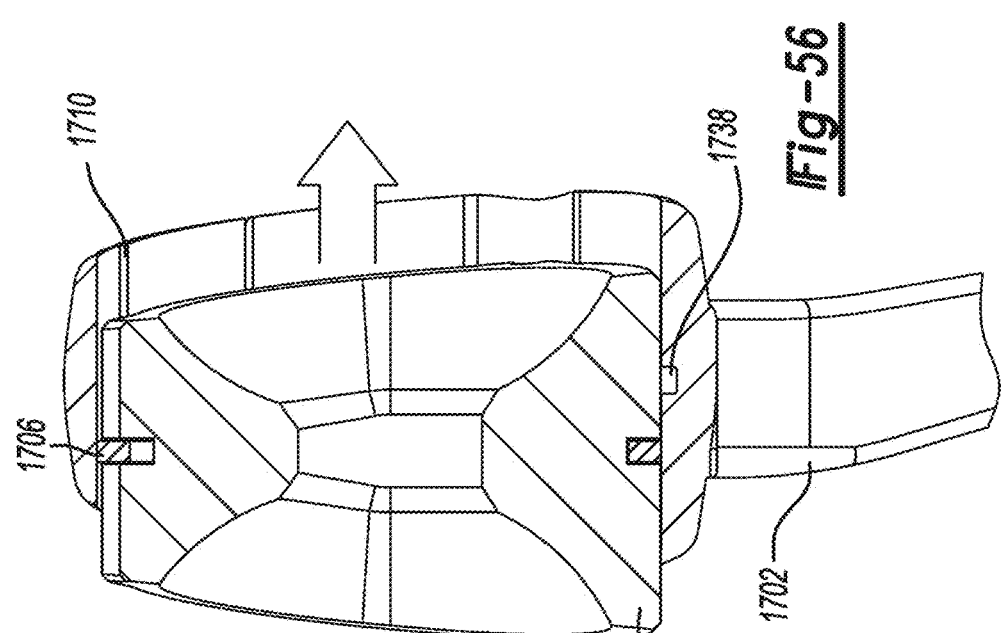
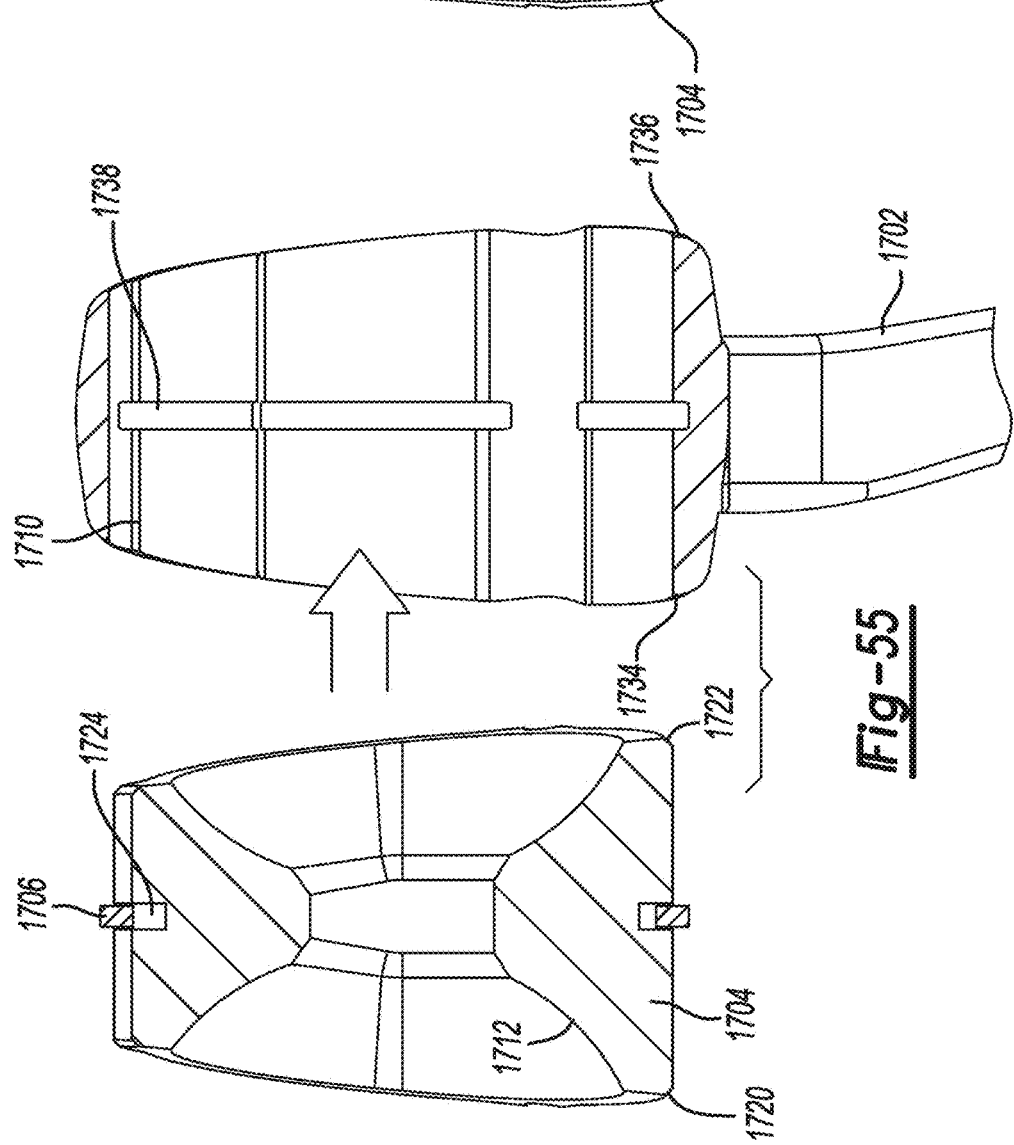

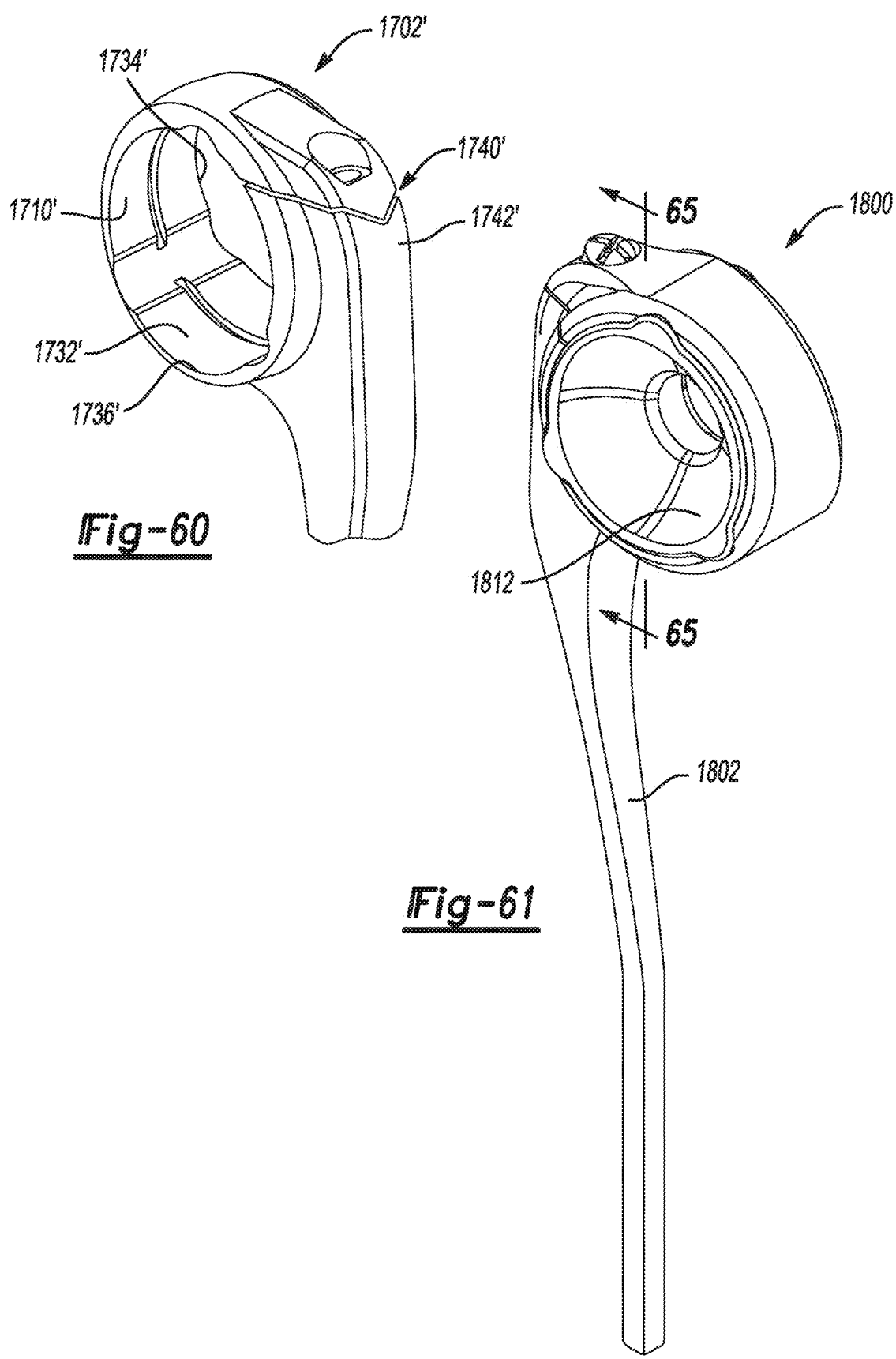

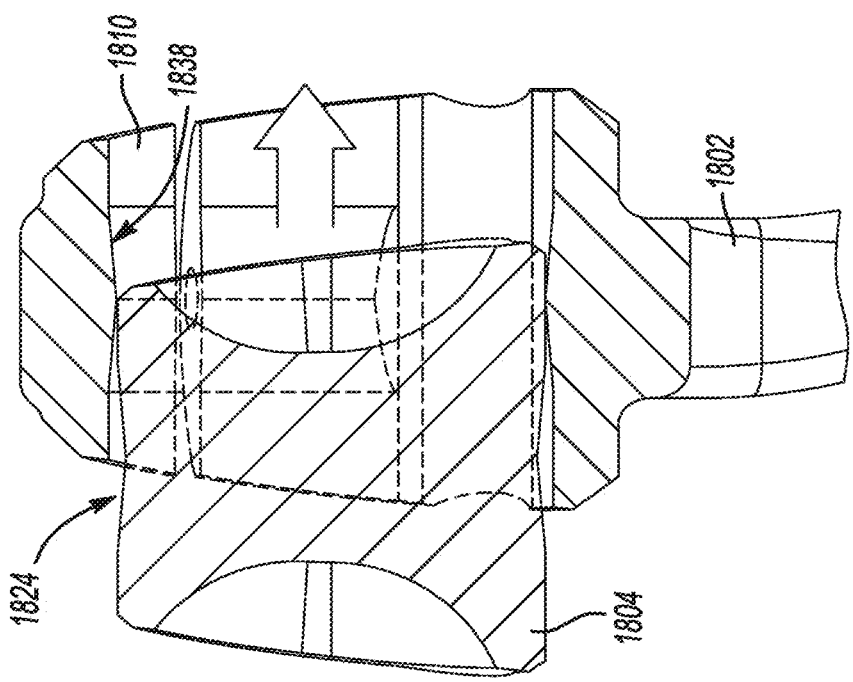
_Fig-64_
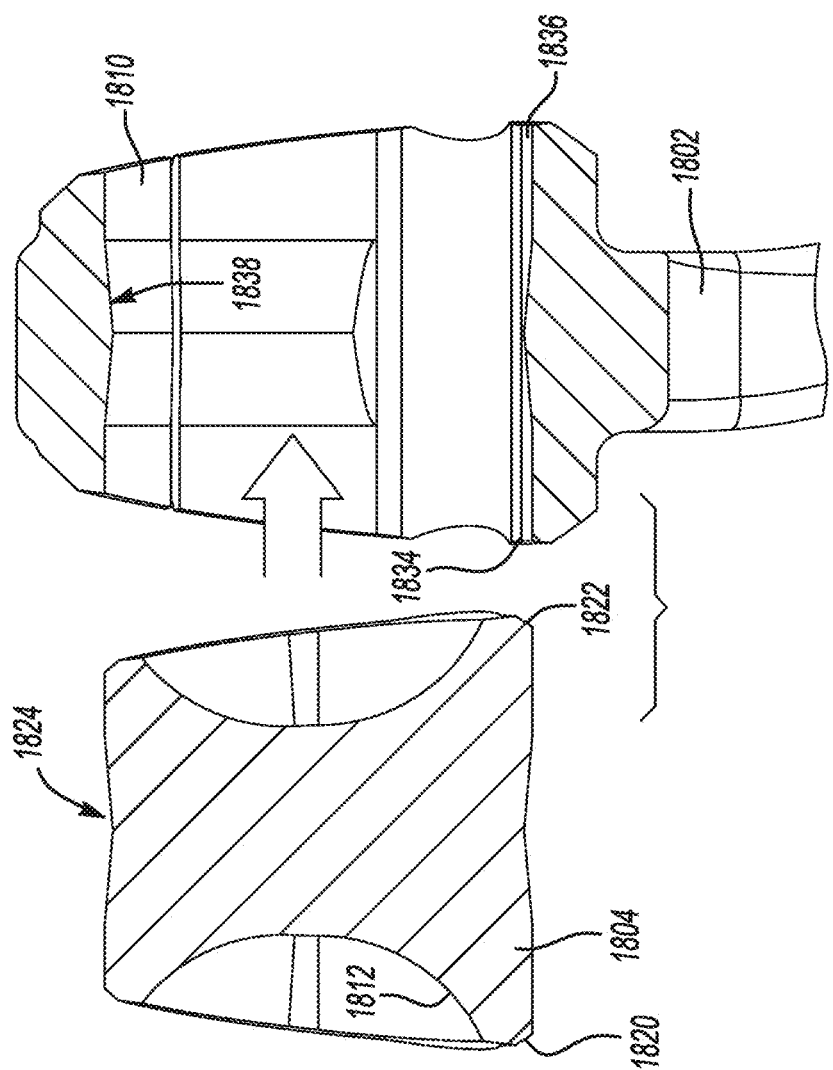
_Fig-63_

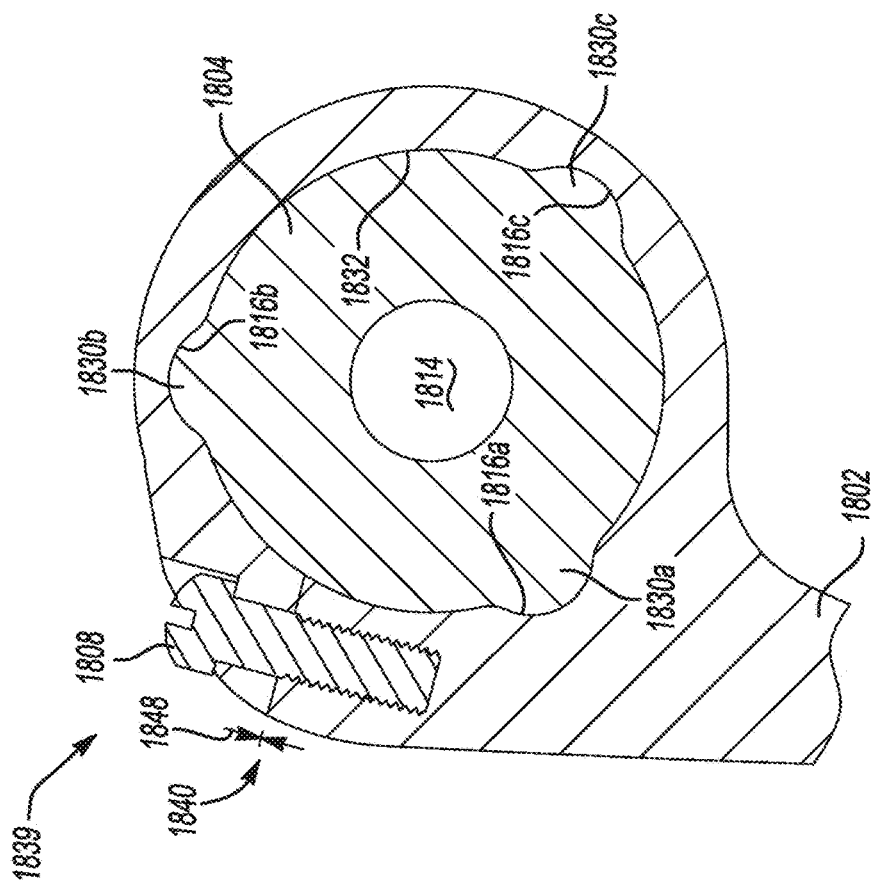
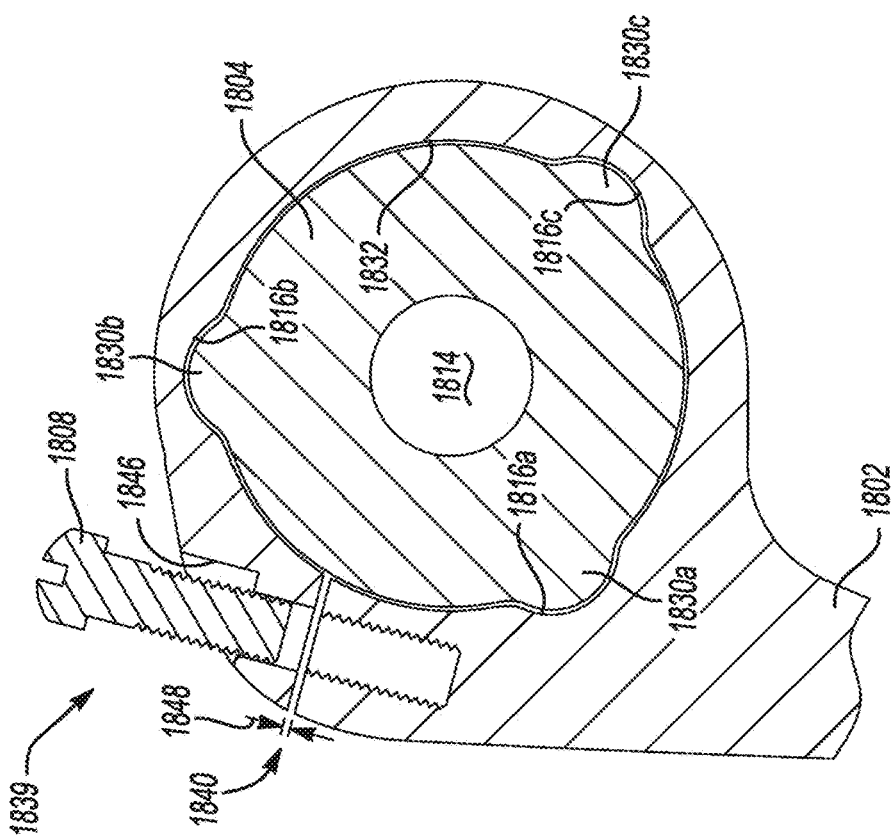

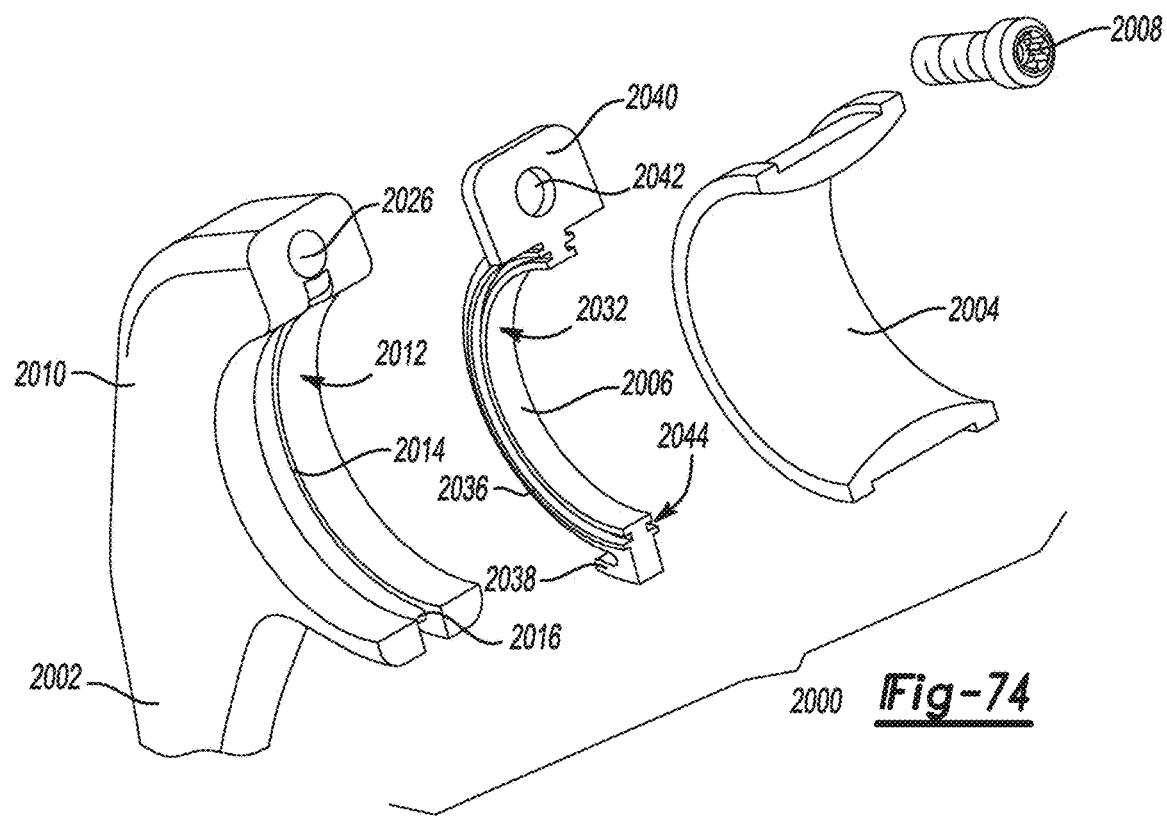
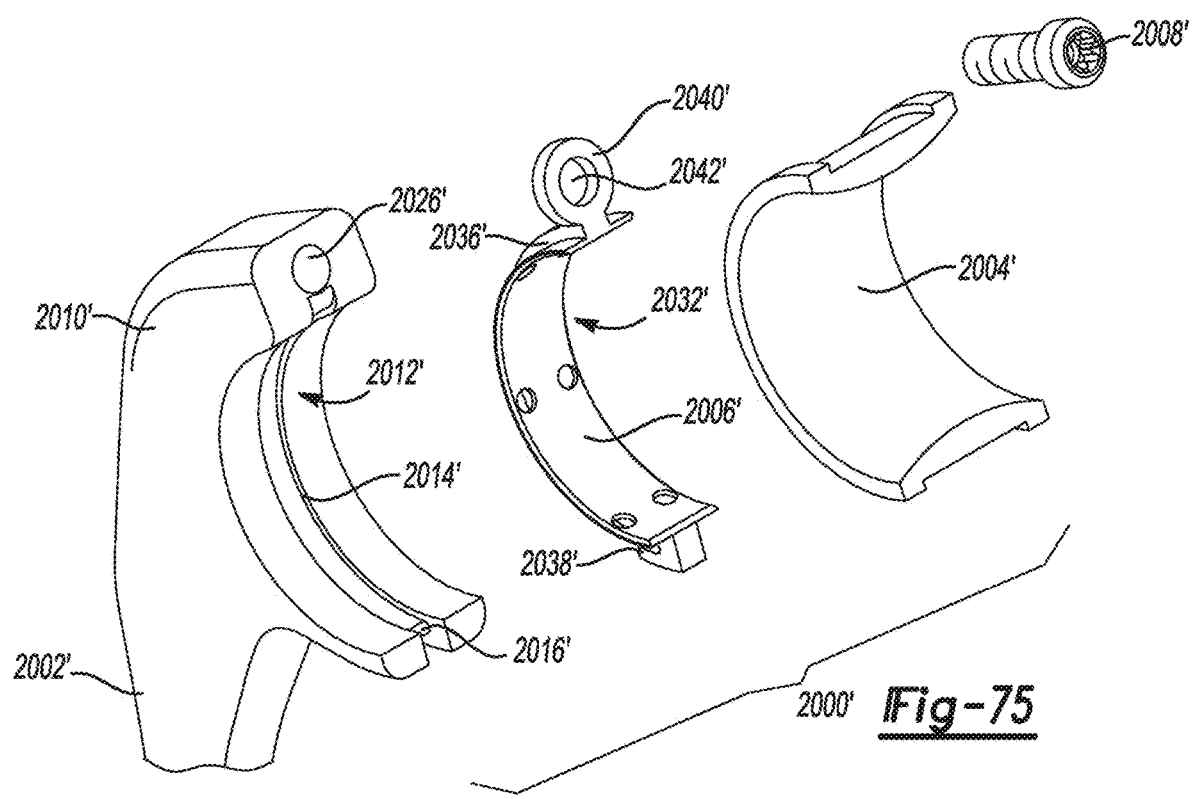

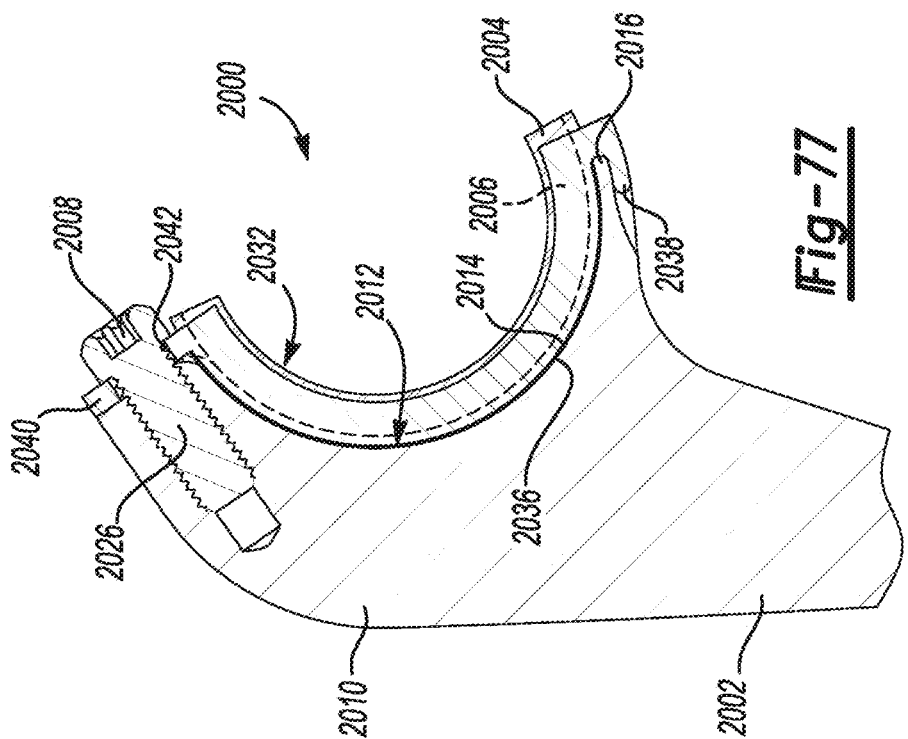
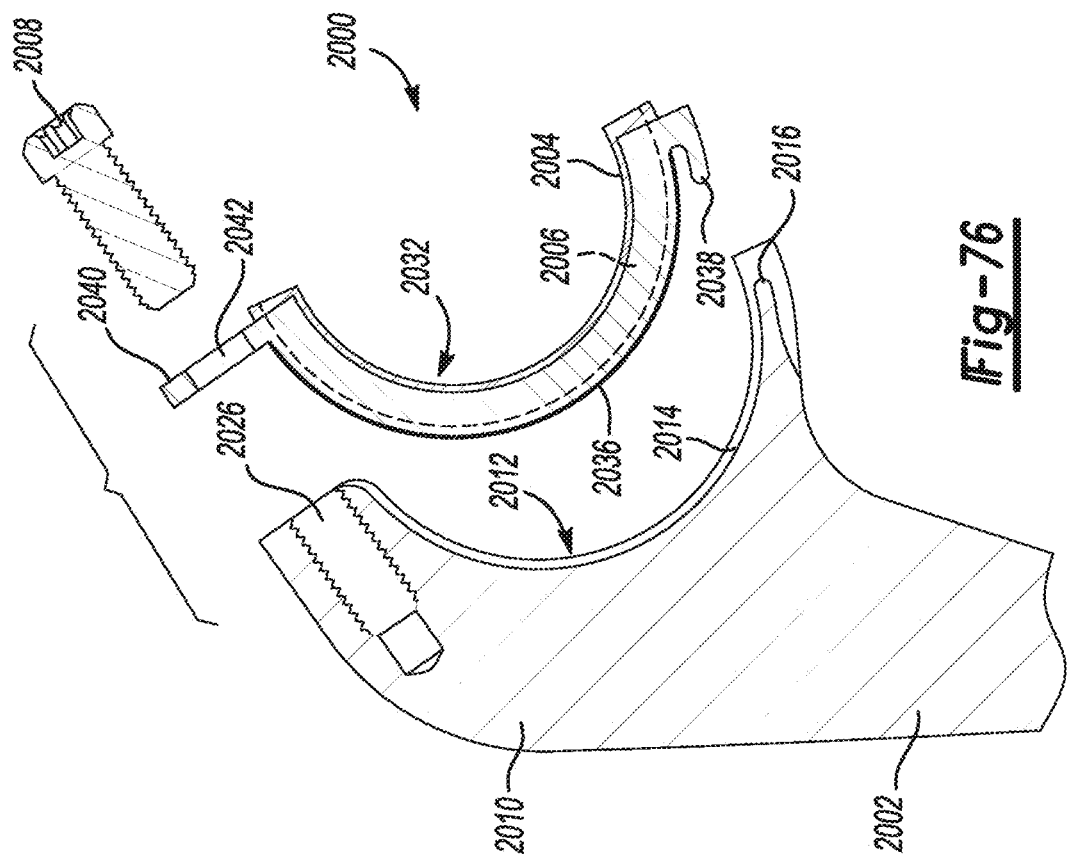

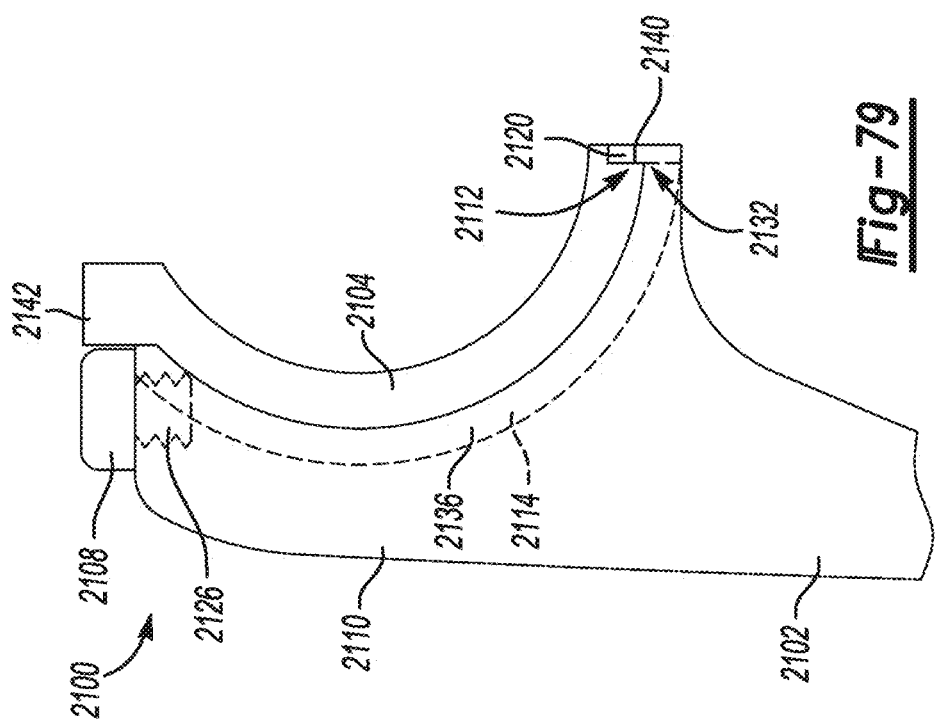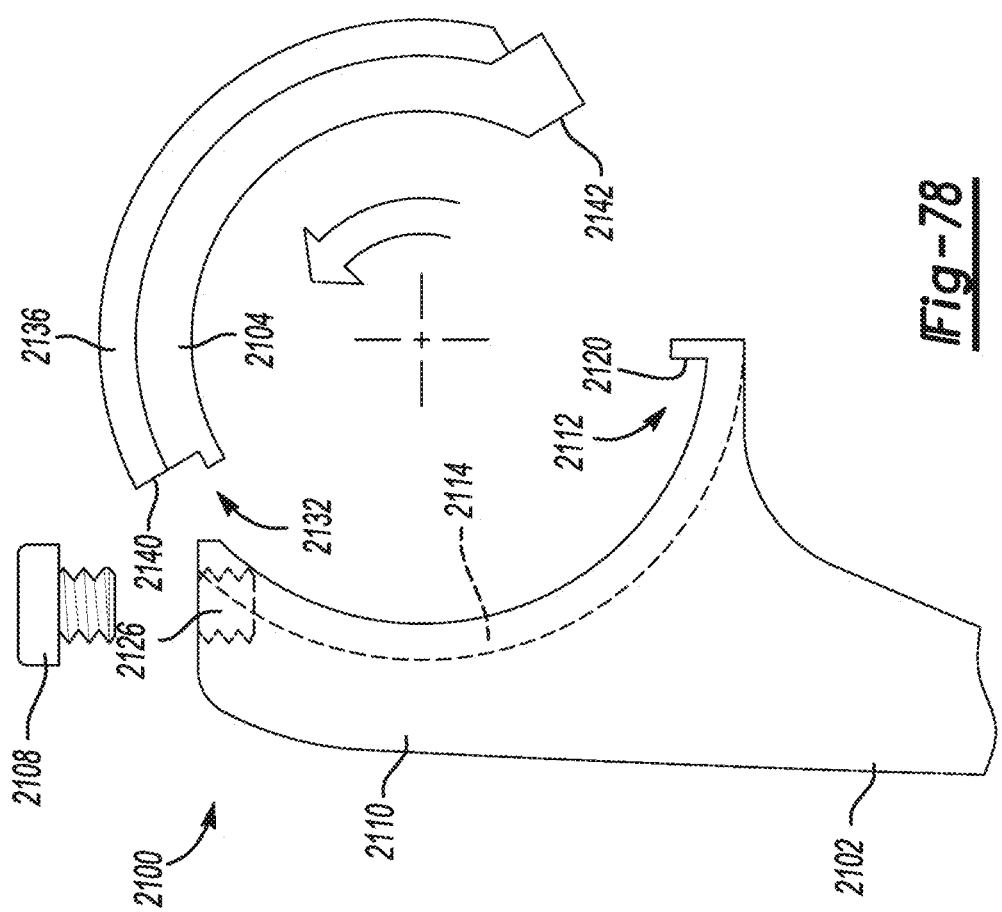

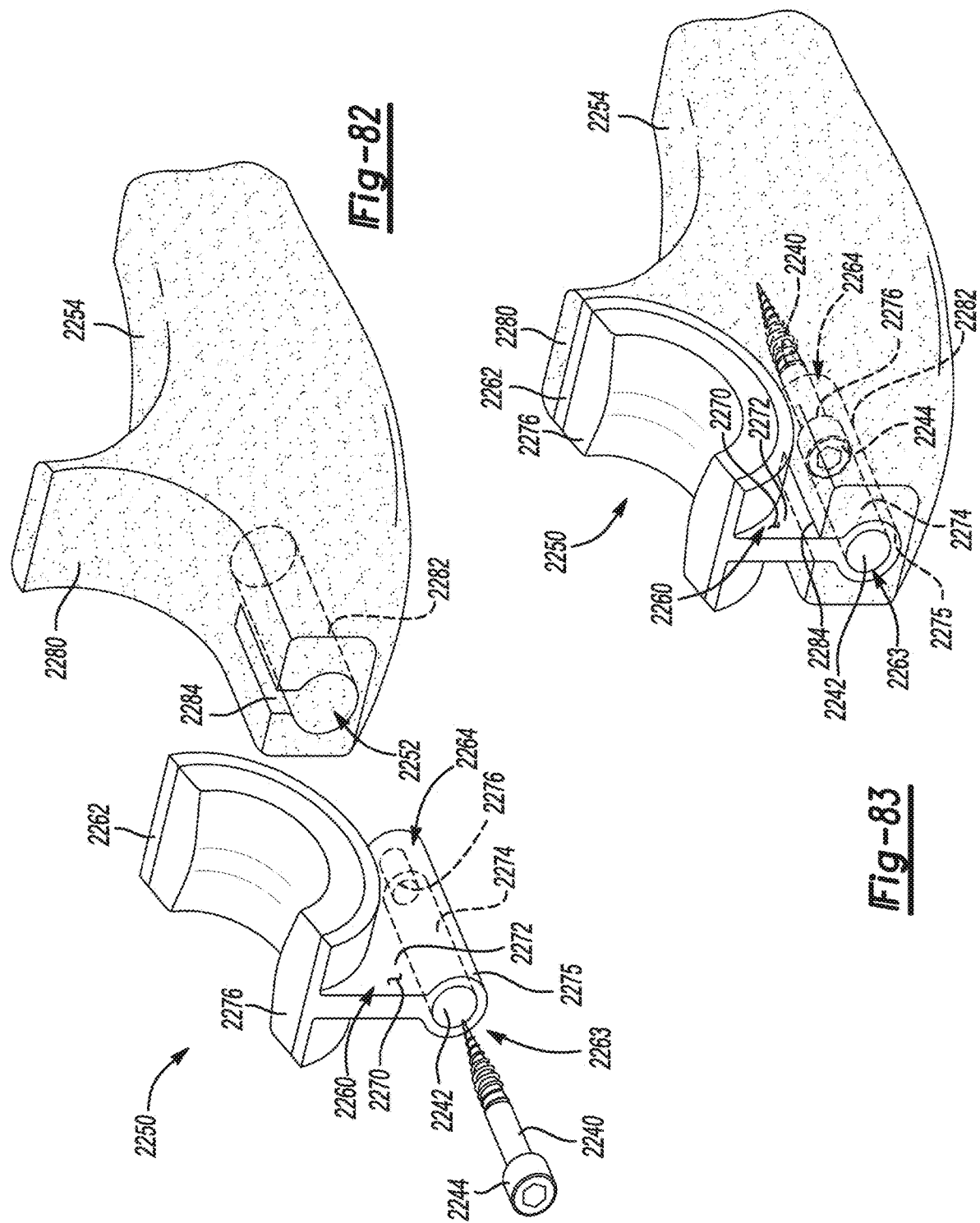

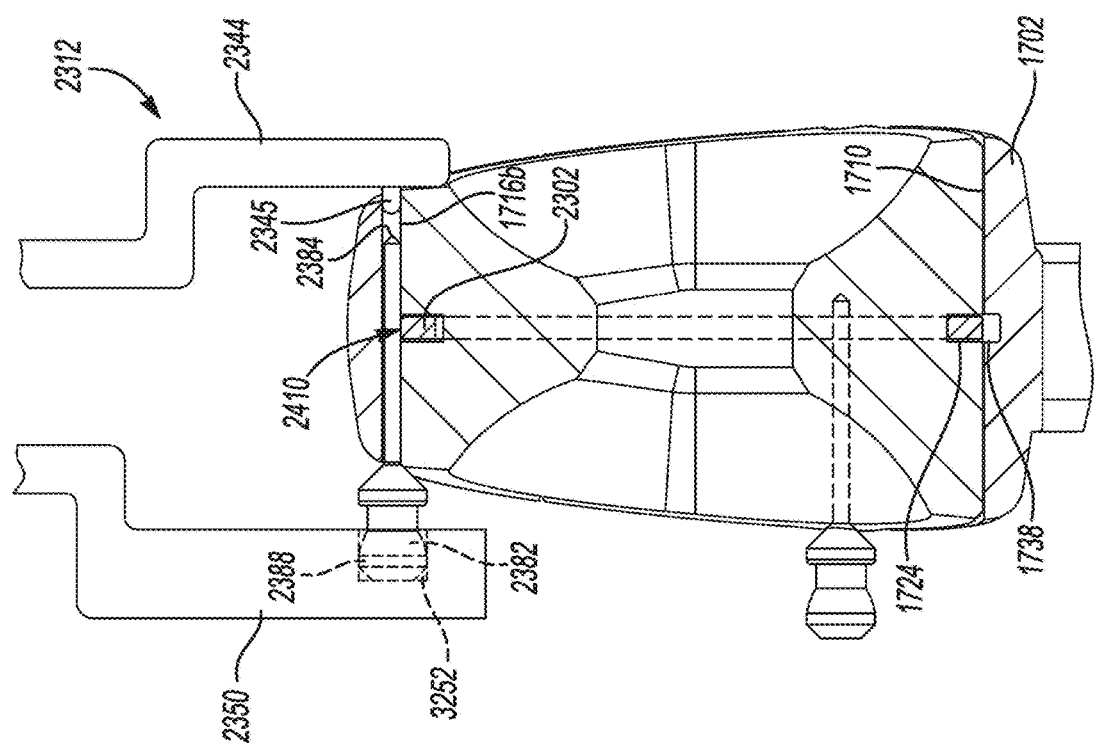
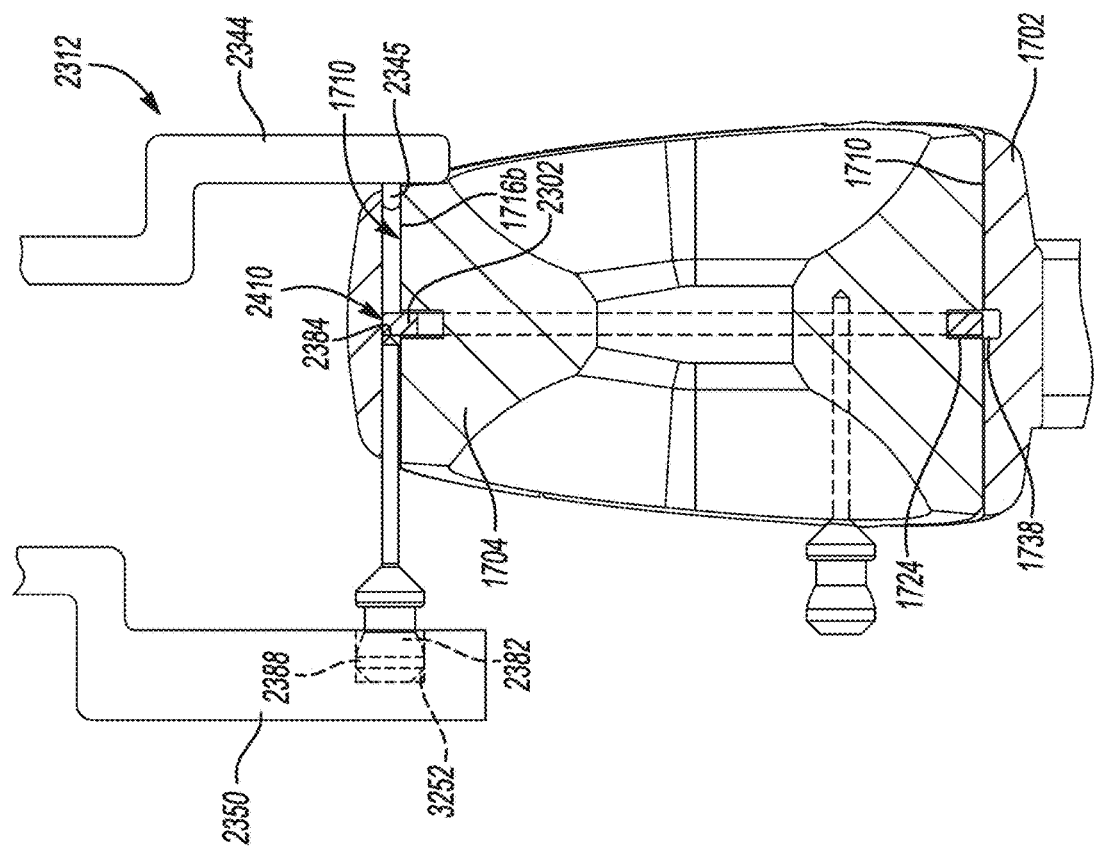

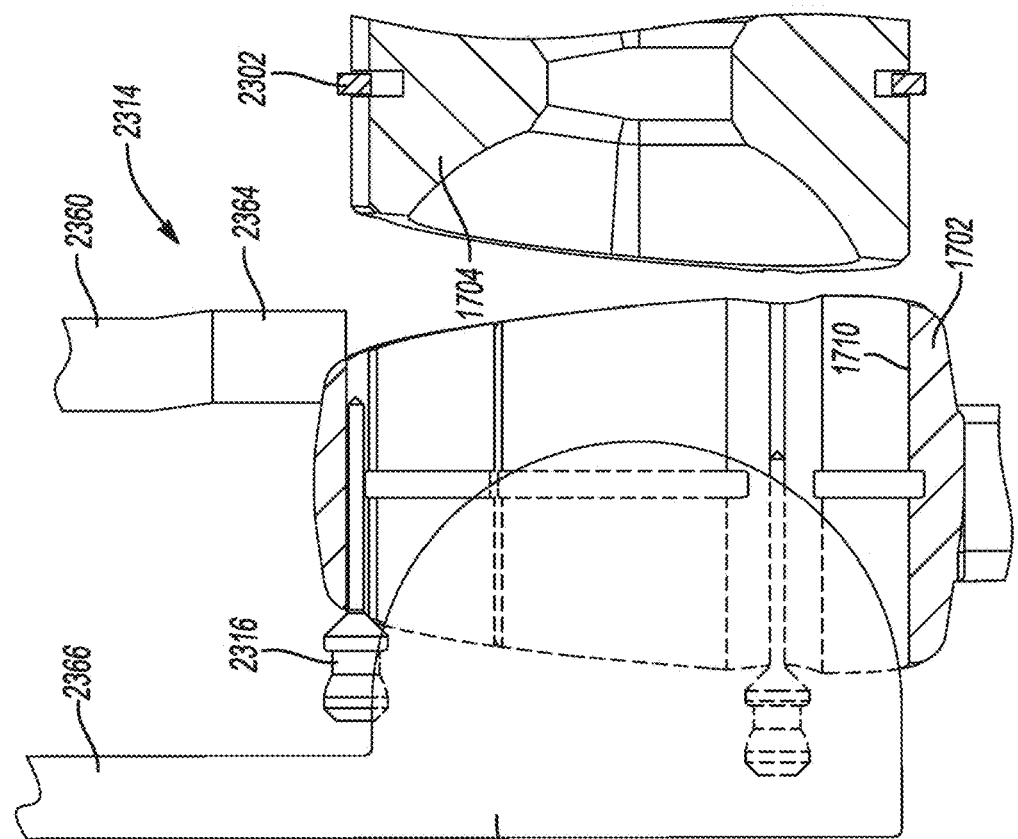
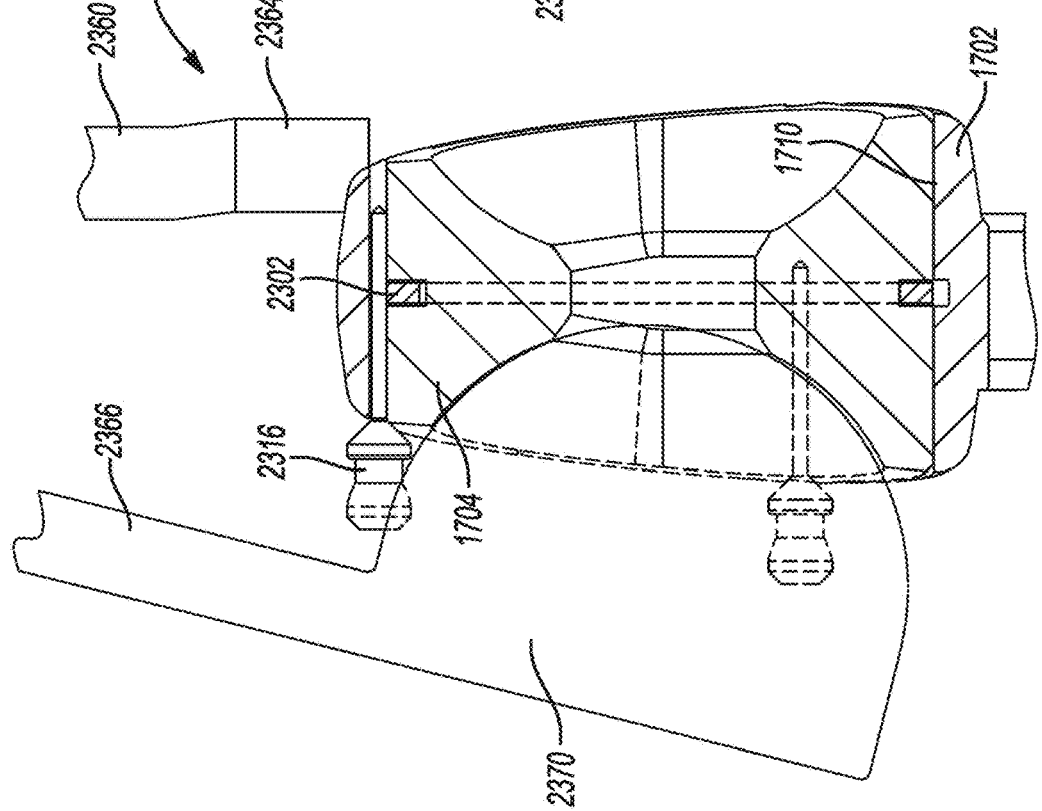

ELBOW PROSTHESIS

CROSS-REFERENCE TO RELATED APPLICATIONS

This application is a continuation of U.S. patent application Ser. No. 14/221,383, filed Mar. 21, 2014, which is a divisional of U.S. patent application Ser. No. 12/780,424, filed on May 14, 2010, which is a continuation-in-part of U.S. patent application Ser. No. 12/562,616, filed on Sep. 18, 2009, which is a continuation-in-part of U.S. patent application Ser. No. 12/391,904, filed on Feb. 24, 2009, which is a continuation-in-part of U.S. patent application Ser. No. 11/384,943 filed on Mar. 17, 2006 (now U.S. Pat. No. 8,585,768), which is a continuation-in-part of U.S. patent application Ser. No. 10/333,140 filed on Jan. 15, 2003 (now U.S. Pat. No. 7,247,170), which is a National Stage of International Application No. PCT/US01/22338 (published as WO 02/05728), filed Jul. 17, 2001, which claims priority to U.S. Provisional Application No. 60/219,103 filed Jul. 18, 2000. Each of these applications are incorporated herein by reference.

U.S. patent application Ser. No. 11/780,365 filed on Sep. 19, 2007 which is now U.S. Pat. No. 7,625,406 and U.S. patent application Ser. No. 11/780,370 filed on Sep. 19, 2007 which is now U.S. Pat. No. 7,604,666 disclose related subject matter. These applications are also incorporated herein by reference.

FIELD

The present teachings relate generally to prosthetic devices used in arthroplasty and more particularly to a modular elbow prosthesis.

BACKGROUND

The present teachings relate generally to prosthetic devices used in arthroplasty and more particularly to a modular elbow prosthesis.

Linked or constrained elbow prostheses are known which comprise simple hinge arrangements, one component of which is attached to the end of the humerus and the other component of which is attached to the end of the ulna. The humeral component includes a shaft, which is cemented into a prepared cavity in the end of the humerus, and the ulnar component includes a shaft, that is cemented to the end of the ulna. The components of the prosthesis are connected together by means of a hinge pin so that the prosthesis allows a single degree of freedom of movement of the ulna relative to the humerus.

One example of a linked elbow prostheses is disclosed in U.S. Pat. No. 6,027,534 to Wack et al. In several respects, the linked embodiment of the '534 patent is typical of the designs for linked elbow prostheses in that it includes a humeral stem that terminates at a yoke at its distal end, a bearing component, a retaining pin and an ulna stem. The bearing component includes an oversized hole that is aligned with the longitudinal axis of the bearing and adapted to accept the retaining pin in a slip-fit condition. The distal end of the bearing component is coupled to the ulna stem. Despite the relatively widespread use of designs of this type, several drawbacks have been noted.

One significant drawback concerns the assembly of the elbow prosthesis after the surgeon has cemented the humeral and ulna stems to their respective bones. In using such conventionally configured linked elbow prosthesis devices, it is frequently necessary for the surgeon to drill a fairly large hole through the humerus so that the retaining pin may be inserted to the yoke of the humeral stem and the humeral bearing component. As a high degree of accuracy is typically required to ensure proper alignment between the hole in the humerus and the hole in the yoke of the humeral stem, a significant cost can be associated with this step in the installation of an elbow prosthesis due to the cost of the tooling used and the amount of time required to complete this step. The other method for attaching the prosthetic device includes inserting the device in its linked condition or placing the remaining piece into the yoke prior to fully seating the humeral component into the bone. This later method is typically somewhat difficult, given the limited amount of joint space that is available and the time constraints associated with the use of a PMMA bone cement.

Unlinked, or unconstrained, elbow prostheses are known which are similar to linked elbow prostheses but do not have a specific component which mechanically couples the humeral and ulnar stems together. Rather, the prosthetic device is held together by the patient's natural soft tissues. One example of an unlinked elbow prostheses is also disclosed in U.S. Pat. No. 6,027,534 to Wack et al. In several respects, the unlinked embodiment of the '534 patent is similar to the linked embodiment discussed above in that it includes a humeral stem that terminates at a yoke at its distal end, a humeral bearing component, a retaining pin, an ulnar bearing component and a ulnar stem. The outer surface of the humeral bearing is contoured to match the contour of the ulnar bearing component. Despite the relatively widespread use of designs of this type, several drawbacks have been noted.

For instance, a retaining pin that is transverse to the longitudinal axis of the patient is employed, thereby making its removal difficult if a bearing need to be replaced.

SUMMARY

An elbow prosthesis constructed in accordance to one example of the present teachings can include a first stem structure that is operable to be positioned in a first bone of a joint. The first stem structure can include a first stem portion and a cage structure. The first stem portion may be operable to be positioned in the first bone. The cage structure can be formed generally between an inner sidewall and an outer surface. The stem portion can have opposing surfaces that define a disconnect formed entirely through the cage structure from the inner sidewall to the outer surface. A first bearing component can have an exterior cage opposing surface. The first bearing component can be selectively inserted into the cage structure from an insertion position to an installed position. A fastener can be threadably advanced into an engaged position with the cage structure to reduce a gap defined between the opposing surfaces of the disconnect while radially contracting the cage structure around the first bearing.

According to additional features, at least one of opposing surfaces of the disconnect is non-linear from the inner sidewall to the outer surface. The inner sidewall of the cage structure can have a first groove and the exterior cage opposing surface can have a second groove that opposes the first groove in the installed position. A lock ring can partially nest within each of the first and second grooves in the assembled position.

According to still other features, the cage structure can include at least one tabbed entry formed on the inner sidewall that slidably accepts at least one tab formed on the exterior cage opposing surface of the first bearing component in the installed position. The at least one tab and tab entry respectively can cooperate to inhibit rotation of the first bearing around the inner sidewall of the cage structure in the assembled position.

According to additional features, the inner sidewall can have a first V-shaped cross-section. The exterior cage opposing surface of the first bearing component can have a second V-shaped cross-section that cooperatively engages the first V-shaped cross-section to inhibit medial/lateral movement of the first bearing in the installed position. A second bearing component can be provided that is associated with a second stem structure. The second bearing component can be operable to cooperatively rotate with the first bearing component. The first stem structure can be adapted to be implanted into one of a humerus or ulna. The second stem structure can be adapted to be implanted into the other of the humerus and ulna.

An elbow prosthesis according to another example of the present teachings can include a stem structure that is operable to be positioned into a bone of a joint. The stem structure can include a stem portion and C-shaped body portion. The stem portion can be operable to be positioned in the bone. The C-shaped body portion can have a first retaining mechanism formed thereon. The elbow prosthesis can further comprise an articulating component that has a second retaining mechanism formed thereon. The articulating component can be rotatably advanced from an insertion position to an assembled position, such that the first and second retaining mechanisms cooperatively interlock to inhibit medial/lateral movement of the articulating component relative to the C-shaped body portion of the stem structure. The first retaining mechanism can comprise outwardly extending rails that are formed on the C-shaped body portion. The first retaining mechanism can further comprise a stop having stop surfaces provided on one end of the rails. The second retaining mechanism can comprise a channel having a geometry that cooperatively receives the rails of the C-shaped body portion. The articulating component can comprise a catch having catch surfaces that engage the stop surfaces in the assembled position. A plate and a fastener can further be provided. The fastener can extend through a passage in the plate that threadably couples to the stem portion. The plate can inhibit rotation of the articulating component from the assembled position to the insertion position. A plurality of articulating components can be provided each having various geometries. One of the articulating components from the plurality can be selected and coupled to the stem structure according to a given patient's specific needs.

An elbow prosthesis constructed in accordance to other features of the present teachings can include a stem structure operable to be positioned in a bone of a joint. The stem structure can include a stem portion and a C-shaped body portion. The stem portion can be operable to be positioned in the bone. The C-shaped body portion can have a first retaining mechanism thereon. The elbow prosthesis can further comprise an articulating component having a second retaining mechanism formed thereon. One of the first and second retaining mechanisms comprises a rail and the other of the first and second mechanisms comprises a groove. The articulating component is advanced from an insertion position to an installed position, such that the first and second retaining mechanisms cooperatively interlock to inhibit medial/lateral movement of the articulating component relative to the C-shaped body portion of the stem structure.

According to other features, the articulating component can comprise a bearing portion and a rail. The rail can have a first end that includes a plate and a second end that includes a hook. The plate can include an eyelet adapted to receive a fastener therethrough. The fastener can threadably couple the articulating component to the stem structure. The hook can cooperatively engage an end of the stem portion at the groove.

Further areas of applicability will become apparent from the description provided herein. It should be understood that the description and specific examples are intended for purposes of illustration only and are not intended to limit the scope of the present disclosure.

BRIEF DESCRIPTION OF THE SEVERAL VIEWS OF THE DRAWINGS

Additional advantages and features of the present teachings will become apparent from the subsequent description and the appended claims, taken in conjunction with the accompanying drawings, wherein:

FIG. 1A is an exploded perspective view of a linked prosthetic joint kit similar to that of FIG. 1 but constructed in accordance with a first alternate embodiment of the first aspect of the present teachings;

FIG. 18 is a cross-sectional view taken along the line 18-18 of FIG. 16;

FIG. 19A through 19D are side elevation views of bearing inserts constructed with varying degrees of varus/valgus constraint;

FIG. 33 is a view similar to that of FIG. 31 but illustrating a second alternative coupling means;

FIG. 34 is a view similar to that of FIG. 31 but illustrating a third alternative coupling means;

FIG. 55 is a cross-sectional view of the stem assembly showing a bearing member in an insertion position relative to a stem member;

FIG. 56 is a cross-sectional view of the stem assembly of FIG. 55 and shown during assembly of the bearing into a cage of the stem component;

FIG. 60 is a perspective view of a stem component constructed in accordance to additional features;

FIG. 61 is a perspective view of a stem assembly constructed in accordance to additional features of the present teachings;

FIG. 63 is a cross-sectional view of the stem component and bearing of FIG. 62 and shown in an insertion position;

FIG. 64 is a cross-sectional view of the bearing and stem component of FIG. 63 and shown with the bearing partially inserted into a cage structure of the stem component during an assembly step;

FIG. 66 is a cross-sectional view of the stem assembly of FIG. 62 and shown with a fastener being threadably assembled into the stem component;

FIG. 67 is a cross-sectional view of the stem assembly of FIG. 66 and shown with a fastener threaded into the stem component in an assembled position;

FIG. 74 is an exploded perspective view of portions of the ulnar stem assembly of FIG. 73;

FIG. 75 is an exploded perspective view of portions of an unlinked ulnar stem assembly having a retaining mechanism constructed in accordance to additional features of the present teachings;

FIGS. 76-77 are an assembly sequence showing the modular articulating component being coupled to the stem component according to one example;

FIGS. 78-79 are an assembly sequence showing an articulating component and stem component according to additional features and illustrating an exemplary sequence of coupling the articulating component to the stem component;

FIGS. 82 and 83 illustrate an exemplary assembly sequence of another unlinked ulnar stem assembly according to additional features;

FIGS. 87 and 88 are an exemplary sequence illustrating a second tool used to further advance the extractor pins around the lock ring to compress the lock ring into the groove of the ulna bearing;

FIGS. 91 and 92 are an exemplary sequence illustrating a third tool urging the bearing member out of the cage structure of the ulna stem according to one example of the present teachings.

DETAILED DESCRIPTION OF VARIOUS EMBODIMENTS

Figure 1:
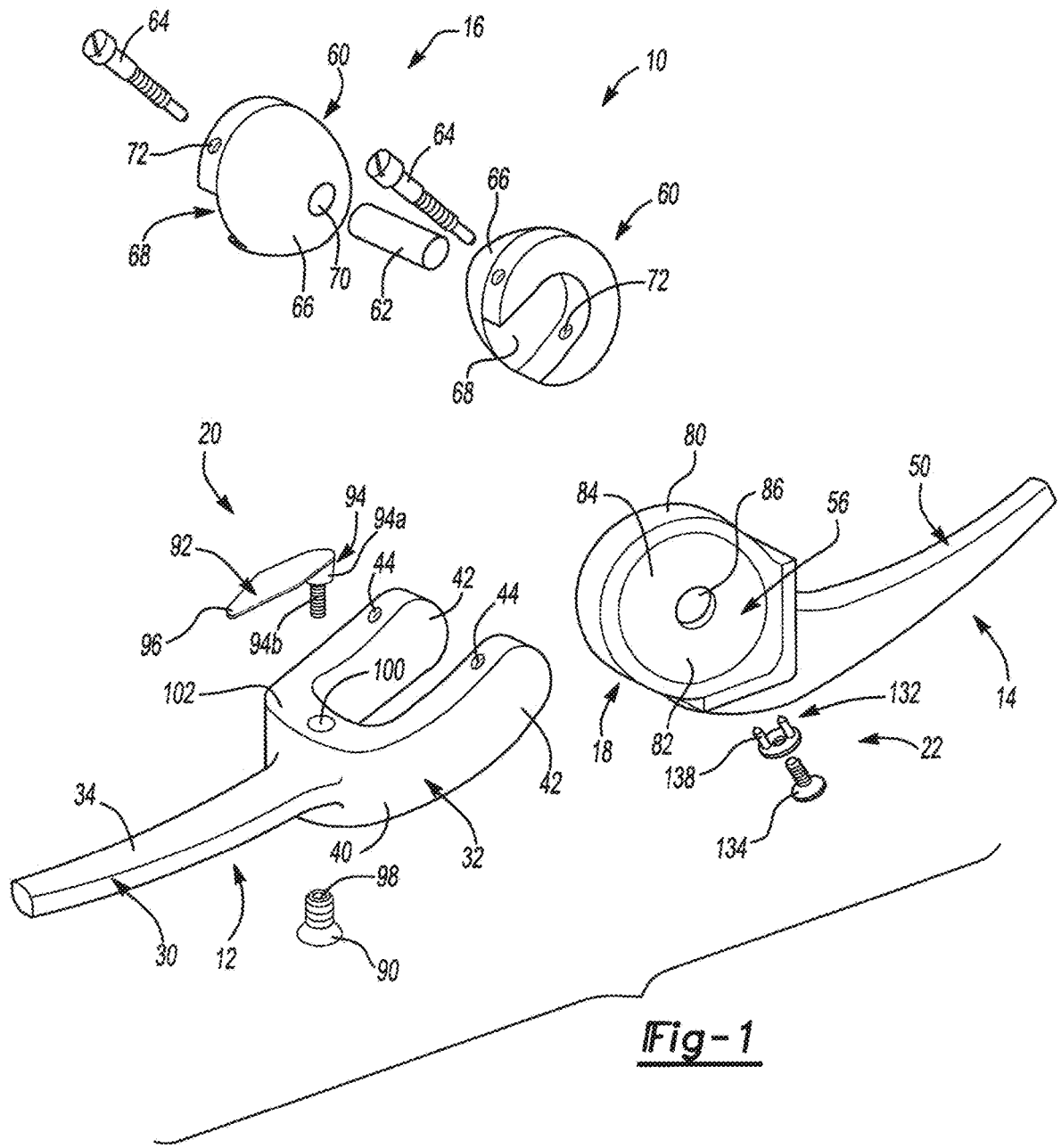
FIG. 1 is an exploded perspective view of a linked prosthetic joint kit constructed in accordance with the teachings of a first aspect of the present teachings.

The following description is merely exemplary in nature and is not intended to limit the present disclosure, application, or uses. It should be understood that throughout the drawings, corresponding reference numerals indicate like or corresponding parts and features.

Figure 2:
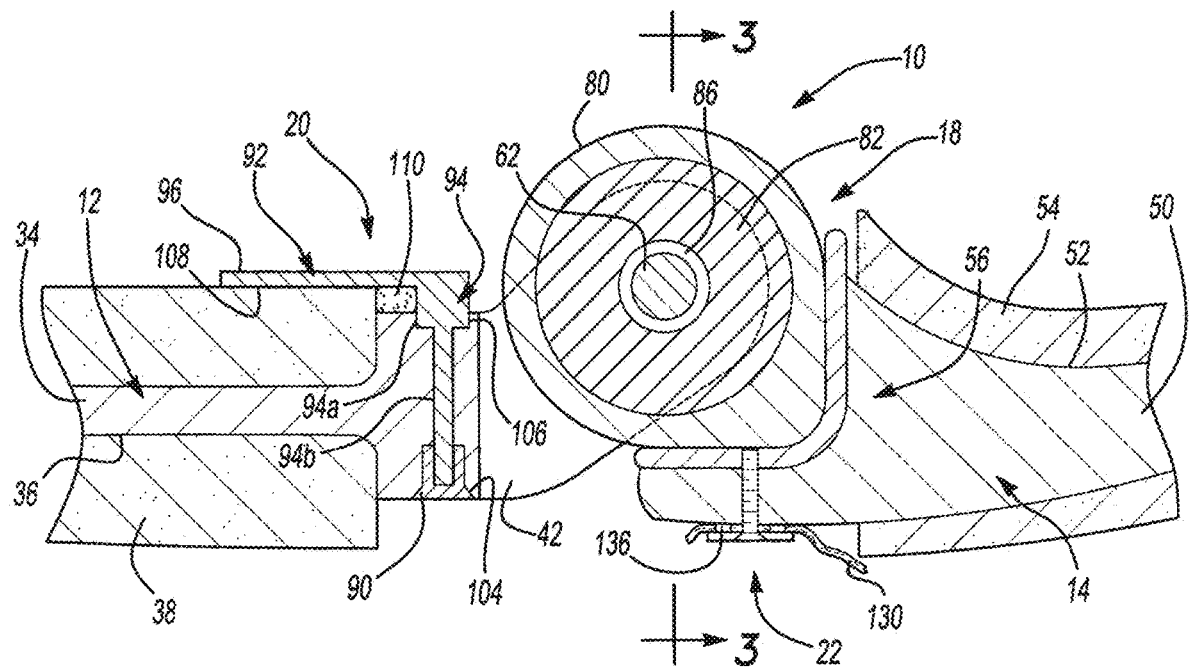
FIG. 2 is a longitudinal cross-sectional view of the linked prosthetic joint kit of FIG. 1 implanted in the arm of a person.
Figure 3:
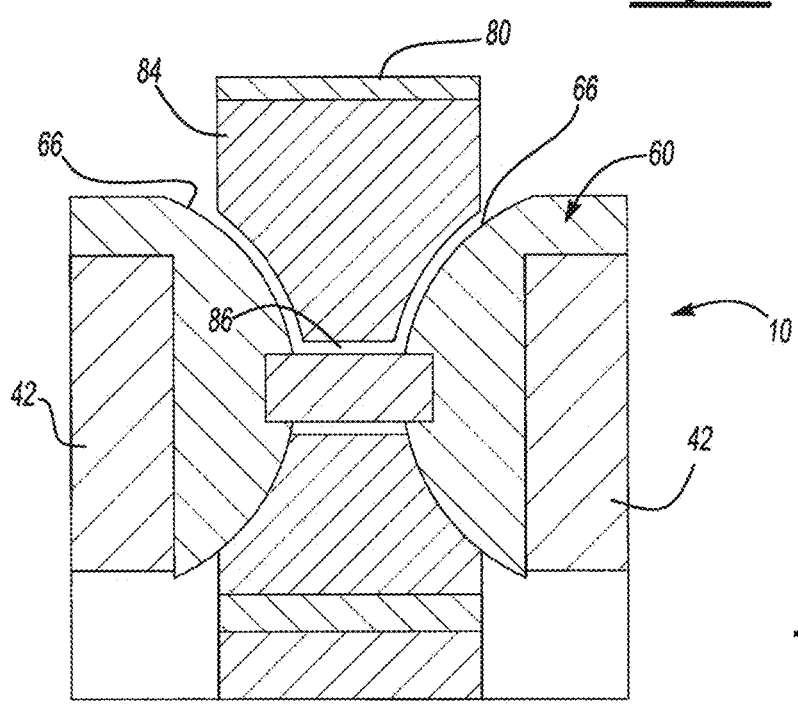
FIG. 3 is a cross-sectional view taken along the line 3-3 of FIG. 2.

With reference to FIGS. 1, 2 and 3 of the drawings, a linked prosthetic joint device constructed in accordance with the teachings of a first aspect is generally indicated by reference number 10. Although the particular prosthesis illustrated and discussed relates to a prosthesis for use in reconstructing an elbow, it will be understood that the teachings have applicability to other types of linked and unlinked prosthetic devices. As such, the scope of the present teachings will not be limited to applications involving elbow prosthesis but will extend to other prosthetic applications.

In the particular embodiment illustrated, linked prosthetic joint 10 is shown to include a first stem structure 12, a second stem structure 14, a first bearing component 16, a second bearing component 18, a modular flange 20 and a tissue fastener 22. First stem structure 12 includes a proximal portion 30 and a distal portion 32. Proximal portion 30 includes a stem member 34 which is adapted to fit within the medullary canal 36 of a humerus 38. Distal portion 32 includes a generally U-shaped member 40 which is fixedly coupled to the distal end of proximal portion 30. U-shaped portion 40 includes a pair of spaced-apart legs or furcations 42. A threaded fastener aperture 44 extends perpendicularly through each of the furcations 42.

Second stem structure 14 includes a distal portion 50 which is adapted to fit within the medullary canal 52 of an ulna 54. Second stem structure 14 also includes a proximal portion 56 which is coupled to second bearing component 18. In the particular embodiment illustrated, second bearing component 18 is fixedly coupled to second stem structure 14. However, second bearing component 18 may also be releasably coupled to second stem structure 14 as shown in FIGS. 9 through 12.

First bearing component 16 includes a pair of condyle portions 60, a pin portion 62 and a pair of fasteners 64. Condyle portions 60 and pin portion 62 are formed from a suitable material, such as cobalt chromium alloy. Each condyle portion 60 is shown to include a spherically-shaped bearing portion 66, slotted aperture 68, a pin aperture 70 and a mounting aperture 72. The pair of spherically shaped bearing portions 66 collectively form a first bearing surface. Pin aperture 70 is sized to receive an end of pin portion 62 to permit pin portion 62 to slidingly engage condyle portions 60. Pin 62 can also be fixedly coupled with one of said condyle portion 60 and slidingly engage second of said condyle portion 60. Each of the slotted apertures 68 is sized to slidingly engage one of the furcations 42.

Second bearing component 18 is shown to include a cage portion 80 which is fixedly coupled to the proximal portion 56 of second stem structure 14 and a bearing member 82 which is fixedly coupled to the cage portion 80. Bearing member 82 includes a pair of spherical bearing portions 84 which are configured to engage the spherically shaped bearing portions 66 of the condyle portions 60. The pair of spherical bearing surfaces 84 collectively form a second bearing surface that mates with the first bearing surface. Bearing member 82 also includes a through hole 86 which is adapted to receive pin portion 62, preferably without transmitting load therebetween (i.e., pin portion 62 preferably does not contact the surfaces of through hole 86). In the particular embodiment illustrated, bearing member 82 is fabricated from polyethylene which has been molded to cage portion 80. Alternatively, bearing member 82 may be fabricated from any other appropriate material such as a stainless steel, ceramic, pyrolytic carbon, cobalt chrome (CoCr) etc.

To use linked prosthetic joint 10, first stem structure 12 is implanted in humerus 38 such that proximal portion 34 is located in the medullary canal 36 of the humerus 38 as shown in FIG. 2. Second stem structure 14 is similarly implanted in ulna 54 such that distal portion 50 is located in the medullary canal 52. Pin portion 62 is next inserted to the pin aperture 70 of one of the condyle portions 60 and the opposite end of pin portion 62 is placed through hole 86 and into the pin aperture 70 of the other one of the condyle portions 60. Second bearing component 18 is positioned adjacent the distal portion 32 of first stem structure 12, furcations 42 are aligned to their respective slotted aperture 68 and condyle portions 60 are slidingly engaged to furcations 42. Fasteners 64 are inserted through their respective mounting apertures 72 and threadably engaged to their threaded fastener aperture 44. When fully seated, each of the fasteners 64 extends through its respective furcation 42 to prevent condyle portion 60 from rotating relative to the furcation 42. At this point, first and second bearing components 16 and 18 hingedly couple first and second stem structures 12 and 14 together in a linked or constrained manner.

Construction of linked prosthetic joint 10 in this manner is highly advantageous in that it permits the surgeon to insert the first and second stem structures 12 and 14 prior to or after assembling linked prosthetic joint 10, as well as permits linked prosthetic joint 10 to be assembled in a relatively small space as compared to most of the other prosthetic joints that are known in the art. Furthermore, the spherical configuration of first and second bearing surfaces 66 and 84 permits the load which is transmitted through linked prosthetic joint 10 to be spread out over a relatively large area, rather than concentrated at a single point or over a line of contact to thereby improve the durability of linked prosthetic joint 10.

Modular flange 20 may be employed to increase the resistance of first stem structure 12 to rotation within medullary canal 36. In FIGS. 1 and 2, modular flange 20 is shown to include an internally threaded fastener 90, and a unitarily formed flange structure 92 having a mount member 94 and a flange member 96. Mount member 94 includes a locating cylinder 94a which is fixedly coupled to flange member 96 at its base and an externally threaded fastener 94b which is coupled to an opposite side of locating cylinder 94a. A mounting hole 98, which is sized to receive fastener 94b, extends through internally threaded fastener 90. A bore 100 formed through the base 102 of U-shaped portion 40 has a first portion 104 which is tapered at one end to engage the edges of internally threaded fastener 90 and second portion 106 which is counter bored at the other end to engage the locating cylinder 94a of mount member 94. Internally threaded fastener 90 is threadably engaged to fastener 94b to fixedly but removably couple modular flange 20 to first stem structure 12.

Modular flange 20 may be employed to generate a clamping force which clamps a portion 108 of the humerus 38 between the proximal portion 34 of the first stem structure 12 and the flange member 96. Preferably, a bone graft 110 is employed in conjunction with modular flange 20 such that the clamping force produced by modular flange 20 is also transmitted to bone graft 110 to promote the attachment of bone graft 110 to humerus 38 and the subsequent growth of bone graft 110. Those skilled in the art will understand that alternatively, a flange (not shown) which is unitarily formed with first stem structure 12 may be incorporated into linked prosthetic joint 10 to thereby increase the resistance of first stem structure 12 to rotation within medullary canal 36. However, a flange which is unitarily formed with first stem structure 12 could not be employed to generate a clamping force which clamps a portion 108 of the humerus 38 between the proximal portion 34 of the first stem structure 12 and the flange.

Tissue fastener 22 is shown in FIGS. 1 and 2 to be a device for attaching soft tissue, such as tendons 130, to linked prosthetic joint 10. In this regard, the specific configuration of tissue fastener is beyond the scope of this disclosure. Examples of suitable tissue fasteners are discussed in U.S. Pat. Nos. 5,380,334, 5,584,835, 5,725,541, 5,840,078 and 5,980,557 which are hereby incorporated by reference as if fully set forth herein.

In the particular embodiment illustrated, tissue fastener 22 is shown to include a tissue clamp 132 and a threaded fastener 134. Tissue clamp 132 includes an annular base 136 and a pair of prongs 138. Prongs 138 are forced through the soft tissue (e.g., tendons 130). Threaded fastener 134 is inserted through a hole in base 136 and threadably engaged to second stem structure 14 to fixedly but releasably couple tissue fastener 22 and the soft tissue to second stem structure 14. Those skilled in the art will understand that tissue fastener 22 may also be used in conjunction with first stem structure 12.

In FIG. 1A, a linked prosthetic joint device constructed in accordance with the teachings of an alternate embodiment of the first aspect of the present teachings is generally indicated by reference numeral 10a. Linked prosthetic joint 10a is shown to include first stem structure 12, second stem structure 14, first bearing component 16a, second bearing component 18a, modular flange 20 and tissue fastener 22.

First bearing component 16a is similar to first bearing component 16 in all respects except that it is unitarily formed. Accordingly, pin portion 62a is not removable form condyle portions 60a. Second bearing component 18a is similar to second bearing component 18 in all respects except that an insertion aperture 150 extends form through hole 86a outwardly through bearing member 82a and cage portion 80a. Accordingly, insertion aperture 150 renders the area of second bearing surface 84a somewhat smaller than second bearing surface 84. Second bearing surface 84a is otherwise identical to second bearing surface 84.

To use linked prosthetic joint device 10a, first and second stem structures 12 and 14 are initially inserted to the humerus and ulna and first bearing component 16a is fastened to the first stem structure 12 using techniques similar to that discussed above for prosthetic joint device 10. First bearing component 16a is then positioned adjacent second bearing component 18a such that pin portion 62a is in insertion aperture 150. Pin portion 62a is then forced toward through hole 86a. The distal end 152 of insertion aperture 150 is smaller than pin portion 62a to permit bearing member 82a to engage pin portion 62a in a snap fit manner, so as to inhibit the unintentional withdrawal of pin portion 62a from through hole 86a. As discussed above, through hole 86a is preferably larger in diameter than pin portion 62a. At this point, first and second bearing components 16a and 18a hingedly couple first and second stem structures 12 and 14 together in a linked manner.

Figure 4:
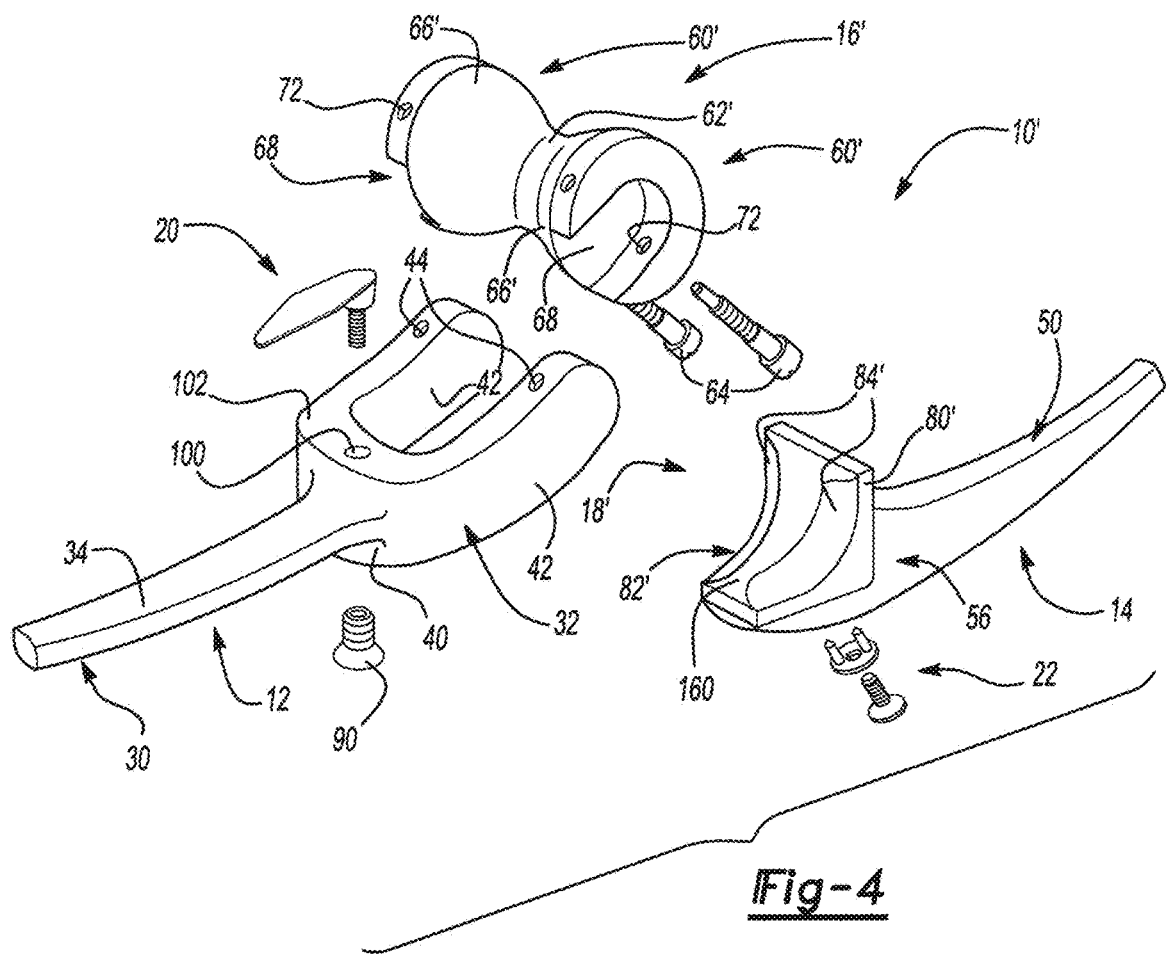
FIG. 4 is an exploded perspective view of an unlinked prosthetic joint kit constructed in accordance with the teachings of a first aspect of the present teachings.
Figure 5:
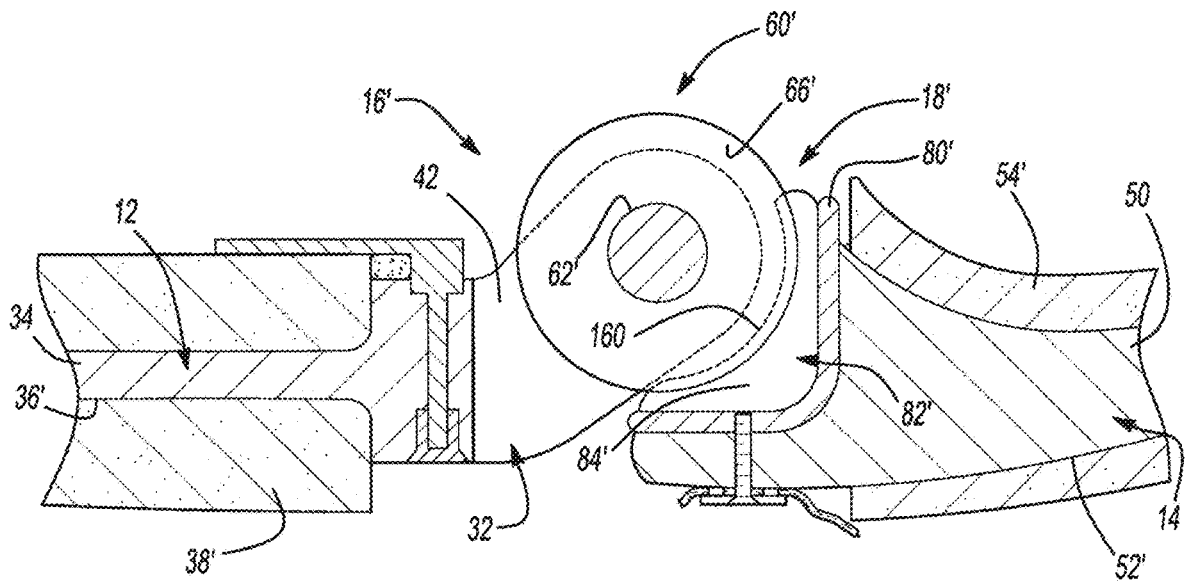
FIG. 5 is a longitudinal cross-sectional view of the unlinked prosthetic joint kit of FIG. 4 implanted in the arm of a person.

In FIGS. 4 and 5, an unconstrained or unlinked prosthetic joint device constructed according to a first aspect of the present teachings is generally indicated by reference number 10'. Unlinked prosthetic joint 10' is shown to include a first stem structure 12, a second stem structure 14, a first bearing component 16', a second bearing component 18', a modular flange 20 and a tissue fastener 22. Unlinked prosthetic joint 10' is shown to be operatively associated with a humerus 38' and an ulna 54' (FIG. 5), but those skilled in the art will understand that the teachings of the present teachings have application to prosthetic joints for other applications and as such, the scope of the present teachings will not be limited to elbow joints.

First bearing component 16' is similar to first bearing component 16 in that it includes a pair of condyle portions 60' and a pin portion 62'. However, first bearing component 16' is preferably unitarily formed with pin portion 62' extending between the spherically-shaped bearing portions 66' and fixedly coupling the spherically-shaped bearing portions 66' thereto. Like first bearing component 16, each of the condyle portions 60' of first bearing component 16' includes a slotted aperture 68 and a fastener aperture 72. Spherically shaped bearing portions 66' collectively form a first bearing surface. Like first bearing component 16, first bearing component 16' may be made from any appropriate bearing material, such as cobalt chromium alloy.

Second bearing component 18' is similar to second bearing component 18 in that it includes a cage portion 80' which is fixedly coupled to the proximal portion 56 of second stem structure 14 and a bearing member 82' which is fixedly coupled to the cage portion 80'. For purposes of clarity, bearing member 82' has not been shown in cross section in FIG. 5. Bearing member 82' includes spherical bearing surfaces 84' which are adapted to engage the spherically-shaped bearing portions 66' of the condyle portions 60'. The pair of bearing surfaces 84' collectively form a second bearing surface that mates with the first bearing surface. Bearing member 82' also includes a raised portion 160 which is adjacent the spherical bearing surfaces 84' and configured to clear pin portion 62', preferably without transmitting load therebetween (i.e., pin portion 62' preferably does not contact the surfaces of raised portion 160). In the particular embodiment illustrated, bearing member 82' is fabricated from polyethylene which has been molded to cage portion 80. Alternatively, bearing member 82' may be fabricated from any other appropriate material such as a cobalt chromium alloy, ceramics, or stainless steel.

To use unlinked prosthetic joint 10', first stem structure 12 is implanted in humerus 38' such that proximal portion 34 is located in the medullary canal 36' as shown in FIG. 5. Second stem structure 14 is similarly implanted in ulna 54' such that distal portion 50 is located in the medullary canal 52'. First bearing component 16' is next positioned adjacent the distal portion 32 of first stem structure 12 and furcations 42 are engaged to slotted apertures 68. Fasteners 64 are inserted through their respective mounting apertures 72 and threadably engaged to their threaded fastener aperture 44. When fully seated, each of the fasteners 64, extends through its respective furcation 42 to prevent its associated condyle portion 60' from rotating relative to thereto. The proximal end of the ulna 54' is positioned adjacent the distal end of the humerus 38' such that the pin portion 62' is proximate the raised portion 160 and the spherically-shaped bearing portions 66' of the condyle portions 60' engage the spherical bearing surface 84'. At this point, first and second bearing components 16' and 18' are coupled together in an unconstrained or unlinked manner (i.e., held in position by the soft tissues of the elbow). Construction of unlinked prosthetic joint 10' in this manner provides many of the same advantages as mentioned above for linked prosthetic joint 10, such as the ability of first and second bearing surfaces 16' and 18' to spread out the load that is transmitted through unlinked prosthetic joint 10' over a relatively large area, rather than concentrate the load at a single point or over a line of contact to thereby improve the durability of unlinked prosthetic joint 10'.

As a surgeon may not always know prior to beginning an operation whether a patient would be better served by a linked or an unlinked joint prosthesis and as it is also occasionally necessary to convert an unlinked joint prosthesis to a constrained joint prosthesis, or vice versa, after implementation and use for a period of time, it is highly desirable that the joint prosthesis be modular so as to provide the surgeon with a high degree of flexibility which may be achieved in a relatively simple and cost-effective manner.

Figure 6:
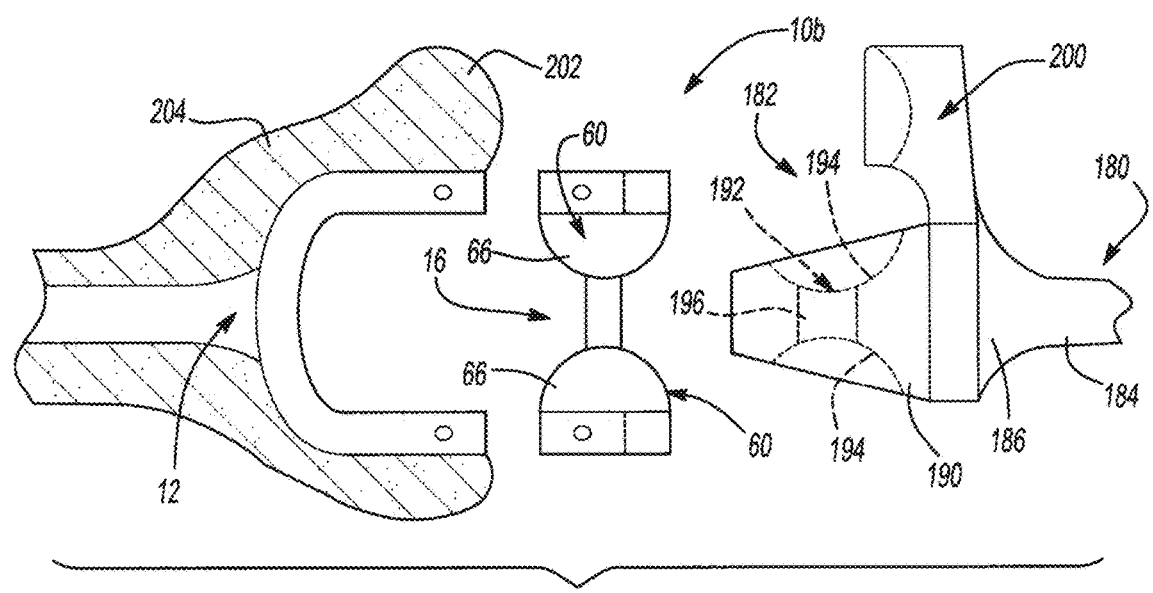
FIG. 6 is an exploded plan view of a linked prosthetic joint kit constructed in accordance with a second alternate embodiment of the first aspect of the present teachings.
Figure 7:
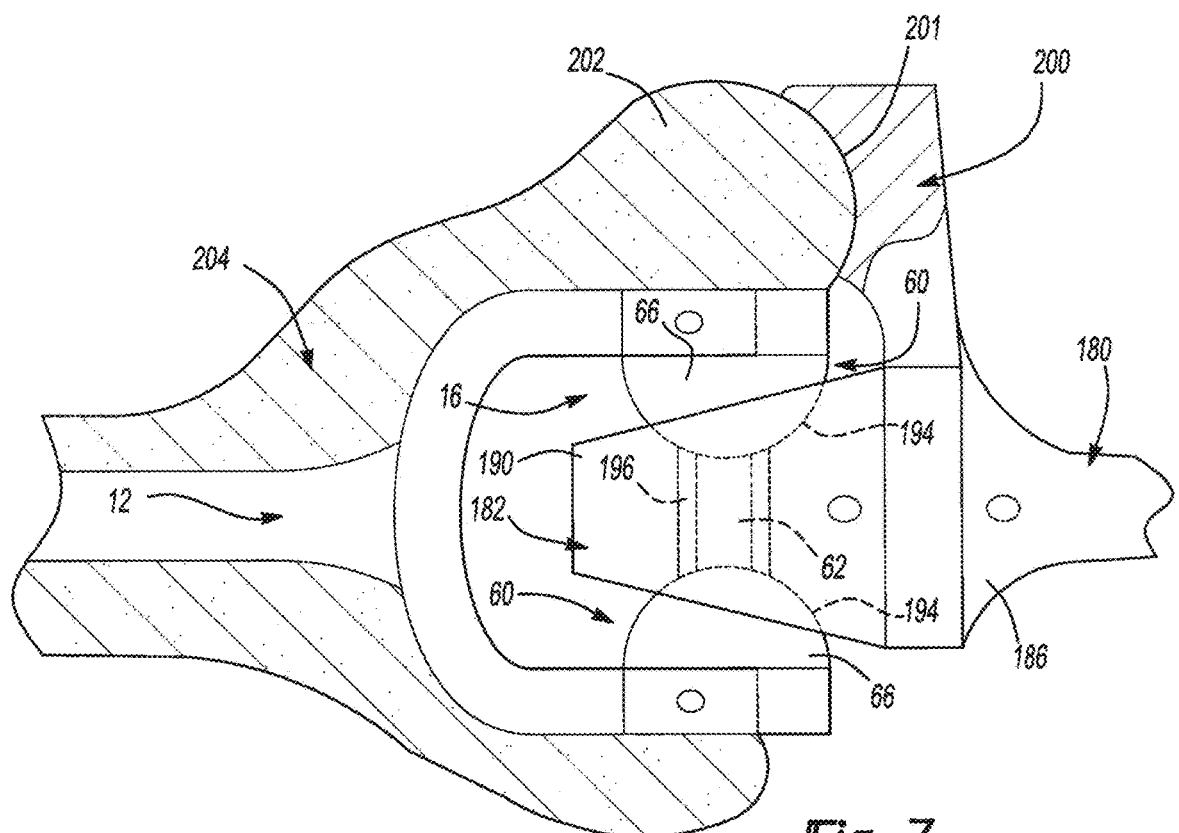
FIG. 7 is an enlarged portion of the linked prosthetic joint kit of FIG. 6.

In FIGS. 6 and 7, a linked prosthetic joint constructed in accordance with a second aspect of the present teachings is generally indicated by reference numeral 10b. Linked prosthetic joint 10b is shown to include first stem structure 12, a third stem structure 180, first bearing component 16, a third bearing component 182. Third stem structure 180 is similar to second stem structure 14 in that it includes a distal portion 184 which is adapted to fit within the medullary canal of an ulna. The proximal portion 186 of third stem structure 180 is coupled to third bearing component 182.

Third bearing component 182 is similar to second bearing component 18 in that it includes a cage portion 190 and a bearing member 192. Cage portion 190 is fixedly coupled to the proximal portion 186 of third stem structure 180. Bearing member 192 is fixedly coupled to cage portion 190. Bearing member 192 includes a pair of spherical bearing surfaces 194 which are configured to engage the spherically-shaped bearing portions 66 of the condyle portions 60 and a through hole 196 which is configured to receive pin portion 62, preferably without transmitting load therebetween (i.e., pin portion 62 preferably does not contact the surfaces of through hole 196). Bearing member 182 also includes a lateral buttress 200. Lateral buttress 200 includes a supplementary bearing surface 201 which is configured for receiving a capitellum 202 of the humerus 204. In the particular embodiment illustrated, third bearing component 182 is fixedly coupled to third stem structure 180 and as such, the combination of the second stem structure 14 and second bearing component 18 is interchangeable with the combination of the third stem structure 180 and the third bearing component 182. However, those skilled in the art will understand that second and third bearing components 18 and 182 may also be releasably coupled to a stem structure, thereby eliminating the need for a third stem structure 180 which would otherwise be identical to second stem structure 14. Those skilled in the art will also understand that the lateral buttress may alternatively be coupled directly to the third stem structure 180, being either releasably attached thereto or integrally formed therewith.

Figure 8:
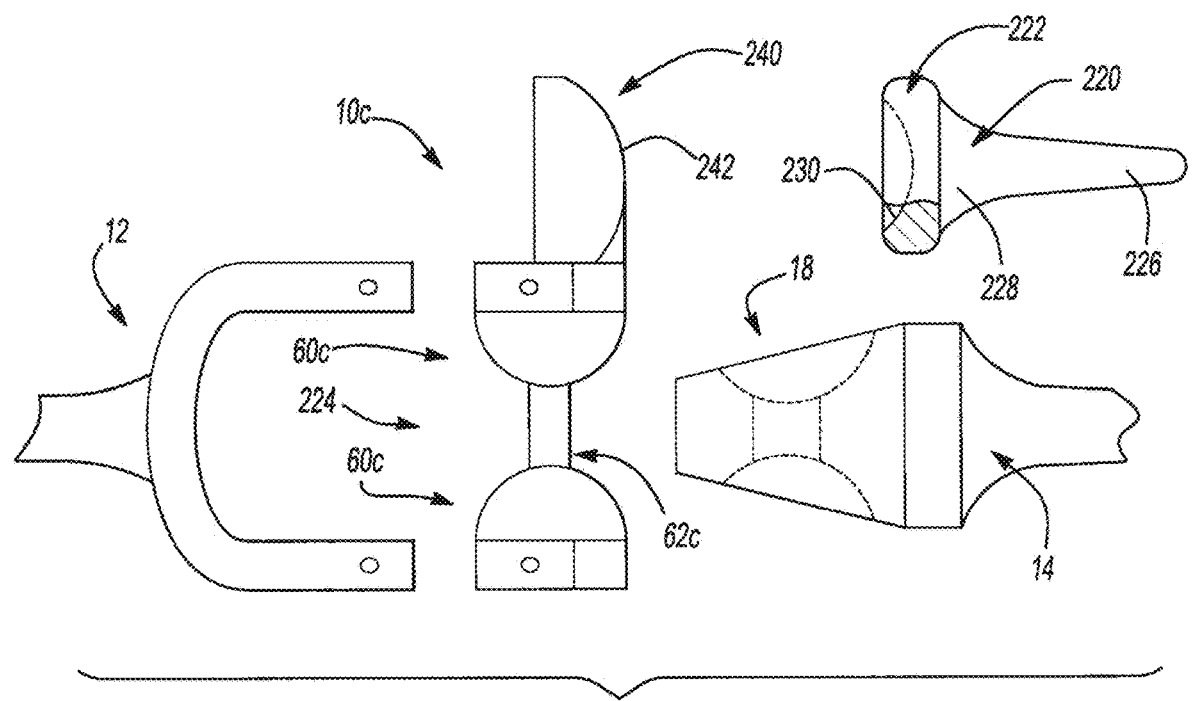
FIG. 8 is an exploded plan view of a linked prosthetic joint kit constructed in accordance with a third alternate embodiment of the first aspect of the present teachings.

In FIG. 8, another linked prosthetic joint constructed in accordance with the teachings of a second aspect of the present teachings is generally indicated by reference numeral 10c. Linked prosthetic joint 10c is shown to include first stem structure 12, second stem structure 14, a fourth stem structure 220, second bearing component 18, a fourth bearing component 222 and a fifth bearing component 224. Fourth stem structure 220 includes a distal end 226 which is adapted to fit within the medullary canal of a radius and a proximal end 228 which is fixedly coupled to fourth bearing component 222. Fourth bearing component 222 includes a fourth bearing surface 230.

Fifth bearing component 224 is similar to first bearing component 16 in that it includes, for example, a pair of condyle portions 60 and a pin portion 62 which permits first and fifth bearing components 16 and 224 to be interchangeable. However, fifth bearing component 224 also includes a lateral extension 240 which is adapted to replace at least a portion of the capitellum of the humerus. Lateral extension 240 defines a fifth bearing surface 242 which is configured to mate with fourth bearing surface 230. Preferably, at least a portion of each of the fourth and fifth bearing surfaces 230 and 242 is spherically shaped to permit loads transmitted therebetween to be spread out over a relatively large area, rather than be concentrated at a single point or along a line of contact.

Figure 9:
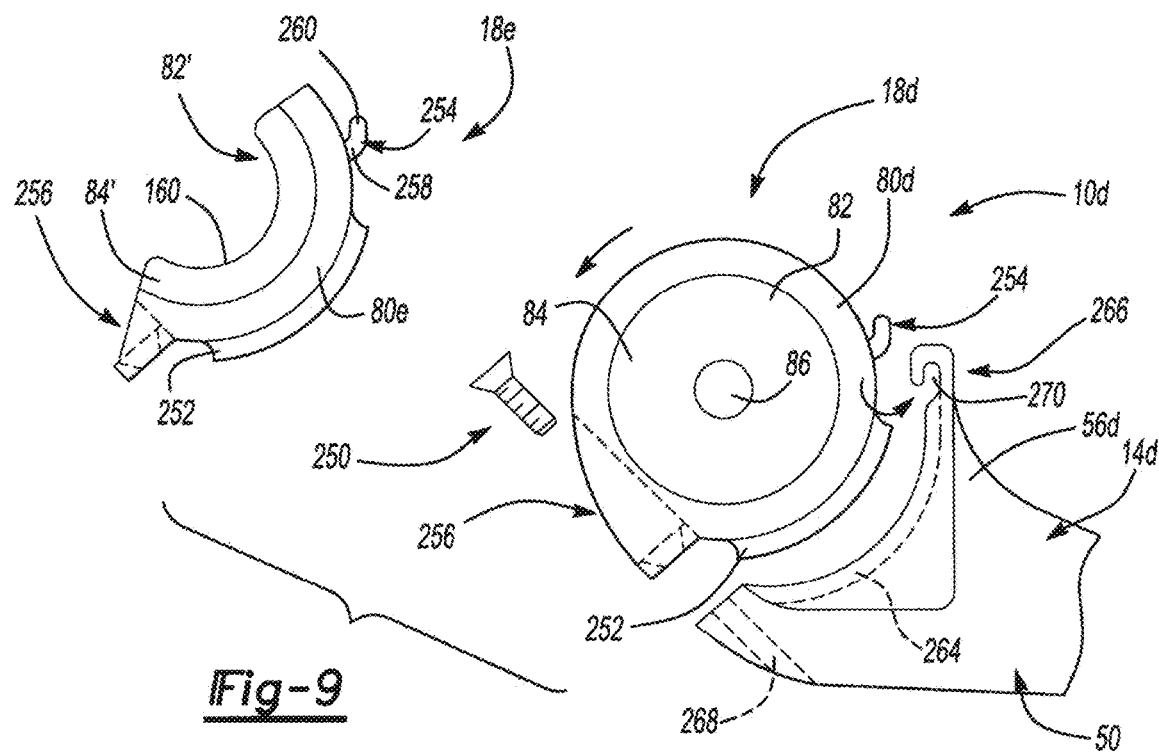
FIG. 9 is a exploded side elevation view of a portion of a joint kit constructed in accordance with the teachings of a second aspect of the present teachings.

In FIG. 9, a portion of a modular prosthetic joint kit constructed in accordance with the teachings of a second aspect of the present teachings is generally indicated by reference numeral 10d. Modular prosthetic joint kit 10d is shown to include second stem structure 14d, second bearing component 18d, second bearing component 18e and a fastener 250.

Second bearing components 18d and 18e are similar to second bearing components 18 and 18', respectively, but are shown to be separable from second stem structure 14d. Second bearing components 18d and 18e also include a keel member 252, a clip member 254 and a fastener aperture 256 which are formed in cage portions 80d and 80e, respectively. Keel member 252 extends circumferentially around at least a portion of the perimeter of each of the cage portions 80d and 80e between clip member 254 and fastener aperture 256. Clip member 254 includes a first portion 258 which extends generally perpendicularly outward from its associated cage portion and a second portion 260 which is coupled to the distal end of first portion 258. Second portion 260 extends generally outwardly and away from first portion 258. Fastener aperture 256 is located across from clip member 254 and is sized to receive fastener 250.

Second stem structure 14d is similar to second stem structure 14 in that it includes a distal end 50 which is adapted to fit within the medullary canal of an ulna. Second stem structure 14d also includes a proximal portion 56d having a keel slot 264, a hook structure 266 and an internally threaded fastener aperture 268. Keel slot 264 is a slot that is sized to receive keel member 252 in a slip fit manner. Keel slot 264 and keel member 252 cooperate to resist relative medial/lateral motion of cage portion (e.g. 80d) relative to second stem structure 14d. Hook member 266 is generally U-shaped and defines a clip aperture 270 which is sized to receive clip member 254.

To use modular prosthetic joint kit 10d, the distal end 50 of second stem structure 14d is inserted in the medullary canal of the ulna. The modularity of the prosthetic joint kit 10d permits the surgeon to assess the patient's elbow to determine if the patient would be better served by a linked or an unlinked joint prosthesis. Once a decision has been made as to which type of joint prosthesis would better serve the patient, the surgeon selects an appropriate one of the second bearing components 18d and 18e, places its clip member 254 into the clip aperture 270, pivots the cage portion (i.e. 80d) toward the proximal end 56d of the second stem structure 14d to engage the keel member 252 into the keel slot 264, inserts the fastener 250 through the fastener aperture 256 and threadably engages the fastener 250 to the internally threaded fastener aperture 268 to fixedly but releasably couple the second stem structure 14d with the selected one of the second bearing components 18d and 18e.

Figure 10:
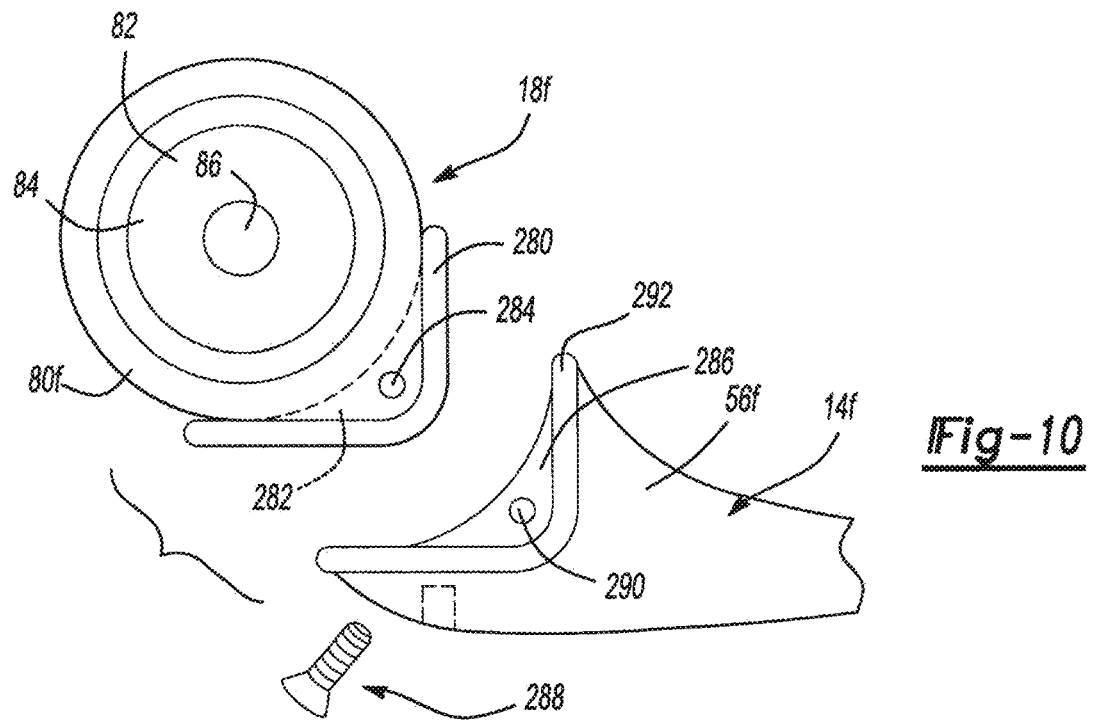
FIG. 10 is an exploded side elevation view of a portion of a joint kit constructed in accordance with a first alternate embodiment of the second aspect of the present teachings.

Those skilled in the art will understand that second bearing components 18d and 18e may be coupled to second stem structure 14d in various other manners as illustrated in FIGS. 10 through 15. In FIG. 10, second bearing component 18f is shown to include a generally L-shaped tray portion 280 which is fixedly coupled to cage portion 80f. Tray portion 280 includes a keel slot 282 and a fastener aperture 284. Keel slot 282 is operable for receiving a keel member 286 formed into the proximal end 56f of second stem structure 14f. Fastener aperture 284 is operable for receiving a fastener 288 which may be threadably engaged to an internally-threaded fastener aperture 290 in the proximal end 56f of second stem structure 14f to thereby permit second bearing component 18f and second stem structure 14f to be fixedly but releasably coupled.

When coupled together, keel slot 282 and keel member 286 cooperate to resist relative medial/lateral motion of cage portion 80f relative to second stem structure 14f. Additionally, tray portion 280 cooperates with an L-shaped flange 292 to which it abuts to further resist relative rotation between second stem structure 14f and cage portion 80f.

Figure 11:
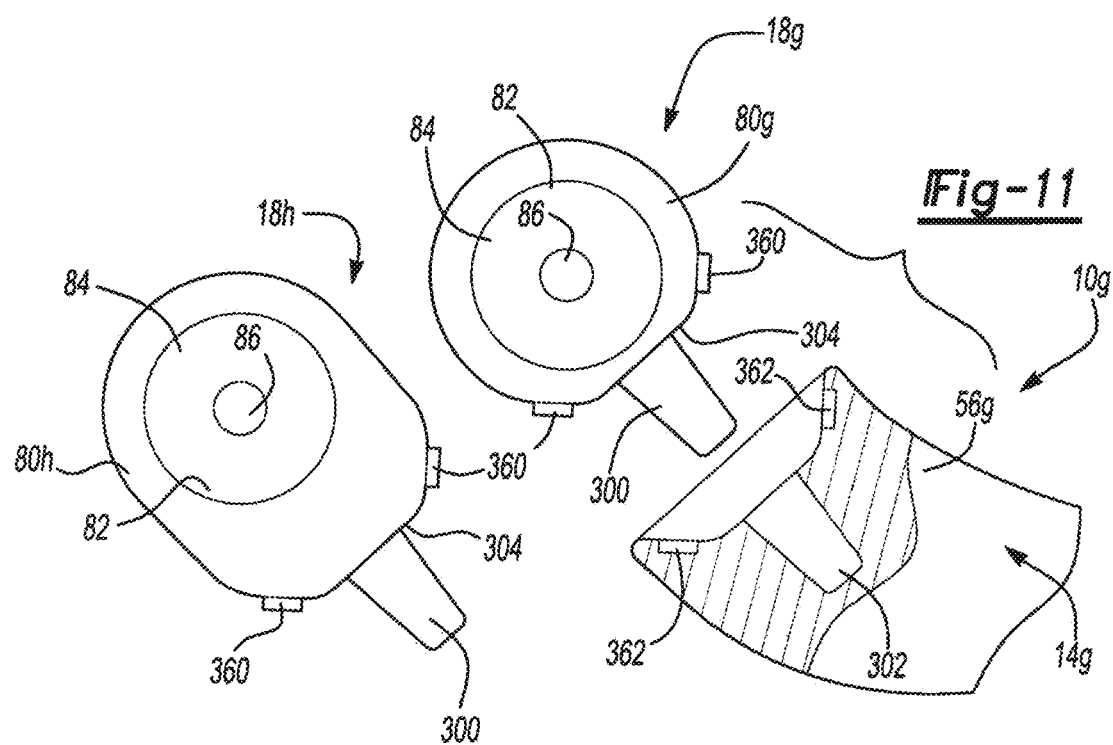
FIG. 11 is an exploded side elevation view of a portion of a joint kit constructed in accordance with a third alternate embodiment of the second aspect of the present teachings.
Figure 12:
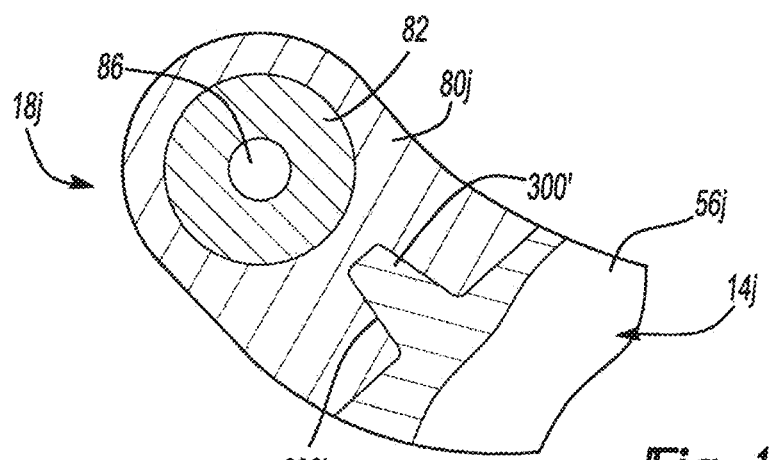
FIG. 12 is a longitudinal cross-sectional view of a portion of a joint kit constructed in accordance with a fourth alternate embodiment of the second aspect of the present teachings.

In FIG. 11, second bearing components 18g and 18h are shown to include a stem member 300 which extends from their respective cage portions 80g and 80h. Stem member 300 is engageable with a stem aperture 302 formed into the proximal end 56g of second stem structure 14g. As shown in FIG. 12, stem member 300' may alternatively be incorporated into the proximal end 56j of second stem structure 14j and stem aperture 302' may be formed into cage portion 80j of second bearing component 18j.

To provide the surgeon with additional flexibility, second bearing component 18h is shown in FIG. 11 to be slightly longer than second bearing component 18g (i.e., the distances from the centerline of bearing member 82 to the confronting surface 304 of their respective cage portions 80g and 80h is shorter for second bearing component 18g). This variation between second bearing components 18g and 18h permits the surgeon to adjust the length of prosthesis 10g to take into account the physical characteristics of the patient's arm.

Figure 13:
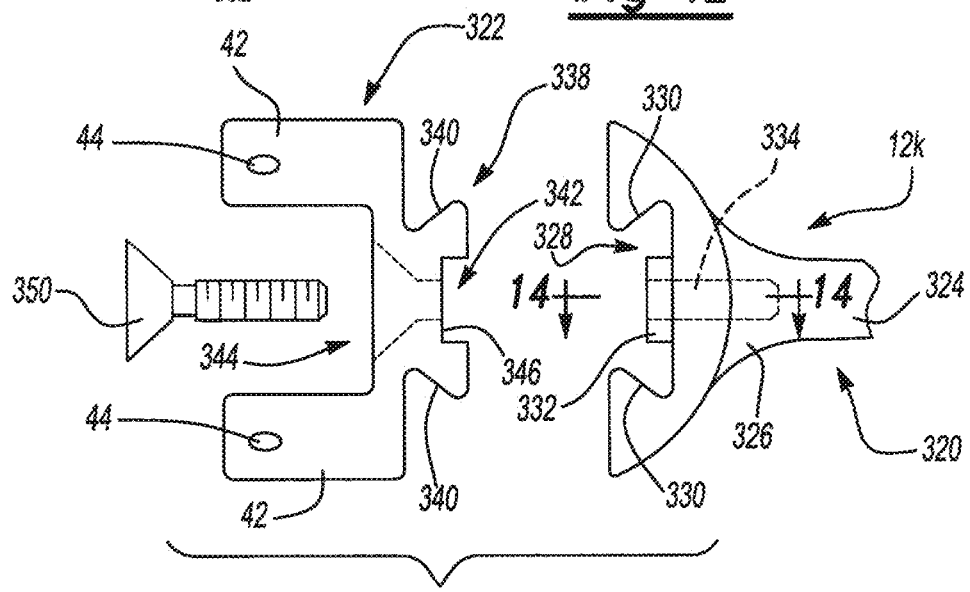
FIG. 13 is an exploded side elevation view of a portion of a joint kit constructed in accordance with a fifth alternate embodiment of the second aspect of the present teachings.
Figure 14:
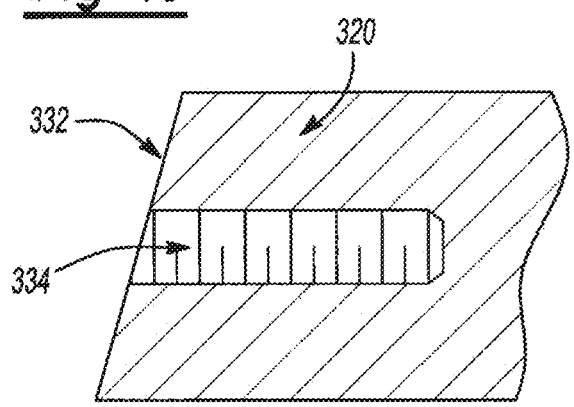
FIG. 14 is a cross-sectional view taken along the line 14-14 of FIG. 13.

Modularity may also be incorporated into first stem structure 12k as shown in FIGS. 13 and 14. First stem structure 12k is shown to include a stem member 320 and a yoke member 322. The proximal end 324 of stem member 320 is adapted to fit within the medullary canal of a humerus and the distal end 326 of stem member 320 terminates at a dovetail aperture 328 having a pair of inwardly tapering walls 330 and a tapered retaining wedge 332. An internally threaded fastener aperture 334 extends through retaining wedge 332. Yoke member 322 is shown to be similar to the distal end 32 of first stem structure 12 as it includes furcations 42 and threaded fastener apertures 44. Yoke member 322 also includes a dovetail member 338 having a pair of outwardly tapering surfaces 340, a wedge slot 342 and a through hole 344. Dovetail member 338 is configured to mate with dovetail aperture 328 such that engagement of retaining wedge 332 to the upper surface 346 of wedge slot 342 forces tapered surfaces 340 against a respective one of the inwardly tapering walls 330. A fastener 350 is inserted through hole 344 and threadably engaged to internally threaded fastener aperture 334 to fixedly but releasably couple yoke member 322 and stem member 320 together.

Referring back to FIG. 11, second bearing components 18g and 18h are also shown to include a pair of tang members 360. Each of the tang members 360 extends outwardly from its respective cage portion (i.e., 80g) and in the particular embodiment illustrated, is generally rectangular in shape. Each of the tang members 360 is sized to engage a tang recess 362 in the proximal end 56g of the second stem structure 14g. Engagement of the tang members 360 into their respective tang recess 362 inhibits relative rotation between the second stem structure 14g and the second bearing components 18g and 18h.

Figure 15:
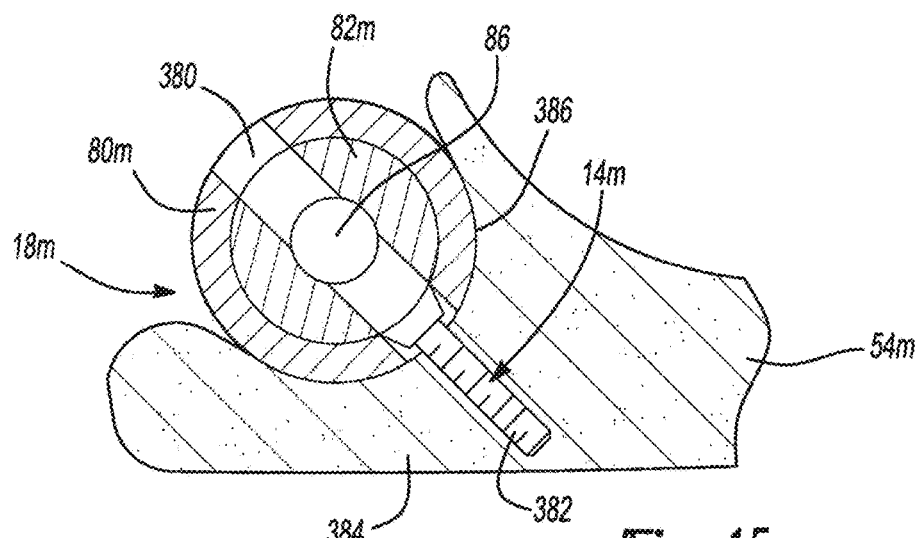
FIG. 15 is a cross-sectional view of a portion of a joint kit constructed in accordance with a sixth alternate embodiment of the second aspect of the present teachings.

In FIG. 15, second bearing component 18m is shown to have a fastener aperture 380 which is formed through a bearing member 82m and cage portion 80m. Second stem structure 14m, which is a threaded fastener 382 in this embodiment, is disposed through the fastener aperture 380 in second bearing component 18m and threadably engaged to the cancellous bone 384 of the ulna 54m. Construction in this manner is advantageous in that it permits the extent of the trauma experienced by the patient to be minimized. To further this goal, the distal end 386 of cage portion 80m is shown to be generally cylindrically shaped so as to minimize the amount of bone that must be removed to prepare the ulna 54m for the second bearing component 18m.

Figure 16:
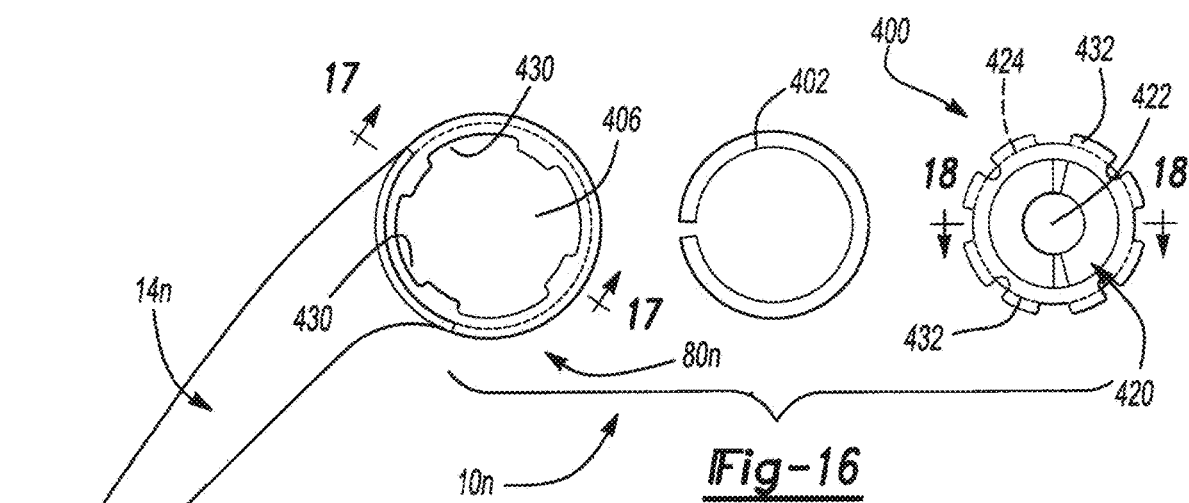
FIG. 16 is an exploded side elevation view of a portion of linked prosthetic joint kit constructed in accordance with the teachings of various embodiments of a third aspect of the present teachings.
Figure 17:
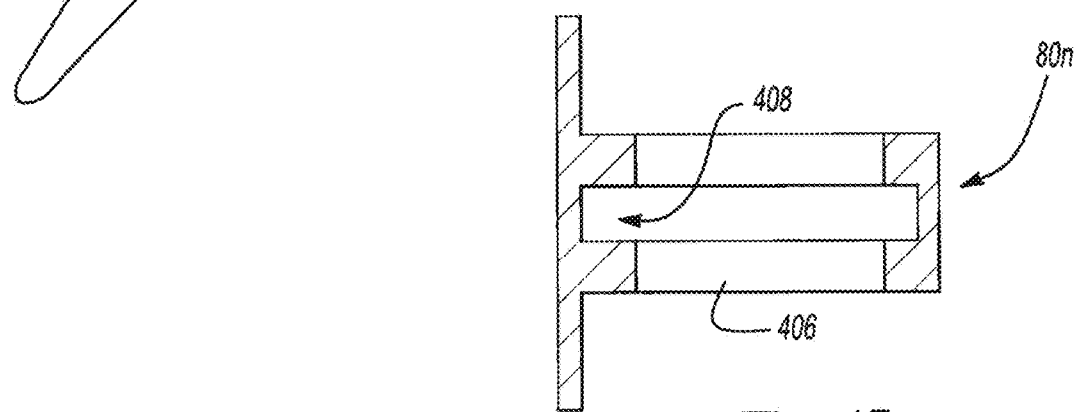
FIG. 17 is a cross-sectional view taken along the line 17-17 of FIG. 16.

In FIGS. 16 through 18, a portion of a modular prosthetic joint kit constructed in accordance with the teachings of a third aspect of the present teachings is generally indicated by reference numeral 10n. Modular prosthetic joint kit 10n is shown to include a bearing insert 400, a retaining ring 402 and a second stem structure 14n having an integrally attached cage portion 80n. Cage portion 80n is shown to include a bearing aperture 406 for receiving bearing insert 400. In the particular embodiment illustrated, cage portion 80n also includes a circumferentially extending first ring groove 408 formed along the perimeter of bearing aperture 406 and operable for receiving a first portion of retaining ring 402.

Bearing insert 400 is generally cylindrically shaped, having a pair of spherical depressions 420 which collectively form a bearing surface that is configured to mate with the spherically-shaped bearing portions 66 of the first bearing component 16. Bearing insert 400 also includes a through hole 422 which is adapted to receive pin portion 62, preferably without transmitting load therebetween. A circumferentially extending second ring groove 424 is formed in the outer perimeter of bearing insert 400, the second ring groove 424 being operable for receiving a second portion of retaining ring 402. Construction in this manner is advantageous in that the surgeon may select a bearing insert 400 from a plurality of bearing inserts 400 to adapt prosthetic joint 10n to the patient.

In the particular embodiment illustrated, bearing aperture 406 is shown to include a plurality of radially outwardly extending tab apertures 430 and bearing insert 400 is shown to include a plurality of radially outwardly extending tabs 432. If desired, a first one of the tab apertures 430 and a first one of the tabs 432 may be sized differently than the remaining tab apertures 430 and tabs 432, respectively, to key the bearing insert 400 to a specific orientation relative to second stem structure 14n.

With specific reference to FIG. 18, each of the pair of spherical depressions 420 includes a first spherical portion 450 and a second spherical portion 454. Each of the first spherical portions 450 are formed into bearing insert 400 along an axis 456 that is coincident with the longitudinal centerline of the bearing insert 400. Each of the first spherical portions 450 are formed by a spherical radius approximately equal in magnitude to the spherical radius which defines the spherically-shaped bearing portion 66 of each of the condyle portions 60 of first bearing component 16. The distance between the spherical radii along axis 456 is equal to a predetermined distance, d.

The centerpoint 456 of the spherical radius that defines one of the first spherical portions 450 is employed to generate the second spherical portion 454 on the opposite face of the bearing surface. A second centerline 468 is constructed from centerpoint 460 toward the opposite face at a predetermined constraint angle 470, such as 3.5 degrees. The spherical radius that defines the second spherical portion 454 on the opposite face is generated from a second centerpoint 472 which is positioned along the second centerline 468 at a distance d from centerpoint 460. Construction of bearing insert 400 in this manner permits first bearing component 16 to rotate about centerline 456, as well as to pivot relative to bearing insert 400 about the spherically-shaped bearing portion 66 of each of the condyle portions 60.

A transition zone 480 is formed between each of the first and second spherical portions 450 and 454 wherein a radius is formed at the intersection of the radii which define the first and second spherical portions 450 and 454 to "soften" the transition between the first and second spherical portions 450 and 454 to render the movement of the condyle portions 60 over the first and second spherical portions 450 and 454 more comfortable to the patient.

Those skilled in the art will understand that the degree of the constraint may be defined by the constraint angle. Accordingly, modular prosthetic joint kit 10n preferably includes a plurality of bearing inserts 400, each having a bearing surface with a second spherical portion 454 that is defined by a different constraint angle. Those skilled in the art will also understand that the degree of the constraint may be additionally or alternatively defined by a constraint characteristic, which is illustrated in FIGS. 19A through 19D.

Figure 19C:
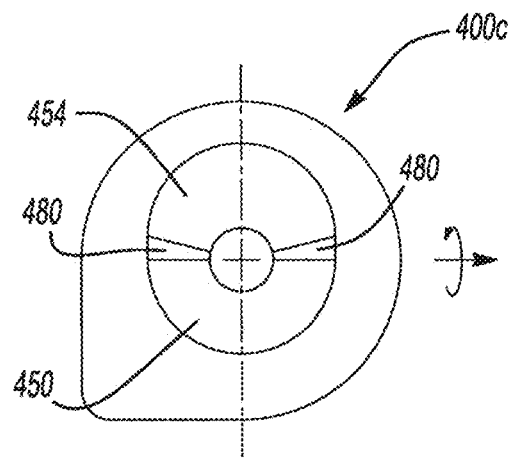
Figure 19D:
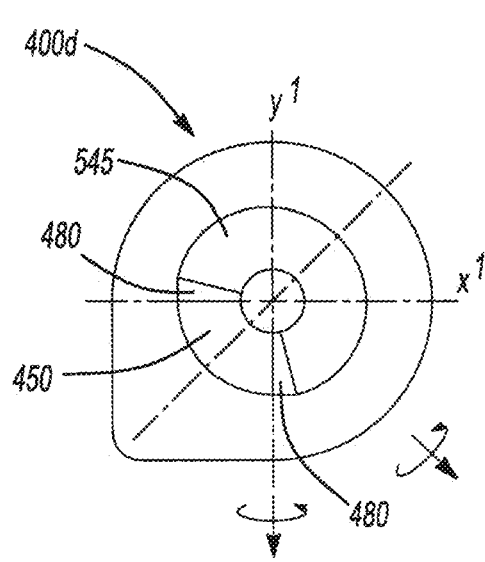

In FIG. 19A, bearing insert 400a has a first predetermined constraint characteristic orientation wherein the centerlines which define the radii which define first and second spherical portions 450 and 454 are contained in a plane which is generally perpendicular to the longitudinal axis of the ulna. Construction of bearing insert 400a in this manner provides a varying degree of axial constraint. In FIG. 19B, bearing insert 400b has a second predetermined constraint characteristic wherein the centerlines which define the radii which define first and second spherical portions 450 and 454 are contained in a plane which is at approximately 45° to the longitudinal axis of the ulna. Construction of bearing insert 400b in this manner provides a varying degree of a combination of axial and varus/valgus constraint. In FIG. 19C, bearing insert 400c has a third predetermined constraint characteristic wherein the centerlines which define the radii which define first and second spherical portions 450 and 454 are contained in a plane which is generally parallel the longitudinal axis of the ulna. Construction of bearing insert 400c in this manner provides a varying degree of varus/valgus constraint. In FIG. 19D, bearing insert 400d is constructed in a manner that is generally similar to that of bearing inserts 400a, 400b and 400c except that the constraint angle employed to construct bearing insert 400d is rotated form point x1 to y1 as indicated in FIG. 19d. As a result, there is no single line of orientation in which the constraint is limited. Construction of bearing insert 400d in this manner provides a varying degree of constraint in both an axial direction and a varus/valgus direction.

In FIGS. 20A through 22, a portion of a modular prosthetic joint kit constructed in accordance with the teachings of an alternate embodiment of the third aspect of the present teachings is generally indicated by reference numeral 10p. Modular prosthetic joint kit 10p is similar to modular prosthetic joint kit 10n in that it includes a bearing insert 400p and a second stem structure 14p having a integrally attached cage portion 80p.

Cage portion 80p is shown to include a bearing aperture 406p for receiving bearing insert 400p. In the particular embodiment illustrated, cage portion 80p includes a plurality of tab apertures 430p, a plurality of tab slots 500 and a hook structure 502. Each of the tab apertures 430p extends axially through cage portion 80p and circumferentially around a portion of bearing aperture 406p. Each of the tab slots 500 intersects one of the tab apertures 430p and extends circumferentially around a portion of bearing aperture 406p away from its associated tab aperture 430p. Hook structure 502 is adjacent one of the tab apertures 430p and extends radially inwardly and circumferentially around a portion of bearing aperture 406p. A clip slot 510 is formed circumferentially through hook structure 502.

Bearing insert 400p is generally similar to bearing insert 400 except for the configuration of the plurality of tabs 432p and the incorporation of a clip structure 520 into a bearing body 522. Each of the plurality of tabs 432p is relatively thin and do not extend axially across bearing insert 400p. This permits the tabs 432p of bearing insert 400p to be aligned to a tab aperture 430p and bearing insert 400p to be rotated so that each of the tabs 432p is disposed within one of the tab slots 500 to thereby prevent bearing insert 400p from moving in an axial direction.

Clip structure 520 is preferably a metal or plastic fabrication which is suitable for molding into bearing body 522. Clip structure 520 includes an arm structure 530 which extends from a clip body 532 and terminates at its distal end at a hook member 534. Clip structure 520 is configured and incorporated into bearing body 522 such when bearing insert 400p is rotated to engage tabs 432p into tab slots 500, arm structure 530 simultaneously engages clip slot 510 in hook structure 502. Rotation of bearing insert 400p to a predetermined rotational position relative to hook structure 502 permits hook member 534 to engage an edge 540 of hook structure 502. Arm structure 530 resiliently biases hook member 534 against edge 540, thereby inhibiting rotation of bearing insert 400p which would cause tabs 432p to disengage tab slots 500.

Figure 20A:
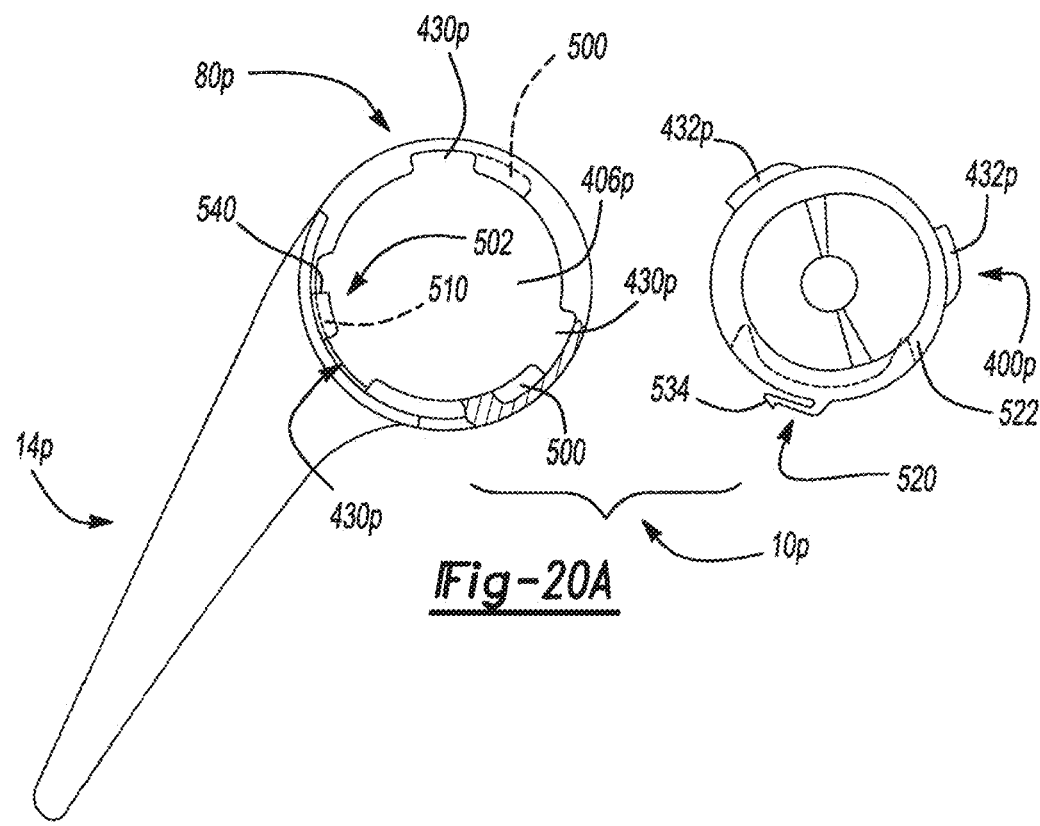
FIG. 20A is an exploded side elevation view of a portion of a linked prosthetic joint kit constructed in accordance with the teachings of a first alternate embodiment of the third aspect of the present teachings.
Figure 20B:
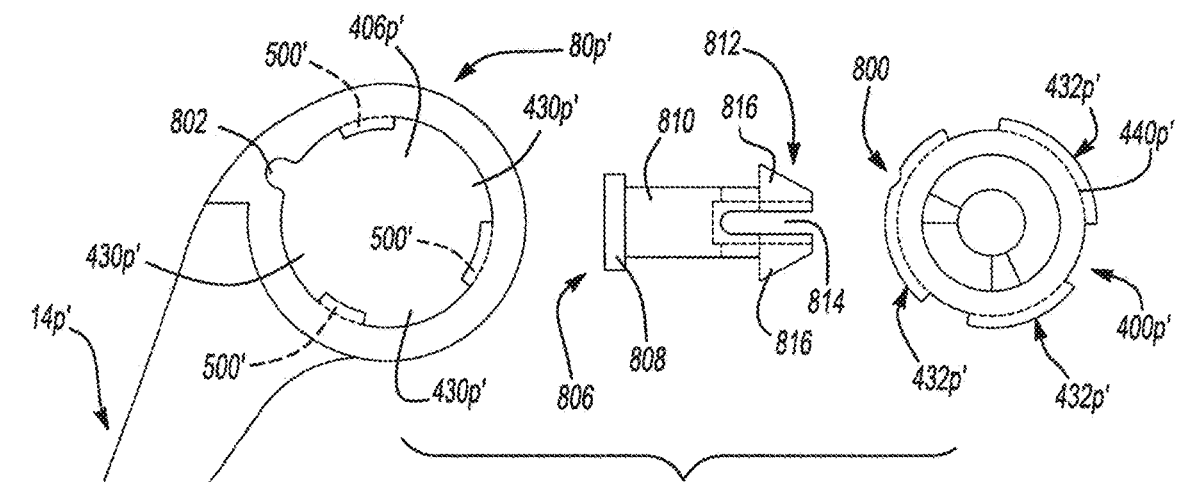
FIG. 20B is an exploded side elevation view of a portion of a linked prosthetic joint constructed in accordance with the teachings of second alternate embodiment of the third aspect of the present teachings.

In FIG. 20B, bearing insert 400p' is illustrated to be configured similarly to bearing insert 400p except that a locking aperture 800 is formed into one of the tabs 432p'. Bearing insert 400p' is inserted into bearing aperture 406p' aligned such that each of the tabs 432p' is aligned to an associated one of the tab apertures 430p'. Bearing insert 400p' is then rotated so that each of the tabs 500' is disposed within one of the tab slots 440p' and locking aperture 800 is aligned to a corresponding locking aperture 802 formed in the integrally attached cage portion 80p' of second stem structure 14p'. Engagement of tabs 500' into their respective tab slots 440p' prevents bearing insert 400p' from moving in an axial direction. Alignment of locking apertures 800 and 802 to one another permits a pin 806 to be inserted therethrough to prevent bearing insert 400p' from rotating relative to integrally attached cage portion 80p'. In the particular embodiment illustrated, pin 806 includes a head portion 808, a body portion 810 and an end portion 812. Head portion 808 has a diameter which is larger than the diameter of the hole formed by locking apertures 800 and 802. Body portion 810 is preferably smaller in diameter than the diameter of the hole formed by locking apertures 800 and 802.

A plurality of slots 814 are formed in end portion 812 which creates a plurality of fingers 816 which are flexible relative to the longitudinal axis of pin 806. Fingers 816 flex inwardly toward the longitudinal axis of pin 806 when pin 806 is inserted to locking apertures 800 and 802, eliminating the interference therebetween to permit the fingers 816 of end portion 812 to pass through integrally attached cage portion 80p' and bearing insert 400p'. Once the fingers 816 have passed through integrally attached cage portion 80p' and bearing insert 400p', they flex outwardly away from the longitudinal axis of pin 806 to inhibit the unintended withdrawal of pin 806 from locking apertures 800 and 802. Intended withdrawal of pin 806 from locking apertures 800 and 802 may be effected through the flexing of fingers 816 inwardly toward the longitudinal axis of pin 806.

Figures 20C, 21:
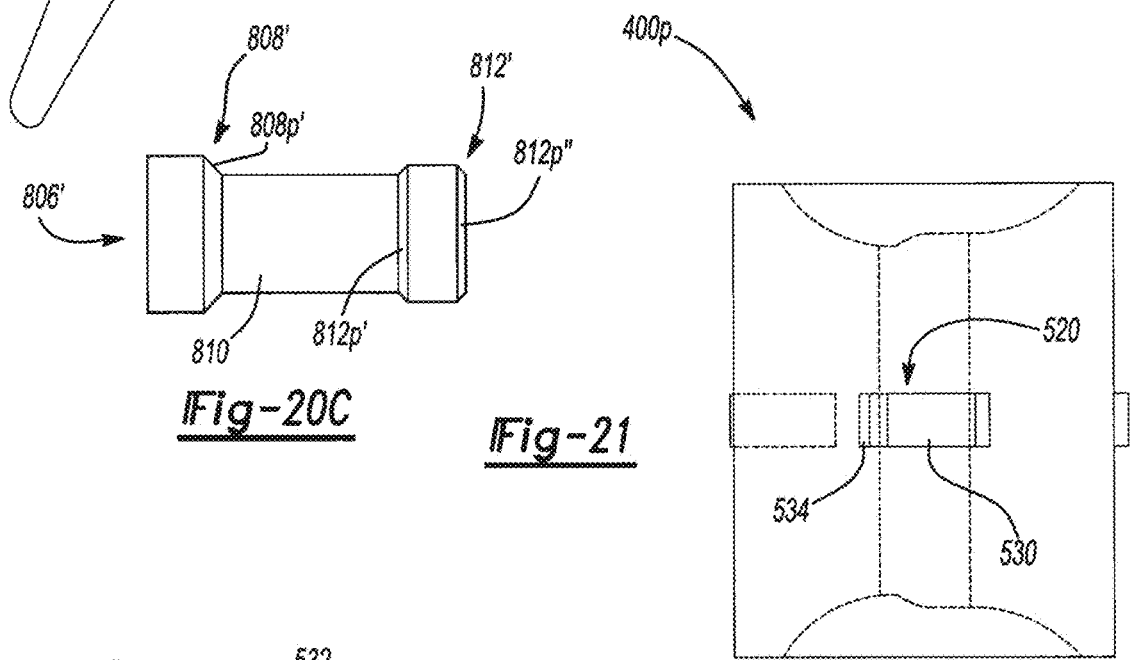
FIG. 20C is a side view of an alternately constructed pin for linking the stem structures of the second alternate embodiment of the third aspect of the present teachings.
FIG. 21 is a bottom plan view of a portion of the linked prosthetic joint kit of FIG. 20A illustrating the bearing insert in greater detail.
Figure 22:
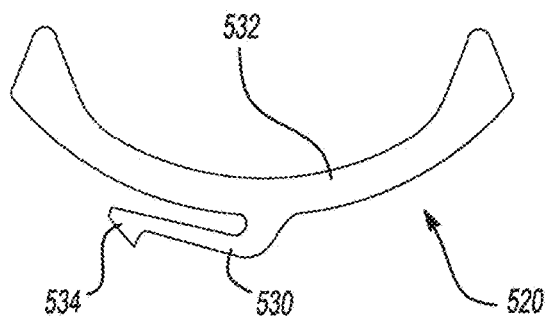
FIG. 22 is a side elevation view of a portion of the linked prosthetic joint kit of FIG. 20A illustrating the clip member in greater detail.

Those skilled in the art will understand, however, that the pin 806 for linking first and second stem structures 12 and 14p' may be constructed differently. As shown in FIG. 20C, for example, the pin 806' includes head and end portions 808' and 812' having chamfered abutting surfaces 808p' and 812p', respectively. The chamfered abutting surfaces 808p' and 812p' can abut the locking apertures 800 and 802, similar to the pin 806. As illustrated, the pin 806 in FIG. 20B includes the head portion 808 that is larger than the locking apertures 800 and 802 and the end portion 812 that can flex so that it can be smaller than the locking apertures 800 and 802 to allow passage of at least a portion of the pin 806 through the locking apertures 800, 802. One skilled in the art will understand that a locking pin can generally pass through an aperture and be held therein, through some mechanism, to allow for interconnection or locking of the various portions relative to one another. Nevertheless, the chamfered abutting surfaces 800p' and 812p' can allow for a selected engagement of a pin 806' between the locking apertures 800, 802. Additionally, the end portion 812' includes a chamfered lead portion 812p'''. The chamfered lead portion 812p''' can assist in allowing the pin 806' to be passed through the locking apertures 800, 802. Although it will be understood that the end portion 808' can be larger than the locking apertures 800, 802 so that the pin can only pass a selected distance through the locking apertures and be held relative to the cage portion 80p' and the bearing insert 400p'. As discussed above, in relation to the locking pin 806, the leading end 812 can be allowed to pass through the locking apertures 800, 802, allowing the legs 816 to flex such that the head 812 passes through the locking apertures 800, 802, similar to the head portion 812' which is configured with the chamfered lead portion 812p''' to allow for the pin 806 to pass through the locking aperture 800, 802. However, the end portion 808' is sized to not pass through the locking aperture 800, 802 so that the pin 806' can be held in a selected location. Pin 806' is installed by simply pressing it through the bearing insert 400p'.

Figure 23:
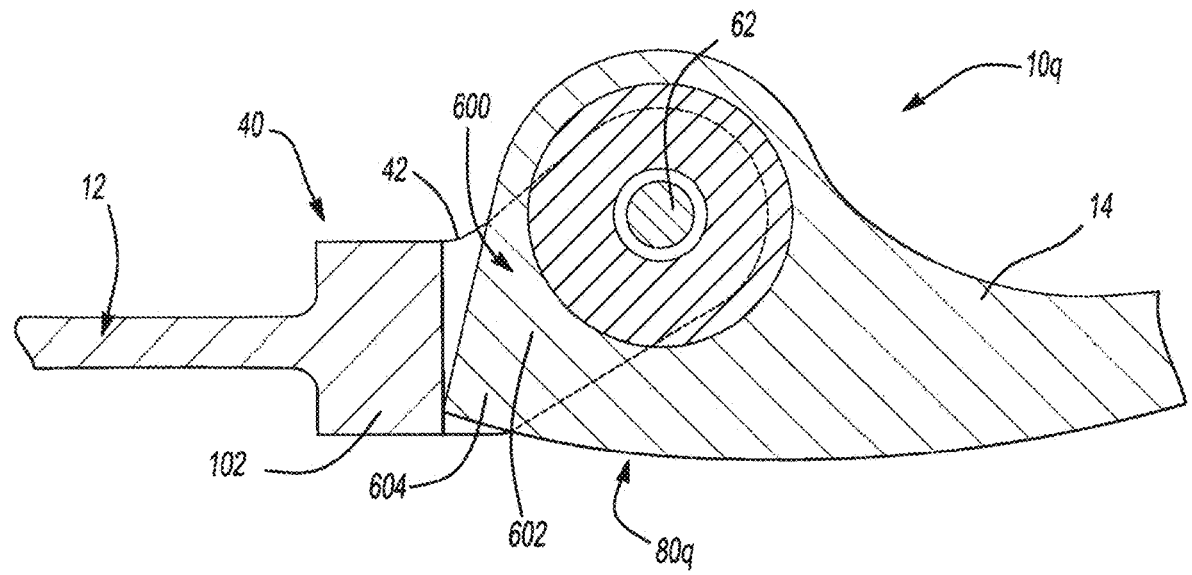
FIG. 23 is a longitudinal cross-sectional view of a linked prosthetic joint kit constructed in accordance with the teachings of a various embodiment of a fourth aspect of the present teachings.
Figure 24:
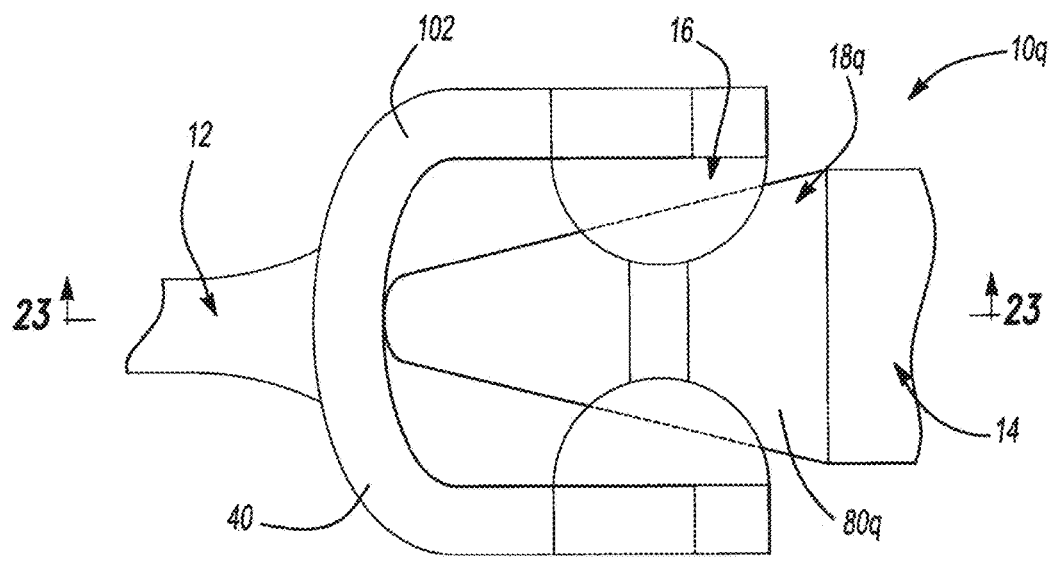
FIG. 24 is a top plan view of the linked prosthetic joint kit of FIG. 23.

In FIGS. 23 and 24, a portion of a modular prosthetic joint kit constructed in accordance with the teachings of a fourth aspect of the present teachings is generally indicated by reference numeral 10q. Prosthetic joint kit 10q is shown to include first stem structure 12, second stem structure 14, first bearing component 16 and second bearing component 18q. Second bearing component 18q is substantially similar to second bearing component 18 except that cage portion 80q is shown to include a cam structure 600. Cam structure 600 includes a lobe member 602 that extends radially outwardly and terminates at a tip 604. Lobe member 602 is configured such that tip 604 contacts the base 102 of U-shaped member 40 to inhibit further relative rotation between first and second stem structures 12 and 14 when the first and second stem structures 12 and 14 are placed in a position corresponding to the maximum extension of a patient's arm. Configuration of second bearing component 18$q$ in this manner is advantageous in that it limits the amount by which a patient may rotate their ulna relative to their humerus to prevent hyperextension of the joint.

Figure 25:
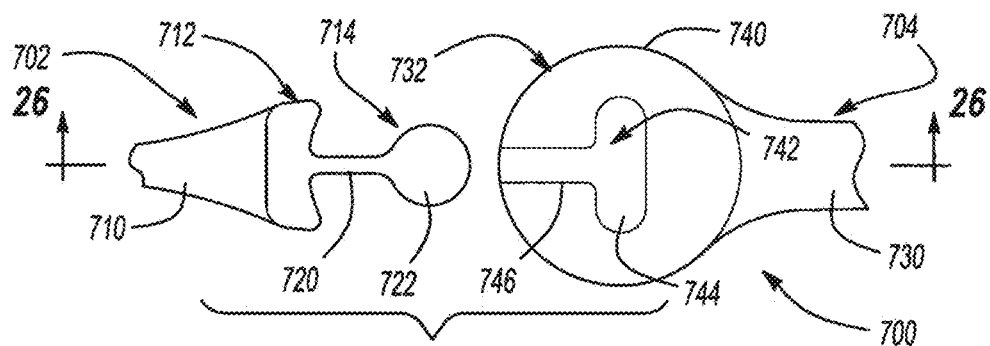
FIG. 25 is an exploded top plan view of a linked prosthetic joint kit constructed in accordance with the teachings of a various embodiment of a fifth aspect of the present teachings.
Figure 26:
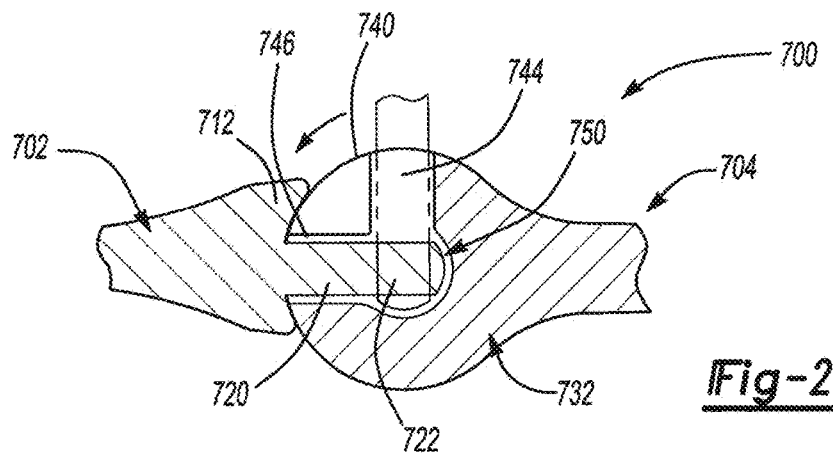
FIG. 26 is a longitudinal cross-sectional view of the linked prosthetic joint kit of FIG. 25.

In FIGS. 25 and 26, a portion of a modular prosthetic joint kit constructed in accordance with the teachings of a fifth aspect of the present teachings is generally indicated by reference numeral 700. Prosthetic joint kit 700 is shown to include a first stem structure 702 and a second stem structure 704. First stem structure 702 includes a stem member 710, the distal end of which is configured to fit within the medullary canal of an ulna. A first bearing 712 and a coupling structure 714 are incorporated into the proximal end of first stem structure 702. First bearing structure 712 is generally spherically shaped. Coupling structure 714 includes a link member 720 and a retainer member 722. Link member 720 is fixedly coupled to first bearing 712 at a first end and to retaining structure 722 at a second end with link member 720 extending therebetween along an axis generally coincident the longitudinal axis of first stem structure 702. Retaining structure 722 is illustrated to be spherically shaped with flattened ends.

Second stem structure 704 is shown to include a stem member 730 with a proximal end that is configured to fit within the medullary canal of a humerus. A second bearing structure 732 is incorporated into the distal end of second stem structure 704. Second bearing structure 732 includes a generally spherical second bearing surface 740 and a T-shaped coupling aperture 742. A first portion 744 of coupling aperture 742 has a width which is larger than the width of retaining structure 722. First portion 744 is oriented at a position of maximum flexion. In the particular embodiment illustrated, the position of maximum flexion is illustrated to be about 90° to the longitudinal axis of second stem structure 704. However, those skilled in the art will understand that the position of maximum flexion may be tailored in a desired manner and may range as high to an angle of approximately 135° to 150° to the longitudinal axis of second stem structure 704, depending on the particular application. A second portion 746 of coupling aperture 742 has a width which is slightly larger than that of link member 720. Second portion 746 extends circumferentially around a portion of second bearing surface 740 in a plane that coincides with the longitudinal axis of second stem structure 704. The first and second portions 744 and 746 of coupling aperture 742 intersect and terminate at spherically shaped cavity 750.

To use prosthetic joint kit 700, first and second stem structures 702 and 704 are inserted into the medullary canals of the ulna and humerus, respectively. First stem structure 702 is then positioned proximate the first portion 744 of coupling aperture 742 and retaining structure 722 is inserted through first portion 744 and into spherically shaped cavity 750. At this point, first and second bearing surfaces 712 and 740 are in contact with one another and transmit load therebetween rather than through coupling structure 714. Coupling of first and second stem structures 702 and 704 is complete when first stem structure 702 is rotated into second portion 746. In this position, first and second stem structures 702 and 704 are linked or constrained since the width of retaining portion 722 is larger than the width of second portion 746 and thereby prevents the withdrawal of first stem structure 702 from coupling aperture 742.

Figure 27:
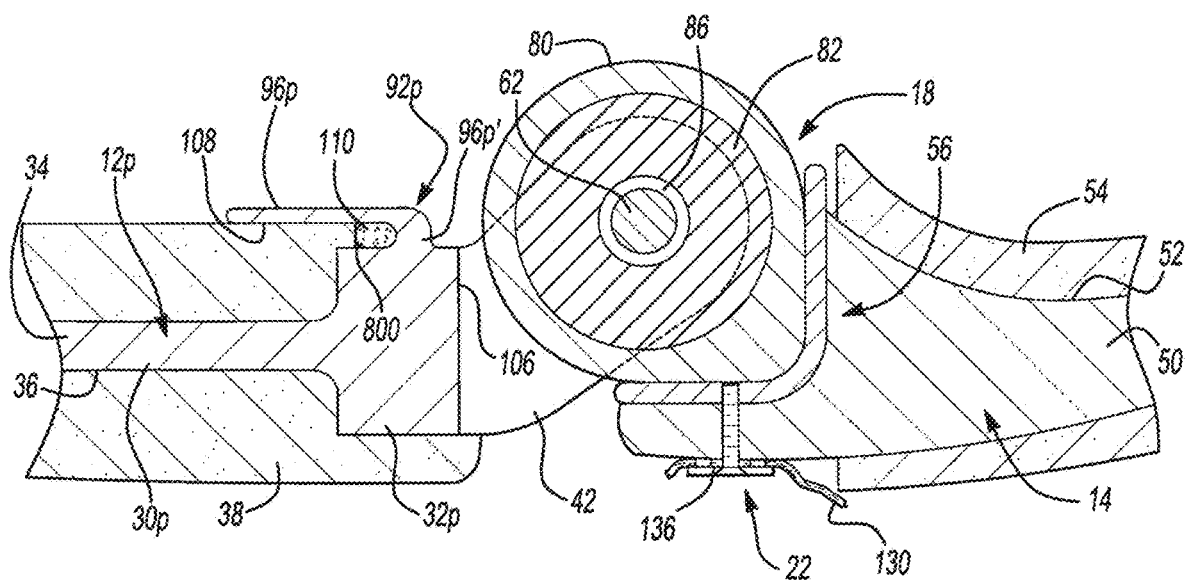
FIG. 27 is a longitudinal cross-sectional view similar to that of FIG. 2, but illustrating the stem with an integrally-formed flange for compressing a bone graft.
Figure 26A:
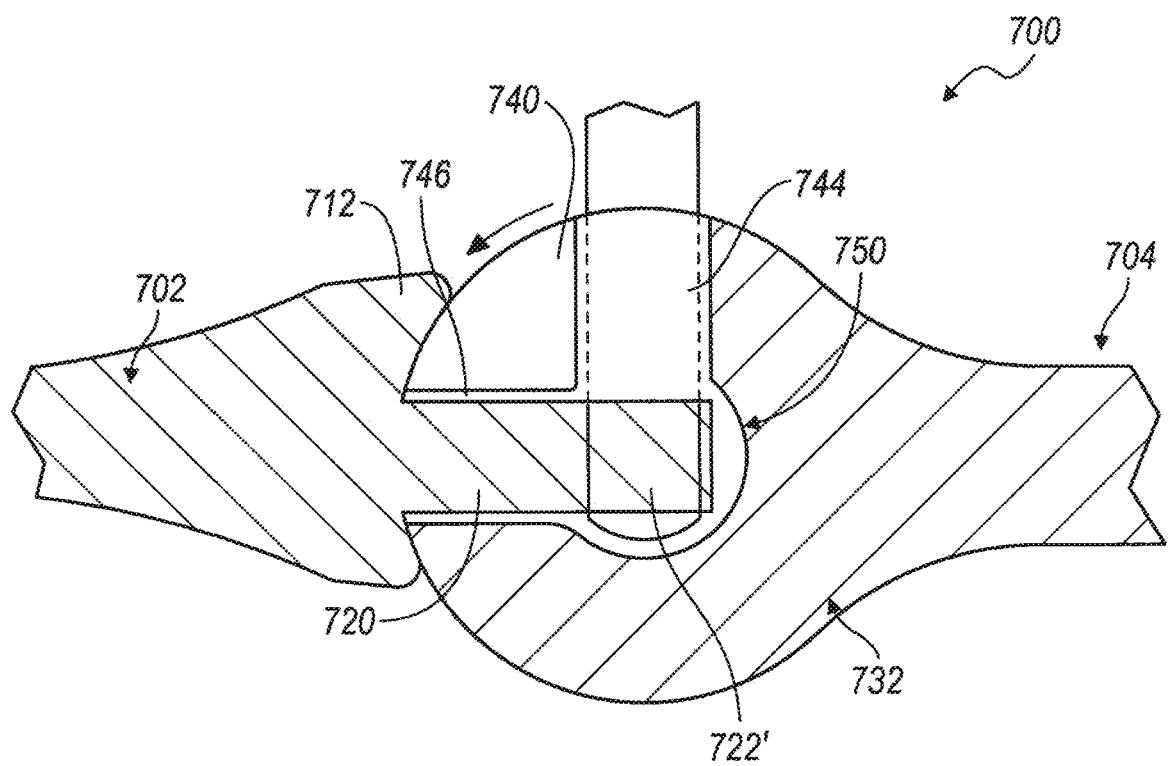
FIG. 26A is another longitudinal cross-sectional view of the linked prosthetic joint kit of FIG. 25

While the prosthetic joint devices 10 and 10$a$ have been illustrated as having modular flanges 20 that are fixedly but removably coupled to the first stem structure 12, those skilled in the art will understand that the teachings, in its broader aspects, may be constructed somewhat differently. For example, the stem structure and modular flange may be unitarily formed as shown in FIG. 27. In this embodiment, the stem 12$p$ is illustrated to be similar to the stem 12, but includes a flange structure 92$p$ having a flange member 96$p$ and a coupling portion 96$p$' that couples the flange member 96$p$ to the distal portion 32$p$ of the stem 12$p$. The flange member 96$p$ is generally parallel the stem member 30$p$ and is employed to compress a bone graft against the stem member 30$p$. Unlike the modular flange 20 that was described in detail, above, the flange structure 92$p$ must be fitted over a bone graft 110 or the bone graft must be placed into the aperture 800 between the stem member 30$p$.

Figure 28:
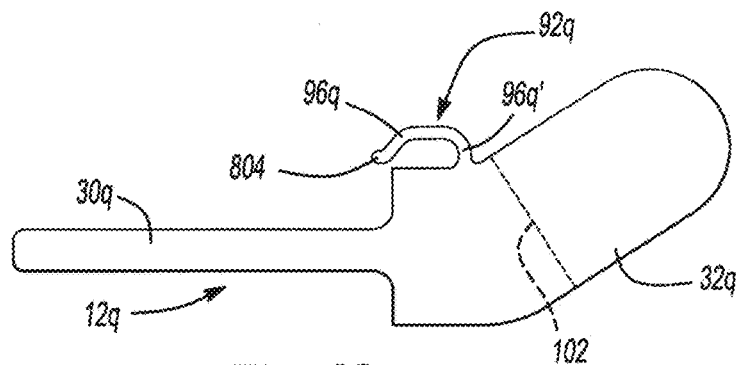
FIG. 28 is a side view illustrating a stem with an integrally-formed, resilient flange for compressing a bone graft.
Figure 29:
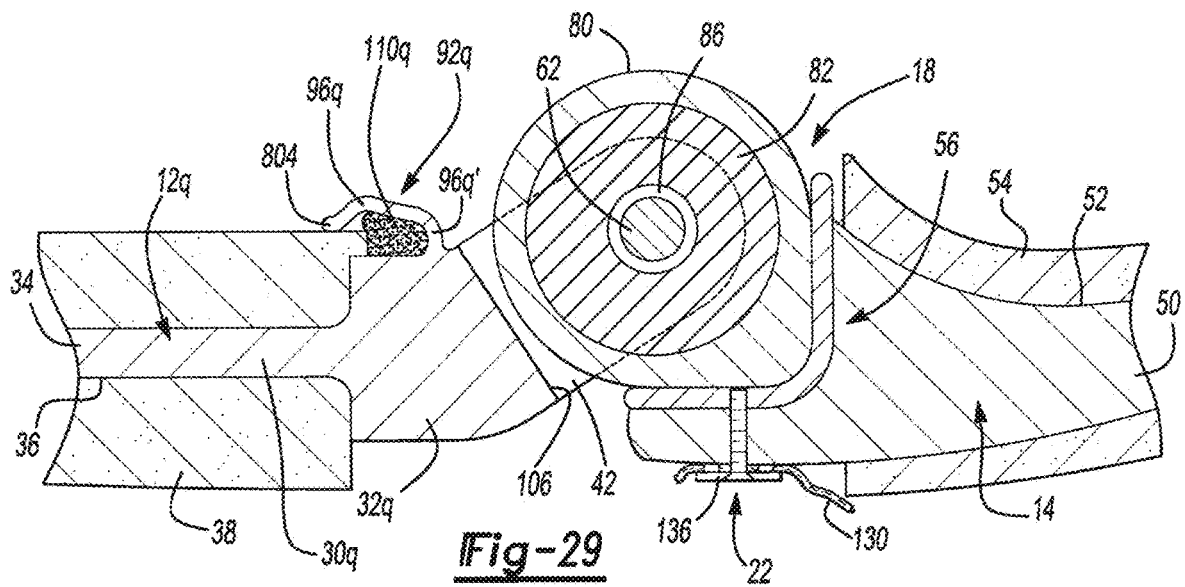
FIG. 29 is a longitudinal cross-sectional view similar to that of FIG. 2, but illustrating the stem of FIG. 28.
Figure 30:
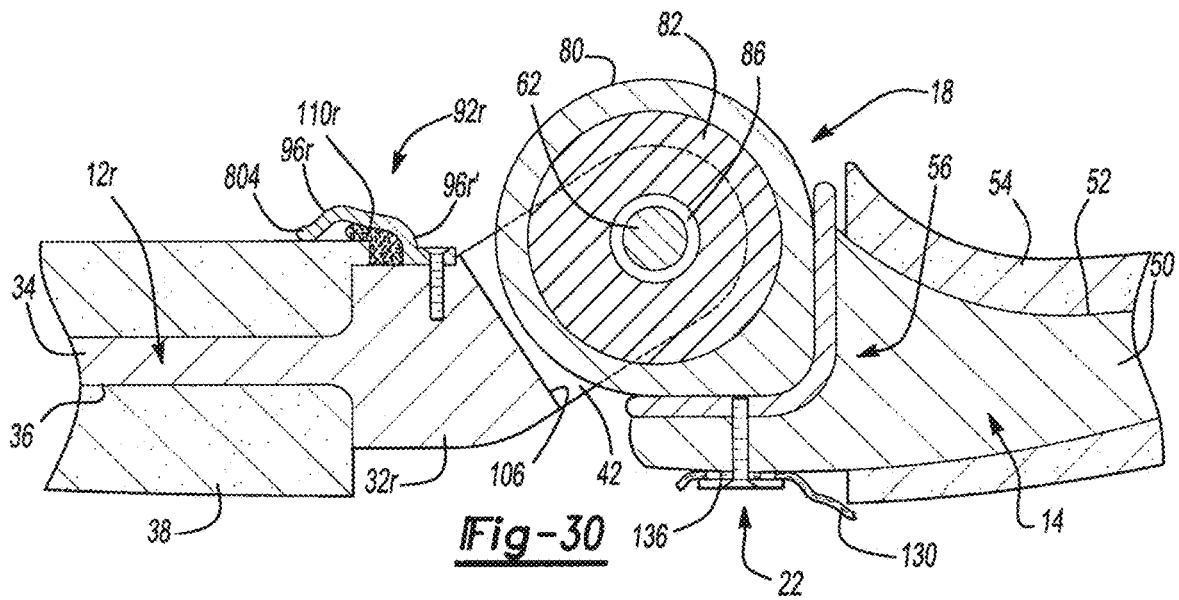
FIG. 30 is a longitudinal cross-sectional view similar to that of FIG. 29, but illustrating the resilient flange as being fixedly but removably coupled to the stem.

Another example of an integrally formed (i.e., non-removable) flange structure is illustrated in FIGS. 28 and 29. In this example, the stem 12$q$ is illustrated to be similar to the stem 12$p$ in that it includes a flange structure 92$q$ having a flange member 96$q$ and a coupling portion 96$q$' that couples the flange member 96$q$ to the distal portion 32$q$ of the stem 12$q$. The flange member 96$q$, however, is arcuately shaped and includes a contact tab 804. The flange structure 92$q$ is formed with a predetermined degree of resiliency, which may result from the characteristics of the material from which the flange structure 92$q$ is formed or by controlling the geometry (i.e., cross-sectional shape and area) of the flange structure 92$q$. The resiliency of the flange structure 92$q$ permits the flange member 96$q$ to act as a leaf spring that biases the contact tab 804 toward the stem member 30$q$. Accordingly, the flange may be employed to apply compression to the bone graft 110$q$ without fasteners or other securing means. As illustrated in FIG. 30, those skilled in the art will readily understand, however, that a predetermined amount of resiliency may also be incorporated into a flange structure 92$r$ that is fixedly but removably coupled to the stem 12$r$.

Figure 31:
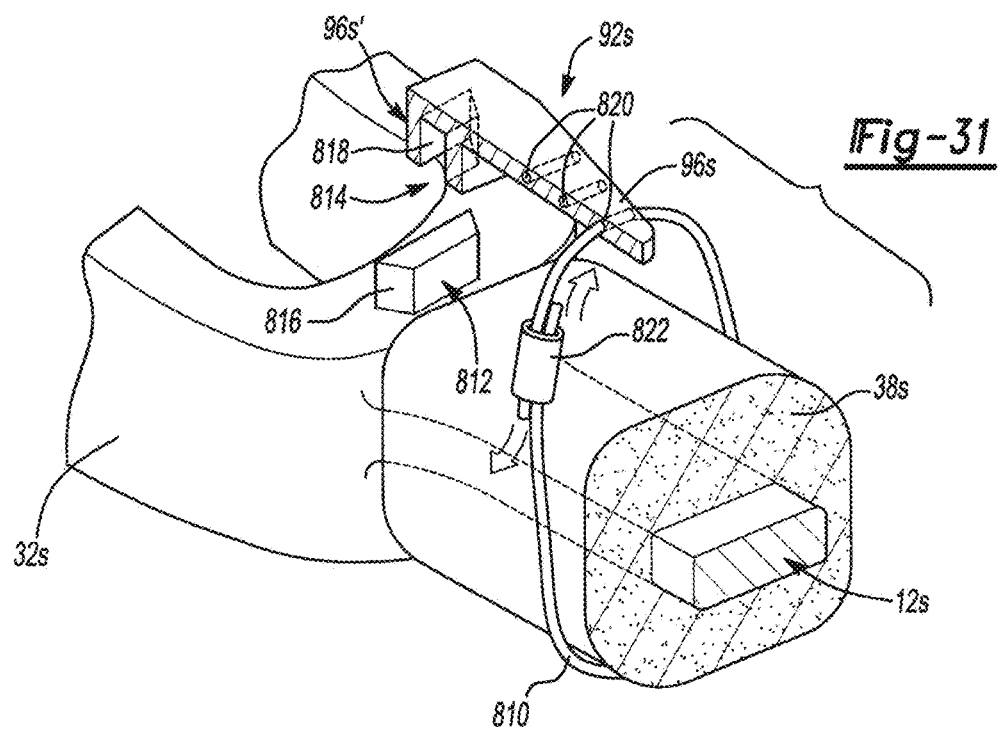
FIG. 31 is a partially broken-away exploded perspective view illustrating an alternative coupling means for coupling the modular flange to the stem.
Figure 32:
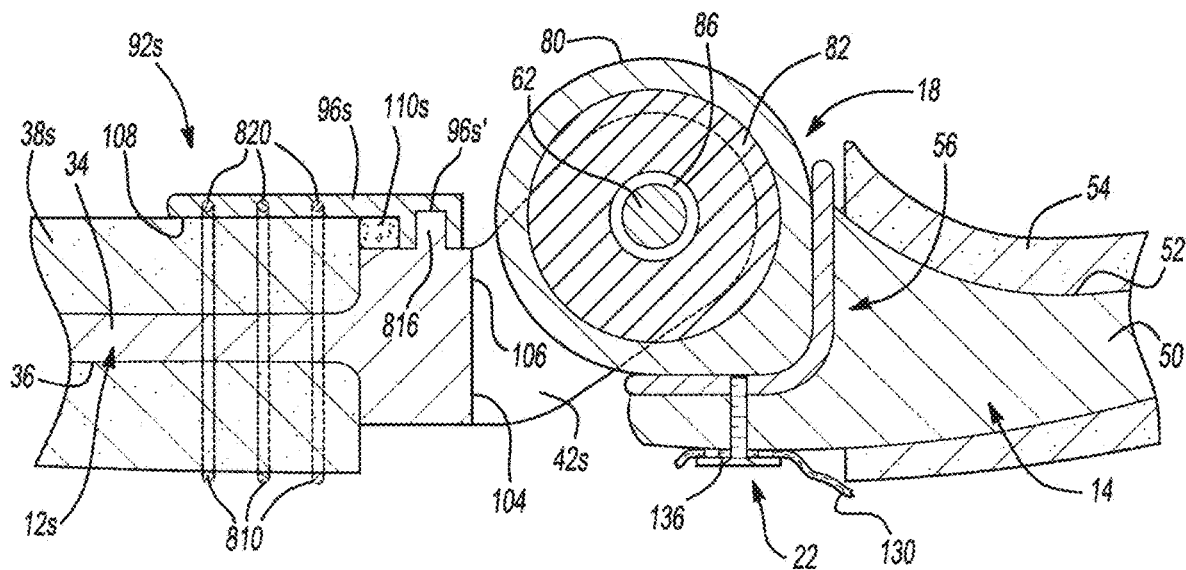
FIG. 32 is a longitudinal cross-sectional view similar to that of FIG. 2, but illustrating the alternative coupling means of FIG. 31.

Those skilled in the art will also understand that although the modular flange 20 has been illustrated as being coupled to the stem 12$r$ via a threaded fastener 94$b$, the teachings, in its broader aspects, may be constructed somewhat differently. For example, cables 810 are employed to fixedly but removably retain the flange structure 92$s$ to the stem 12$s$ as illustrated in FIGS. 31 and 32. The stem 12$s$ is generally similar to the stem 12, but includes a first coupling feature 812 instead of the bore 100. The flange structure 92$s$ includes a flange member 96$s$ and a coupling portion 96$s$'. The coupling portion 96$s$' includes a second coupling feature 814 that is configured to cooperate with the first coupling feature 812 to locate the flange member 96$s$ relative to the distal portion 32$s$ of the stem 12$s$. In the example illustrated, the first coupling feature 812 is a generally trapezoidal dovetail member 816 that extends outwardly from the distal portion 32$s$ of the stem 12$s$ and the second coupling feature 814 is a dovetail aperture 818 that is formed into the coupling portion 96$s$' and sized to engage the dovetail member 816 in with a line-to-line fit (i.e., with very little or no clearance). The dovetail member 816 is preferably integrally formed onto the stem 12$s$ but may alternatively be an independently formed component that is fixedly coupled to the distal portion 32$s$ via an appropriate coupling means, such as threaded fasteners, press-fitting or shrink fitting.

The flange member 96s is shown to include a plurality of cross-holes 820 that extend completely through the flange member 96s in a direction that is generally perpendicular the longitudinal axis of the flange member 96s. The cross-holes 820 are sized to receive the cable 810. As those skilled in the art will understand, the cables 810 are first secured around the humerus 38s and the ends of the cables 810 are loosely secured via an appropriate coupling device, such as a cable sleeve 822. The cables 810 are then tensioned to urge the flange member 96s against the humerus 38s and compress the bone graft 110s by a predetermined amount. Thereafter, the coupling device is employed to fix the ends of the cables relative to one another so as to maintain tension in the cables 810.

While the first and second coupling features 812 and 814 have been illustrated as being a dovetail member 816 and a dovetail aperture 818, respectively, those skilled in the art will appreciate that the first and second coupling features 812 and 814 can be constructed somewhat differently. As illustrated in FIG. 33, for example, the first coupling feature 812t is illustrated as being a pair of pins 830 that are fixedly coupled to the distal portion 32t of the stem 12t and the second coupling feature 814t is illustrated to be a corresponding pair of holes 832 that are formed into the coupling portion 96t. The pins 830 are preferably press-fit or shrunk fit into corresponding holes (not specifically shown) that are formed into the distal portion 32t of the stem 12t but may be secured via other fastening means, such as welding, bonding, or threaded engagement where the pins 830 have a threaded portion that is threadably engaged to the holes in the distal portion 32t. Alternatively, the pins 830 may also be integrally formed as a part of the stem 12t.

Figure 35:
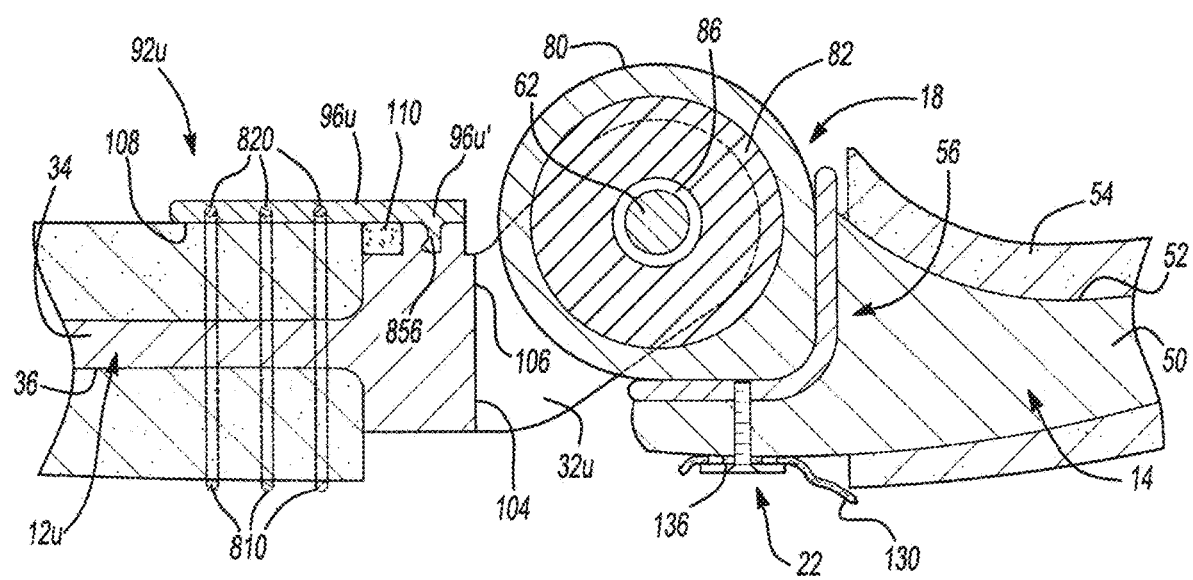
FIG. 35 is a longitudinal cross-sectional view similar to that of FIG. 2, but illustrating the alternative coupling means of FIG. 34.

Another example is illustrated in FIGS. 34 and 35, where the first coupling feature 812u is shown to include a mounting structure 840 with an arcuate mounting aperture 842 and the second coupling feature 814u is shown to include an attachment hook 846. The mounting structure 840 is coupled to the distal portion 32u of the stem 12u and extends generally perpendicularly outwardly from the base 102u of the U-shaped portion 40u. The mounting aperture 842 is generally J-shaped and includes a first portion 850, which is aligned generally perpendicular to the base 102u, and an arcuate second portion 852, which extends away from the stem member 34u and the base 102u. The attachment hook 846 is also generally J-shaped, being configured to matingly engage the mounting aperture 842. In this regard, the attachment hook 846 includes a leg portion 856 that extends downwardly from the flange member 96u and an arcuate base member 858.

In coupling the first and second coupling features 812u and 814u, flange structure 92u is initially positioned relative to the stem 12u such that the base member 858 is disposed within the first portion 850 of the mounting aperture 842. The flange structure 92u is then rotated downwardly toward the stem member 34u to permit the base member 858 to engage the second portion 852 of the mounting aperture 842. The cables 810 are thereafter employed to fix the flange structure 92u relative to the stem 12u.

Figure 36:
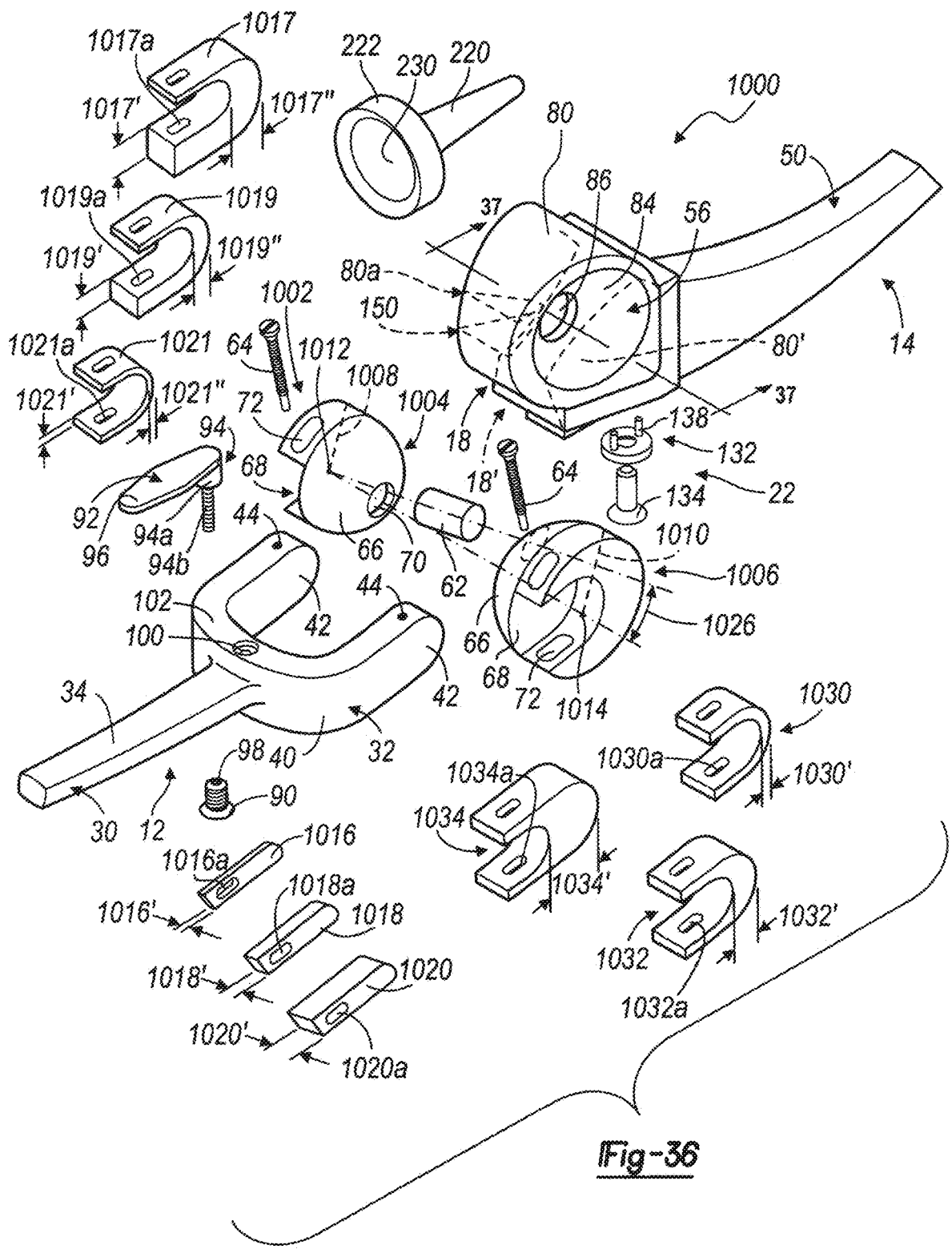
FIG. 36 is an exploded perspective view of a prosthesis according to various embodiments.

With initial reference to FIG. 1 and further reference to FIG. 36, a modular joint prosthesis 1000 is illustrated. It will be understood that the illustrated modular prosthesis 1000 illustrated in FIG. 36 can be similar to the prosthesis 10 illustrated in FIG. 1, though differences can be provided and discussed herein. Nevertheless, like features and portions will be indicated with like reference numerals and not described again in detail. Briefly, however, as discussed above, the modular prosthesis 1000 can be used as a linked elbow prosthesis, although it will be understood according to various embodiments that an unlinked or free elbow prosthesis can be provided, as discussed herein. The prosthesis 1000 can generally include the first stem structure 12, the second stem structure 14, a first bearing component 1002, the second bearing component 18, and various other portions that can be provided or included in the modular prosthesis 1000 if selected. It will be understood that all or various portions are discussed above as included in various embodiments. However, not each of the portions are necessarily provided for each of the embodiments if so selected.

The first bearing component 1002 can define a first condyle portion 1004 and a second condyle portion 1006. The condyle portions 1004, 1006, can be similar to the condyle portions 60 illustrated and described above. According to various embodiments, each of the condyle portions 60 can include substantially similar spherical radii. Although the condyle portion 60 need not define a complete sphere, a portion of the sphere, which they can define, can include or define a spherical radius. According to various embodiments, however, the first condylar portion 1004 can have a first spherical radius 1008 while the second condylar portion 1006 can include a second spherical radius 1010. The first spherical radius 1008 can be different than the second spherical radius 1010.

The spherical radii can be any appropriate dimension such as 1 mm to about 3 cm, such as about 0.6 cm to about 2.0 cm. It will be understood, however, that the spherical radii 1008, 1010, can be any appropriate dimension. For example, the spherical radii 1008, 1010 can be selected for various purposes, such as to substantially mimic a specific anatomy, and as such the various ranges described herein are merely exemplary. Further, it will be understood that the dimensions 1008, 1010, which can include spherical radii, can be any appropriate dimensions. For example, it will be understood that the condylar portions 1004, 1006 need not specifically define a portion of the sphere, a portion of a cylinder, or the like. The condylar portions 1004, 1006 can be irregular such that they are not a regular shape or surface. The design of the condylar portions 1004, 1006 can be specific to various individuals and anatomies, thus not requiring a regular shape.

The condylar portions 1004, 1006 can include the various portions as discussed above. For example, the condylar portions 1004, 1006 can define the bearing portion 66 which can be regular or irregular, as discussed above. Further, each can define the slotted apertures 68 or other appropriate connection portions, to interconnect with the distal portion 32, such as the legs 42 of the first end portion 12. It will be understood that the U-shaped portion 40, which includes the spaced apart the legs 42, can also be referred to as a yoke or other appropriate portion. Further, each of the condyle portions 1004, 1006 can define the pin aperture 70 to interconnect with the condylar pin portion 62 to interconnect the condylar portions 1004, 1006 in a selected manner. As discussed above, however, the condylar portions 1004, 1006, can be substantially formed as a single member or portion that can include the condylar pin 62a as a single portion with the condylar portions 1004, 1006.

Further, as discussed above, the condylar portions 1004, 1006, the condylar pins 62, and any other portions of the prosthesis 1000 can be formed of various materials. For example, it can be selected to form the condylar portions 1004, 1006 from a single material, a composite material, or the like. For example, the condylar portions 1004, 1006 can define the bearing surfaces 66 formed of a polymer material, such as a high molecular weight polyethylene. The second bearing member 18 can also be made of similar materials. Nevertheless, they can also be formed with a metal, metal alloy, ceramic, or the like to achieve various results.

Further, it will be understood that the second bearing portion 18 can include various features and be formed of various materials, including those discussed above. The second bearing member 18 can include the bearing cage 80, the second bearing cage 80*a* which defines the slot 150, or the substantially unconstrained or unlinked various embodiments that include the bearing member 82' and the features thereof as discussed above. Therefore, it will be understood that the condylar portions 1004, 1006 can be interconnected with any appropriate second bearing portion 18, 18' including those described above.

Further, the prosthesis assembly 1000 can include various portions that allow for the substantial non-linear alignment of the condylar portions 1004, 1006 relative to one another. It can be selected to non-align or offset a first center 1012 of the first condylar portion 1004 and a second center 1014 of the second condylar portion 1006. It will be understood that the centers 1012, 1014, can be any operative center or portion of the prosthesis according to various embodiments and defining a geometrical center is merely exemplary. The centers can be offset in various manners such as an anterior-posterior non-alignment, a superior-inferior non-alignment, or combinations thereof.

For example, an anterior-posterior spacer kit can include a first spacer 1016, a second spacer 1018, and a third spacer 1020. Each of the spacers 1016-1020 can include a dimension 1016'-1020' respectively. The dimensions 1016'-1020' can move or displace the selected condylar portions 1004, 1006 relative to the other. A selected spacer, such as the spacer 1016, can be positioned in the slot 68 such that a passage 1022 through the spacer 1016 aligns with the passage 72 through the condylar portion 1006 so that when the leg 42 is positioned within the slot 68, the leg 42 is unaligned with the first condylar portion 1004. A substantially aligned axis 1024 can pass through the two centers 1012, 1014 of the respective condylar portions 1004, 1006 and through the condylar pin 62. Nevertheless, the spacer 1016 can offset a selected condylar portion, such as the second condylar portion 1006 relative to the first condylar portion 1004. Therefore, an offset angle 1026 can be formed between the first condylar portion 1004 and the second condylar portion 1006.

In various configurations, such as an unaligned configuration, various portions are optional. For example, the pin 62 is optional in various configurations. As discussed above, the bearing members 1002 and 1006 bear the force and the pin can assist with strength and stability of the assembly. Thus is the pin 62 can be omitted between the condyles.

The offset angle or distance 1026 can be any appropriate dimension. The appropriate dimension can be selected for various purposes, such as the specific anatomy of the patient, a selected result, or the like. For example, the offset angle can be about 1° to about 20°, such as about 3° to about 10°. Nevertheless, the offset angle can be any appropriate angle depending upon a selected condition. The offset angle 1026 can be altered by choosing a different one of the spacers 1016-1020 and can be selected pre-operatively, intra-operatively, or at any appropriate time.

Each of the spacers 1016-1020 can include a passage or opening 1016*a*-1020*a*. The opening can be a round bore, elongated, a slot or any appropriate opening. The openings 1016*a*-1020*a* can be provided to align or be oriented with the openings 72 in the first and second bearing members 1002 or 1006 and a selected passage 1016*a*-1020*a*.

The openings 72 can also be circular, oblong, slotted, or formed in any appropriate shape or manner. The interaction of the opening 72 in the bearing members 1002 and 1006 and with the openings 1016*a*-1020*a* in the spacers 1016-1020 can help ensure an appropriate fit of the prosthesis 1000.

A second set of spacers 1030-1034 can also be provided. The spacers 1030-1034 can each include a dimension 1030'-1034' respectively. The respective dimension 1030'-1032' can be any appropriate dimension and allow for a selected superior inferior offset. A selected spacer, such as the spacer 1030, can be positioned in the slot 68 to offset the second condylar portion 1006 relative to the first condylar portion 1004. The offset amount can be similar to the angle 1026 except in a different dimension or orientation. The spaces 1030-1034 can also include passages 1030*a*-1034*a*, respectively, that can be similar to the passages 1016*a*-1020*a*. The passages 1030*a*-1034*a* can be round, slotted, oblong, etc. They can be provided to allow for a selected orientation of the prosthesis 1000.

It will be understood, however, that any appropriate number of the various spacers such as the spacers 1016-1020 and the spacers 1030-1034 can be provided for any appropriate purpose. For example, a plurality of the spacers 1016-1020 and 1030-1034 can be provided in minute and discreet differences to allow for an intra-operative selection of a selected offset or to allow for a plurality of offsets for creation from a set of instruments and portions.

With continuing reference to FIG. 36, a third set of spacers 1017, 1019, 1021 can be provided. Although the discussion herein includes a discussion related to three sets of spacers, it will be understood that a set of spacers can include any of the appropriate spacers, all of the spacers, or a selected portion thereof depending upon selected purposes. Nevertheless, the third set of spacers, called that for simplicity of the present discussion, can be formed dissimilar to the second set of spacers 1030-1034. Nevertheless, the third set of spacers 1017-1021 can include a first side 1017*a*-1021*a* that has a dimension that is the same or different than a second side 1017*b*-1021*b*. The various sides can include any appropriate dimension, however, the dimension of side 1017*b*-1021*b* can be varied for various purposes, such as a reason similar to varying the dimension of the first spacer sets 1016-1020. The side 1017*b*-1021*b* can include a dimension 1017'-1021' that can be selected for any appropriate purpose, such as a selected offset, including an anterior or posterior offset. The offsets can be any appropriate offsets, and can be similar to, different, or complementary to the offsets of the spacers 1016-1020. Further, the third set of spacers 1017-1021 can include a third side 1017*c*-1021*c*. It will be understood that the various sides can be any appropriate portions of the spacers 1017-1021 and has described the sides merely for the discussion herein. Nevertheless, the third side, 1017*c*-1021*c* can also include a variable dimension 1017"-1021". The dimension 1017"-1021" can include any appropriate dimension, such as dimensions similar to the dimensions of the second spacer sets 1030-1034.

Therefore the third spacer set 1017-1021 can include a variable dimension of more than one side or portion of the spacers 1017-1021 for various purposes. For example, it can be selected to provide the spacers 1017-1021 to include a selected offset in more than one direction or orientation relative to the prosthesis 1000 or an anatomy into which it is positioned. Therefore, the spacers 1017-1021 can be used to achieve an appropriate orientation of the prosthesis 1000 in a single member. Nevertheless, it will be understood that a modular spacer assembly can be provided to achieve a selected offset in the prosthesis 1000. Having a spacer member that is formed as a single portion or body is not necessary and a modular spacer system can be provided. Nevertheless, a single spacer can include an offset in various dimensions, as exemplary illustrated in the spacers 1017-1021.

Further, the spacers 1017-1021 can include a passage 1017d-1021d similar to the passages described above in the various spacer systems. The passage 1017d-1021d can be circular, oblong, slotted, or any appropriate orientation, size, or the like. The select passage 1017d-1021d can be provided to interact with the passages 72 and the bearing members 1002 and 1006 to achieve a selected orientation of the spacer members relative to the bearing members 1002 1006.

Figure 37:
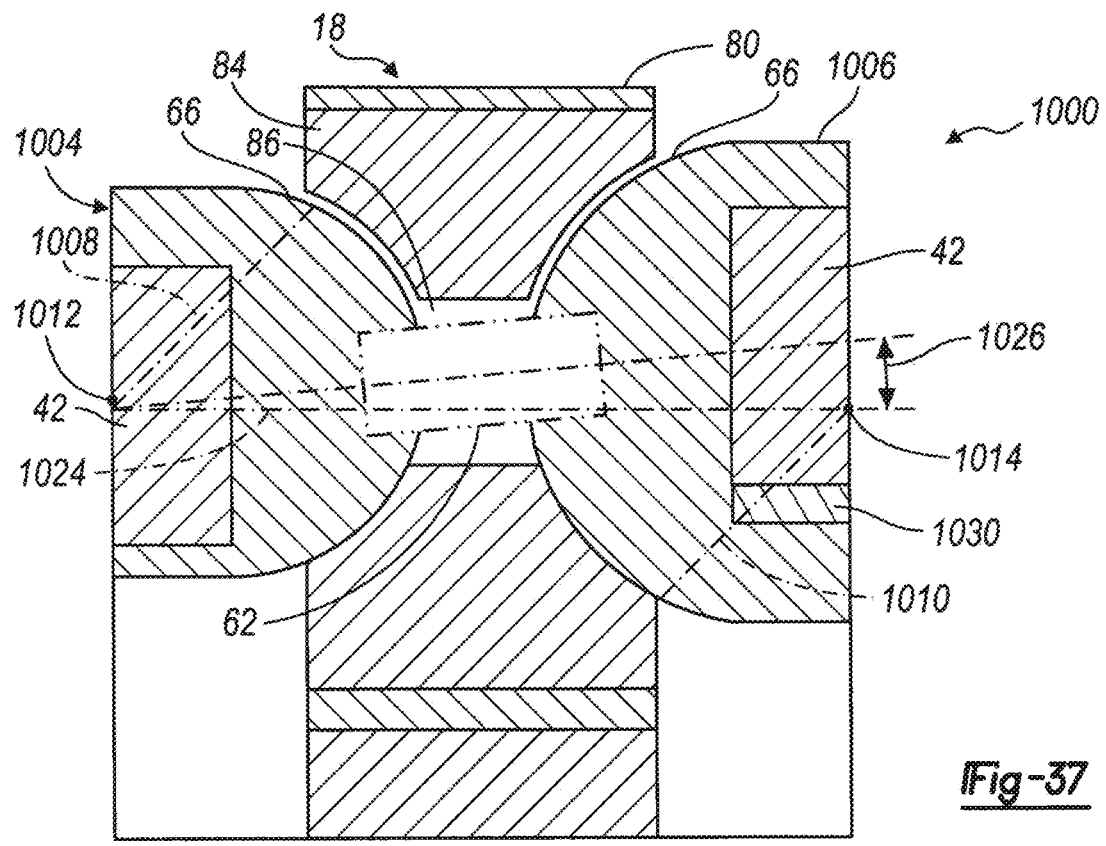
FIG. 37 is a detailed cross-sectional view of an assembled prosthesis according to various embodiments.

With reference to FIG. 37 and continuing reference to FIG. 36, the detailed cross-sectional view of the condylar portions 1004, 1006 relative to the second bearing member 18 is illustrated in an assembled manner. As illustrated in FIG. 37, a selected one of the spacers, such as the spacer 1030 can be inserted into the slot 68 to displace the second condylar portion 1006 relative to the first condylar portion 1004. Therefore, the angle 1026 is formed between the first center 1012 and the second center 1014 with the condylar portions 1004, 1006. Further, as illustrated in FIG. 37, the second condylar portion 1006 can include the dimension 1010 that is larger than the dimension 1008 of the first condylar portion 1004. Thus, the condylar portion 1006 can be designed to mimic a selected portion of the anatomy, if so selected.

Nevertheless, it is still understood that the bearing surfaces 66 can bear on the bearing member 84 of the second bearing member 18 in an appropriate manner. Thus, the condylar pin 62 does not or is not required for proper articulation and may not engage a selected portion of the bearing member 84 after positioning or implantation of the prosthesis 1000. For similar reasons, the pin 62 is not required in the assembly as discussed above. The pin 62 can be omitted for various reasons, such as ease of assembly. Although one skilled in the art will understand that the pin 62 can be used for various reasons, including stability, strength, alignment, and the like. Also, the selected anatomical geometry can be obtained with the prosthesis 1000, which can use any or a plurality of the spacers 1016-1020, 1030-1034, or 1017-1021 to achieve any appropriate offset or angle and also the dimension of the condylar portions 1004, 1006 can be selected to achieve the appropriate results.

Figure 38:
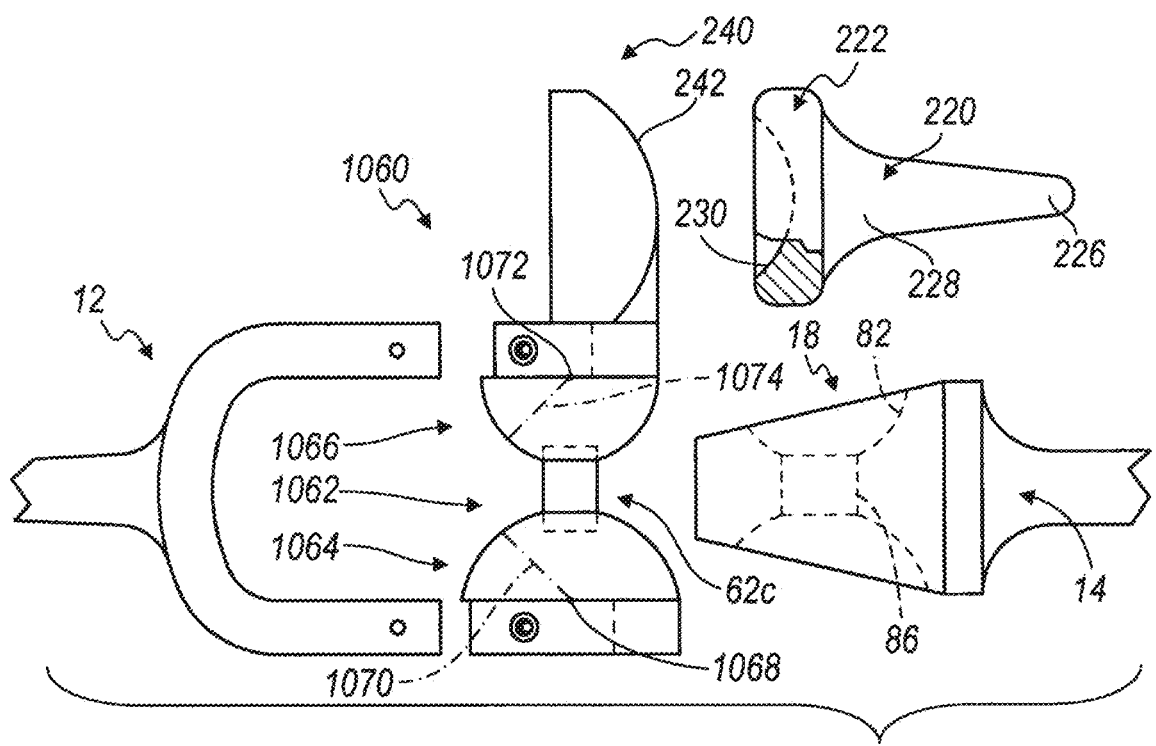
FIG. 38 is an exploded plan view of a prosthesis according to various embodiments.

With reference to FIG. 38, a modular prosthesis assembly 1060 can include various portions, including those discussed above. It will be understood that the similar portions can be referenced by like numerals and a detailed description thereof need not be necessary here to understand the various embodiments. Nevertheless, the first stem assembly 12 can be provided to interconnect with a first bearing assembly 1062 and a second stem assembly 14 and a third stem assembly 220. As discussed above, the fourth bearing component 222 can be provided with the stem assembly 220 to interconnect with the radius to replace articulating portion thereof. It will be understood that the stem assembly 220 can be provided with various portions to achieve a replacement of a selected portion of the radius.

It will be further understood that, as described above in various embodiments, that the bearing portion 222 can be formed as a single member with the second stem assembly 14 according to various embodiments. The first bearing assembly 1062 can include a first condylar portion 1064, a second condylar portion 1066 and the extension 240. The extension 240 can be provided to extend from a selected portion of the first bearing member 1062 such as medial or laterally from the first bearing member 1062. The extension 240 can define the extension bearing member 242 that can articulate with the bearing portion 222 of the stem 220 or with the natural portion of the radius. Further, as discussed above, the bearing surface 222 can articulate with the natural portion of the humerus if so selected. Also, the second bearing member 18 can be provided in a substantially linked, unlinked or unconstrained, semi-constrained or linked, or a slot that allows access to the bore 86 in any appropriate manner.

The first bearing member 1062 can be interconnected with the first stem member 12 in any appropriate manner, including the various screws or fixing member 64 as described above. Further, the condylar portions 1064, 1066 can be interconnected with the condylar pin 62c in any appropriate manner, including those discussed above. Nevertheless, the first condylar member 1064 can be provided in a different manner, geometry, size, etc., than a second condylar member 1066.

As discussed above, the first condylar member 1064 can have a centerpoint 1068 that can define a center of a sphere or any other regular or irregular shape. For example, the first condylar portion 1064 can define a spherical radius 1070 that extends from the center 1068 to an edge of the condylar member 1064. The second condylar member 1066 can also define a center 1072, which can be the center of a sphere or any other appropriate shape or irregular shape. Further, the second condylar portion can define a second spherical radius 1074. As discussed above, the spherical radii 1070, 1074 can be provided to be equal, different, or in any appropriate combination. Nevertheless, it will be understood that the condylar portions 1064, 1066 can include a different dimension and be interconnected with the various portions, such as the extension 242 to articulate with various portions of the anatomy or prostheses positioned therein. It will also be understood that the condylar portions 1064, 1066 can interconnect with the first stem member 12 in any appropriate manner. Therefore, various further portions, such as the spacers 1016-1020, 1030-1034, or 1017-2021 can be provided with the prosthesis system 1060.

It will be understood that the various embodiments of the prostheses, whether linked or unlinked or constrained or unconstrained can be provided in various portions of the anatomy. Nevertheless, the exemplary elbow prostheses can be provided in various manners for selection by a user. As discussed above, a kit can include each and every of the various portions of the various embodiments for selection by a user during an operative procedure, prior to an operative procedure, or at any appropriate time. Therefore, the modular prosthesis, according to various embodiments, can be provided for use by a user in a selected manner to achieve a selected result.

Figure 39:
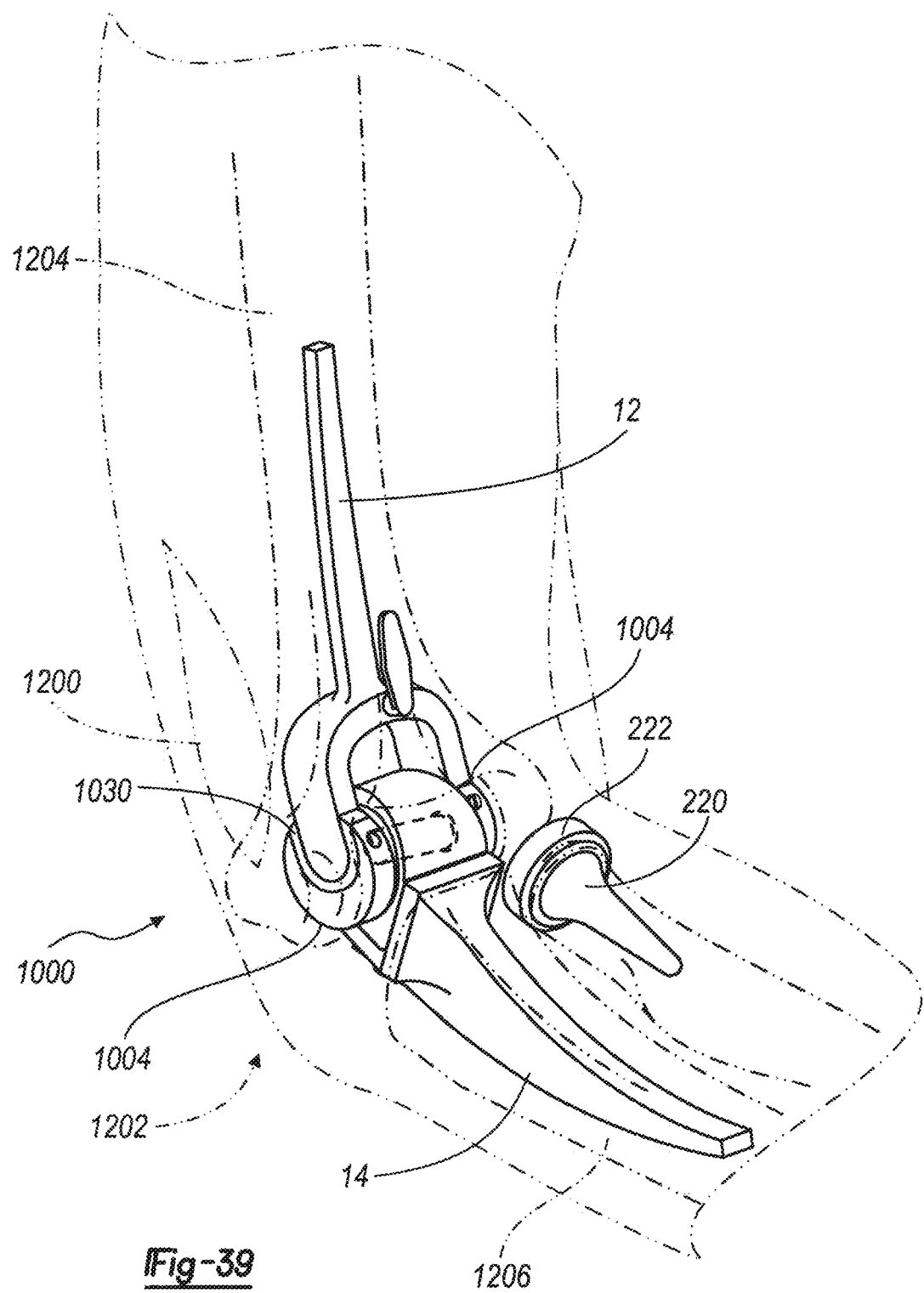
FIG. 39 is a detailed environmental view of a prosthesis implanted in an anatomy according to various embodiments.

Further, with exemplary reference to FIG. 39, the prosthesis 1000 can be positioned in the anatomy in any appropriate manner. The modular prosthesis can be provided to be positioned relative to various portions of the anatomy, such as a humerus, a radius, an ulna, or any appropriate portions through a selected incision 1200 relative to the elbow 1202 joint between the hummers 1204 and ulna 1206. It will be understood that the modular nature of the prosthesis 1000, can be provided for a procedure that can be performed through a relatively minor incision that need not be larger than various portions of the modular prosthesis. This can achieve various results, such as minimizing recovery time, minimizing operation time, or various selected results. Further, as discussed above, the modular nature of the various portions and various embodiments can provide for achieving a selected revision procedure. For example, having the various sizes of the condylar portions, which can include different dimensions, a revision procedure can be provided to maintain or augment a selected result to achieve a more anatomical result in a selected period. Further, the prosthesis, according to various embodiments, can be changed from a constrained to unconstrained or from an unconstrained to a constrained. The change can be provided during a selected procedure, such as a revision procedure to account for changes in the anatomy over time. Nevertheless, the modular prosthesis according to various embodiments can be provided for selection by a user to achieve a more natural anatomical result after implantation of the prosthesis.

Figure 40:
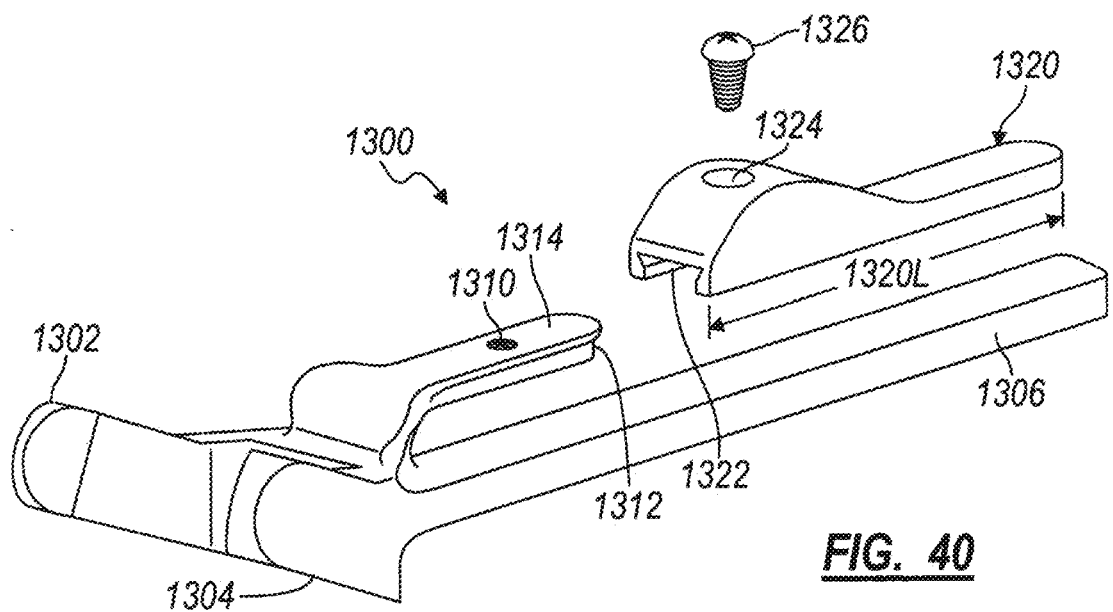
FIG. 40 is a perspective view of a stem structure with a modular flange.

With reference to FIG. 40, a humeral prosthesis stem assembly or structure 1300 is illustrated. The stem assembly 1300 can include a first and second arm 1302, 1304 to cooperate or engage the pair of condyle portions 60, according to various embodiments. The stem assembly 1300 can include a stem portion 1306 that is operable to extend into a canal, such as the intramedullary canal of a humorous. Extending with the humeral stem assembly 1300 can be a flange attachment or connection member 1310. The flange attachment member 1310 can define a dovetail, such as a male dovetail 1312. The flange attachment member 1310 includes a bore or passage 1314.

A modular flange member 1320 can interconnect with the flange attachment member 1310. The modular flange member 1320 can define a female dovetail connection 1322. The modular flange member 1320 can also include a passage or bore 1324 through which a locking screw or set screw 1326 can pass. During or with an implantation procedure, the modular flange member 1320 can slide over the flange attachment member 1310 and the set screw 1326 can lock the modular flange member 1320 to the flange attachment member 1310.

It will be understood, according to various embodiments, that the modular flange member 1320 includes a female or male connection portion other than the dovetail female dovetail connection 1322. The flange attachment member 1310, however, can include any appropriate connection portion other than the male dovetail 1312. The appropriate connection portion allows the flange member 1320 to be slid axially over the flange attachment member 1310. By axially sliding or moving the flange member to connect it to the flange attachment member 1310 increased resistance to rotation or torsion can be achieved of the flange member relative to the remainder of the stem assembly 1300. As discussed above, the flange member 1320 can be provided to resist rotation of the stem assembly 1300 in the anatomy.

For example, the male and female dovetails can be reversed or other appropriate configurations can be provided. For example, a male T-portion and a female T-portion can be provided on the respective flange attachment member 1310 and modular flange members 1320. The T-portions can also allow an appropriate cooperation of the flange member 1320 and the flange attachment member 1310.

The flange member 1320 can be provided with any appropriate length 1320L. The length 1320L can also be provided to vary amongst a plurality of the flange members 1320. The plurality of the flange members 1320 can be provided in a kit, such as in the prosthesis assembly 1000 illustrated in FIG. 36 or any other appropriate kit or modular prosthesis assembly.

As discussed above, the flange member 1320 or the flange attachment member 1310 can be provided to engage the humerus to assist in reducing or eliminating rotation of the humeral assembly 1300 after or during implantation. The modular flange member 1320 that can be provided in a plurality of lengths and the appropriate length can be selected by a user, such as the surgeon, during a procedure. The length of the modular flange member 1320 can be selected based upon the length of the patient's humerus, the amount of area to be covered to resist rotation, and for other selected purposes.

The modular flange member 1320 can also be interconnected with the flange attachment member 1310 at any appropriate time. For example, the flange member 1320 can be interconnected with the flange attachment member 1310 prior to positioning the humeral stem assembly 1300 into a humerus of the patient. Alternatively, the flange member 1320 can be interconnected with the flange attachment member 1310 after positioning the stem portion 1306 within the humerus.

Figure 41:
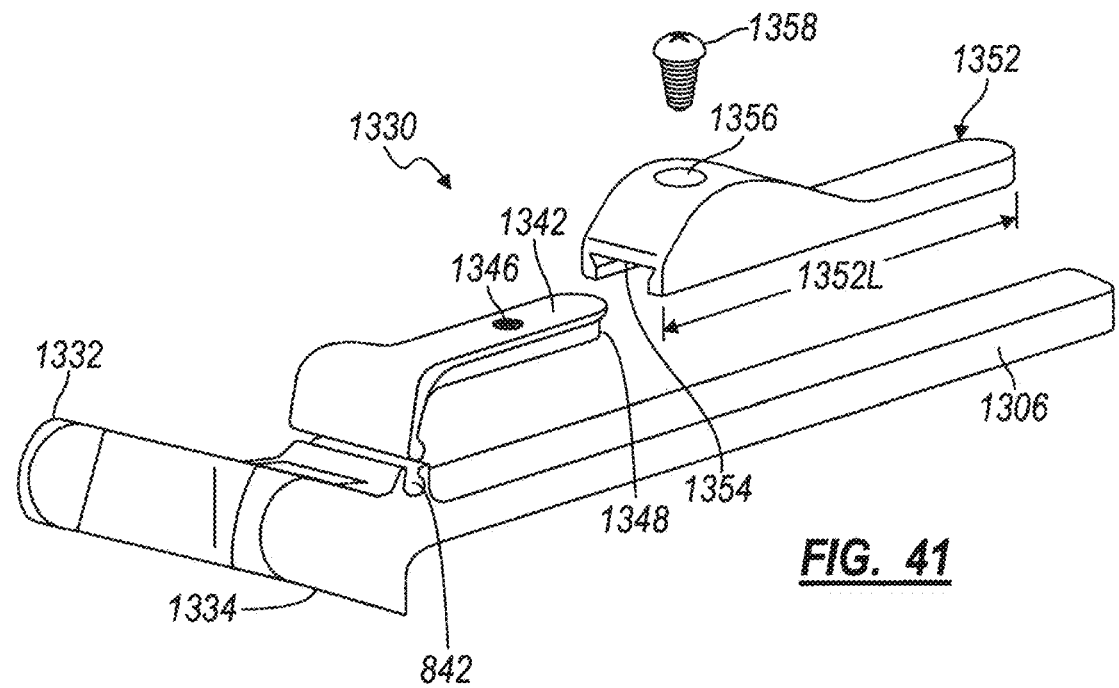
FIG. 41 is a perspective view of a stem structure with a modular flange.

According to various embodiments, a multiple or plural flange humeral assembly 1330 can be provided, as illustrated in FIG. 41. The humeral assembly 1330 can include two arms or furcations 1332 and 1334 to engage the condyle bearings, as discussed above. The humeral assembly 1330 can further include a stem portion 1336 to engage or be positioned in the humerus, as also discussed above. A modular flange assembly 1340 with multiple members are assembled to engage the stem portion 1336 cooperate with the stem portion 1336. The modular flange assembly 1340 can include any appropriate number of modular members, including two as discussed herein. Also, the modular flange assembly can connect directly to the stem portion 1306 or any appropriate portion of the humeral assembly 1330, including near the two arms or furcations 1332, 1334. The modular flange assembly 1340 can allow for greater flexibility during a procedure and multiple sets of the modular flange assembly 1340 can further increase flexibility.

A flange connection member 1342 can include a connection portion 1344 to connect with an arcuate mounting aperture 842. The arcuate mounting aperture 842 can be provided to interconnect with the connection portion 1344 as discussed above. The arcuate connection aperture 842 and the connection portion 1344 can allow for a selected connection of the flange connection member 1342 to the remainder of the humeral assembly 1330.

In addition, the flange connection member 1342 can include a threaded bore or passage 1346 similar to the passage 1314 discussed in FIG. 40. In addition, the flange connection member 1342 includes a male dovetail connection portion 1348. A separate modular flange member 1352 includes a length 1352L. The modular flange member 1352 includes a female dovetail connection region 1354 to cooperate with the male dovetail 1348. As discussed above, however, a dovetail connection is not required and any appropriate selectable connection can be provided.

A passage 1356 if formed through the flange member 1352. A locking or set screw 1358 can pass through the passage 1356 and the passage 1346 to assist in locking or holding the flange member 1352 to the flange connection member 1342. The flange member 1352 can be held or fixed relative to the flange connection member 1342 with any appropriate mechanism, such as a tab or deflectable finger.

As discussed above, the flange member 1352 can be provided in any appropriate length. Further, the length 1352L can vary among a plurality of the flange members 1352. A plurality of the flange members 1352 can be provided in a kit or in a modular assembly system, such as the modular assembly system 1000. The user can select the appropriate length flange member 1352 for any appropriate reason, such as that discussed above.

In addition, the kit, or any appropriate kit, can include a humeral assembly portion, such as the humeral assembly 1300 or the humeral assembly 1330. A selection of an appropriate humeral assembly can be made for appropriate purposes, such as providing for a selected or unique anatomy of a patient. For example, if a patient's anatomy is substantially planar the flange attachment member 1310 can be used.

If varying widths of a patient's anatomy need to be accommodated then the multiple modular flange assembly 1340 can be used to accommodate the varying widths with a plurality of members. For example, the arcuate connection 1344 can position the flange connection member 1342 at any selected distance from the stem portion 1336. The flange member 1352 can then be selectively interconnected with the flange connection member 1342 during an implantation procedure.

It will be understood that the flange assembly 1340, the flange member 1320, or a flange according to the various embodiments can be provided with any appropriate humeral assembly. The humeral assembly can be implanted for forming a portion of an elbow joint, as discussed above. The flange assembly can be provided with a modular member to select a selected length, offset, or other configuration of the flange member relative to the stem portion of the humeral assembly.

Figure 42:
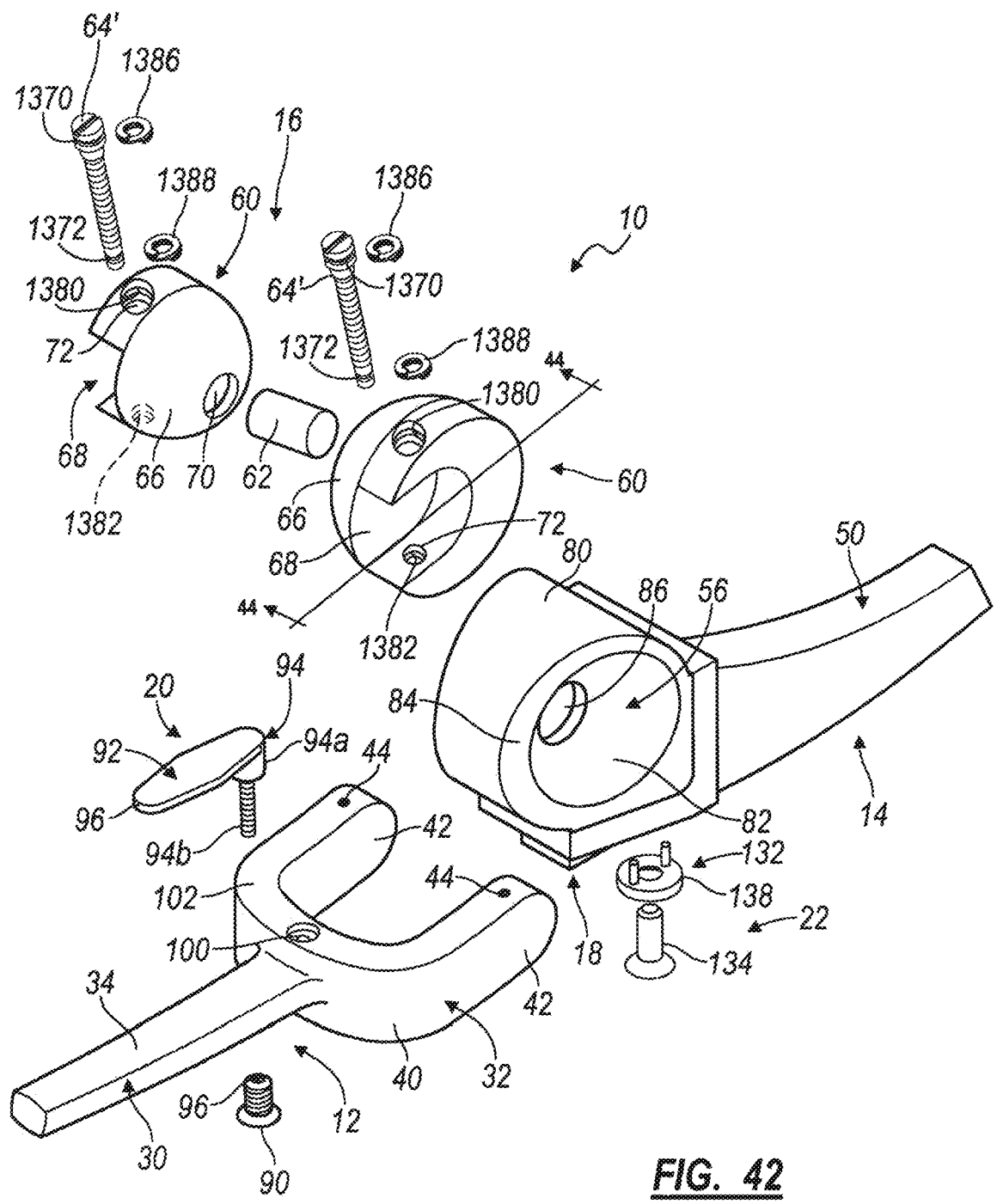
FIG. 42 is an exploded perspective view of an elbow prosthesis, according to various embodiments.
Figure 43:
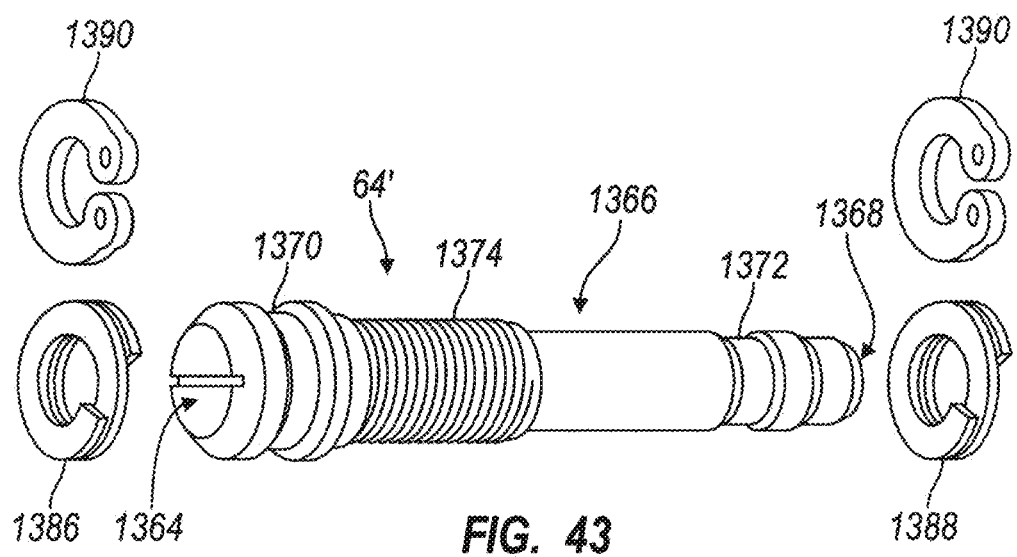
FIG. 43 is a detail plan view of a first and second fastener.
Figure 44:
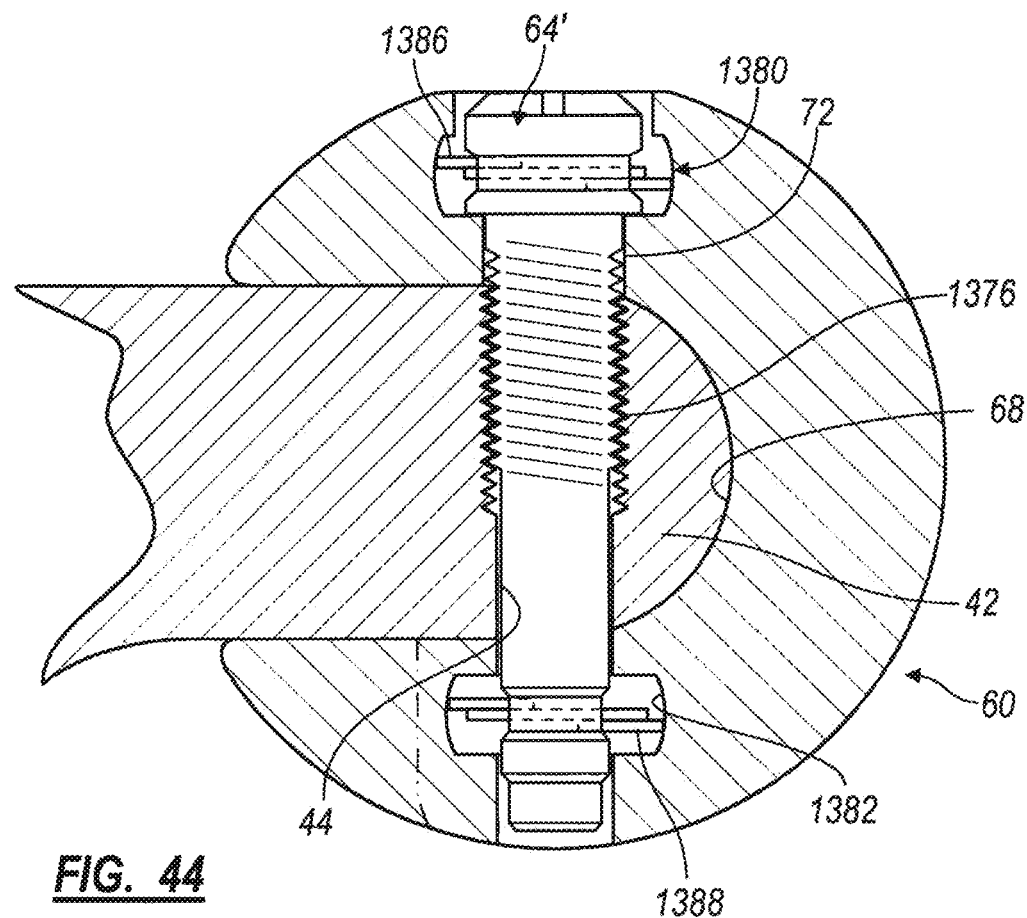
FIG. 44 is a detail cross-sectional view of the elbow prosthesis of FIG. 42 along line 44-44.
Figure 45:
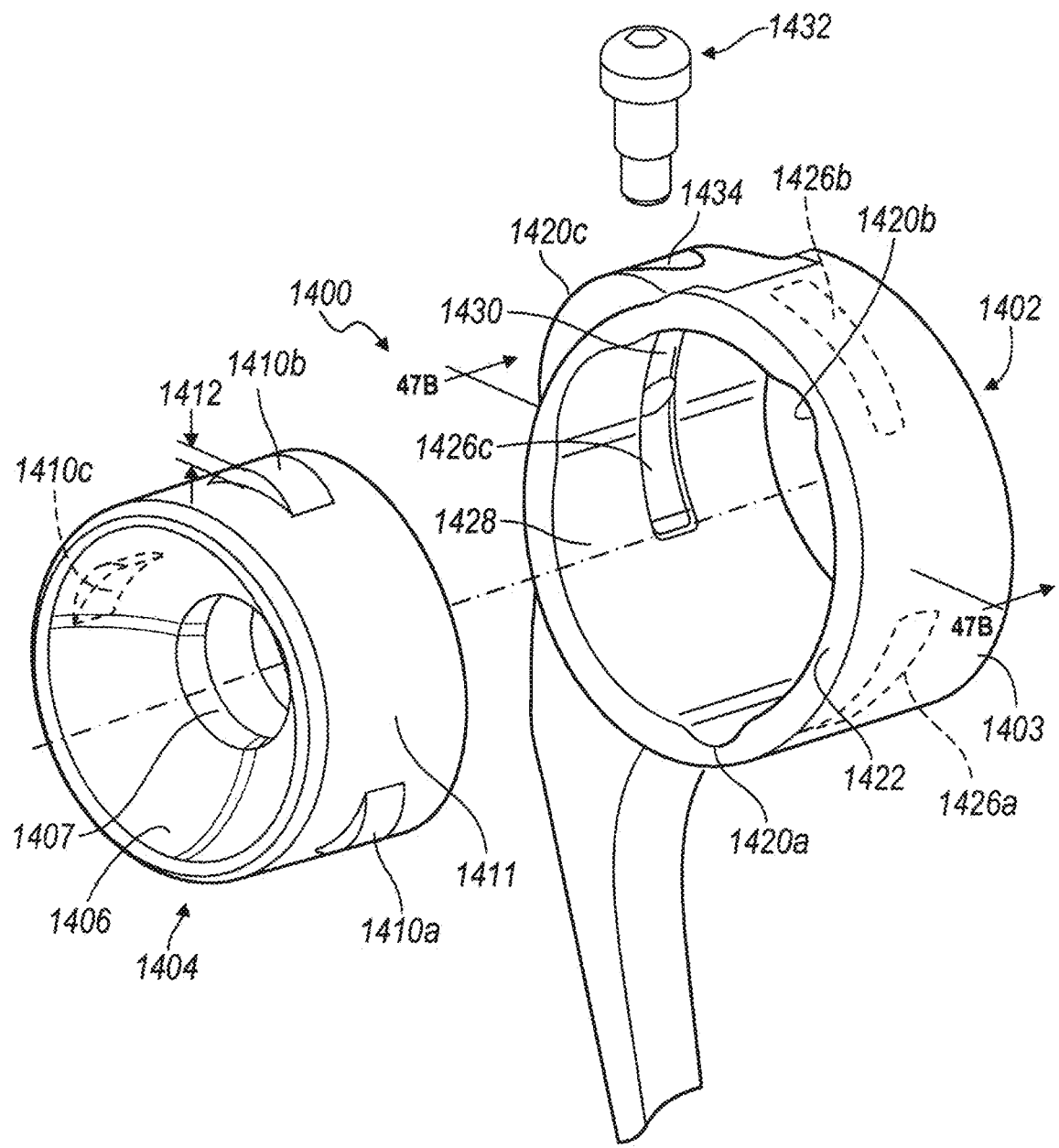
FIG. 45 is an exploded perspective view of a stem structure with modular bearing member.
Figure 46:
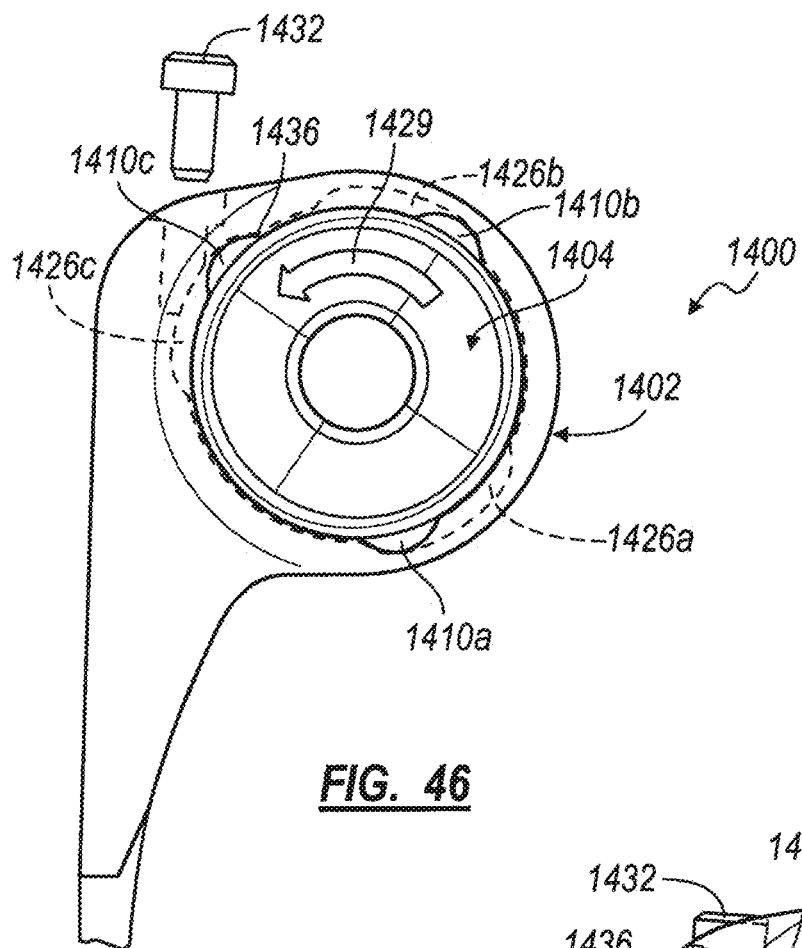
FIG. 46 is a plan view of an assembled stem structure of FIG. 45 in a first orientation.

As discussed above, a prosthetic joint 10 can include a bearing component 16 that includes first and second condyle portions 60. As further discussed above, and illustrated in FIG. 1, the condyle portions can be connected to the first stem structure 12 with a fastener 64. The fastener 64 can pass through bores or passages in the condyle portions 60 and in the stem structure 12 to connect the condyle portions 60 to the stem structure 12. According to various embodiments, as illustrated in FIGS. 42-44, a first and second stem structures 12, 14 and the bearing component 16 can be associated to form an elbow joint prosthesis.

For example, a fastener 64' can be provided and positioned to interconnect the condyle portions 60 with the arms or furcations 42. The fastener 64 can extend through the furcation 42 and engage the condyle portion 60 to hold the condyle portion relative to the respective furcation 42. Similarly, the fastener 64' can pass through or engage both the condyle portion 60 and the respective furcation 42 to hold the condyle portion 60 relative to the respective furcation 42. The fastener 64' can include a first and a second fixation or fastening region. As discussed herein, first and second fastening regions can include first and second fastener grooves 1370, 1372 and a fastener thread 1374.

The fastener 64' includes a head 1364, a shaft 1366 extending from the head, and a distal tip or region 1368. The fastener 64' further includes a first fastener groove 1370 and a second fastener groove 1372. The shaft 1366 includes a male fastener thread 1374 located intermediate the head 1364 and the distal tip 1368 in the depicted embodiment. The fastener thread 1374 can be provided to engage a female thread, such as a female thread 1376 of the threaded fastener aperture 44. The fastener 64' also passes through at least one part of the mounting aperture 72 in the condyle portion 60.

During an assembly, the fastener 64' can pass through a first part of the mounting aperture 72, pass through the threaded fastener aperture 44, and pass through a second part of the mounting aperture 72. It will be understood that the fastener 64' need only pass through a one part of the mounting aperture 72. The fastener 64' can be held at a selected location relative to the furcation 42 and the condyle portion 60 at least with the fastener threads 1374 in the threaded fastener aperture 44.

The threaded interaction between the fastener threads 1374 and the female threads 1376 can create or generate a first fastening interaction. A second fastening interaction can be formed with a second fastener and by either or both of the grooves 1370 and 1372 in the fastener 64' and cooperating grooves 1380 and 1382 included in the mounting aperture 72. A groove can also be defined in the threaded fastener aperture 42. The second fastener can be at least one of a first locking spring 1386 and a second locking spring 1388. The springs 1386, 1388 can be any appropriate springs, such as helical spring or flex spring members. The second fastener can also be a locking ring or C-ring 1390. The second fastener is provided to cooperate with one of the selected groove pairs 1370 and 1380 or 1372 and 1382. The locking springs 1386, 1388 can be positioned between the pairs of grooves 1370, 1380 or 1372, 1382 to resist movement of the fastener 64' within any of the threaded fastener aperture 44 or mounting aperture 72.

As best illustrated in FIG. 44, the fastener 64' can be positioned within the respective apertures 72, 44, and the springs 1386, 1388 can be positioned within the groove pairs 1370, 1380 or 1372, 1382 to assist in holding the fasteners 64' within the apertures. At least one of the springs 1386, 1388 is placed in the grooves 1380, 1382 of the condyle portions 60 or any appropriate portion of the assembly during assembly. The fastener 64' is inserted to engage at least one of the springs 1386, 1388 which flexes the spring 1386, 1388. The fastener 64' is then further inserted to allow the spring 1386, 1388 to relax into the respective fastener groove 1370, 1372

The second fastener is provided to assist in resisting movement of the fastener 64'. For example, once the fastener 64' is positioned in the prosthesis 10 and multiple articulations or cycles of the prosthesis 10 occurs within a patient, the fastener 64' may loosen relative to the furcation 42. The locking spring 1386, 1388 or any appropriate locking member can ensure that the fastener 64' does not move more than a selected distance. Accordingly, the condyle member 60 can be maintained connected to the respective furcations 42.

The first bearing component 16, according to various embodiments, can be held in place relative to the first stem structure 12, as discussed above. It can be selected to provide both a first and second interaction for the fastener 64'. The first bearing component 16 can then be implanted or positioned to articulate with the second bearing component 18.

With reference to FIGS. 45-47B, a second stem structure 1400 having a second bearing component 1402 can include a cage or enclosed structure 1403 that can couple with or hold a bearing member 1404 in a selected position in a second stem structure 1400. The bearing member 1404 can define a bearing surface 1406 that can include two faces or opposing partially- or semi-spherical bearing surfaces. A through bore or passage 1407 can also be defined through the bearing member 1404. The bearing surfaces 1406 and passage 1407 can have any appropriate configuration, including that discussed above. For example, the bearing surface 1406 can include two bearing sections defined around axes that are at an angle relative to one another. The various configurations of the bearing structure of the bearing member 1404 are discussed above and not repeated here.

The bearing member 1404 can be held within the cage 1403 with a holding member, such as tabs 1410a-1410c included in an exterior surface 1411 of the bearing member

1404. The holding member can include portions of both the bearing member 1404, the cage 1403, or other members, as discussed herein. The tabs 1410a-1410c can extend a height 1412 above the exterior surface 1411 of the bearing member 1404. The tabs 1410a-1410c can pass through tab entries 1420a-1420c in the cage 1403 formed in a sidewall 1422 of the cage 1403. Although three tabs 1410a-1410c are discussed and illustrated here, any appropriate number of tabs can be provided.

Figure 47A:
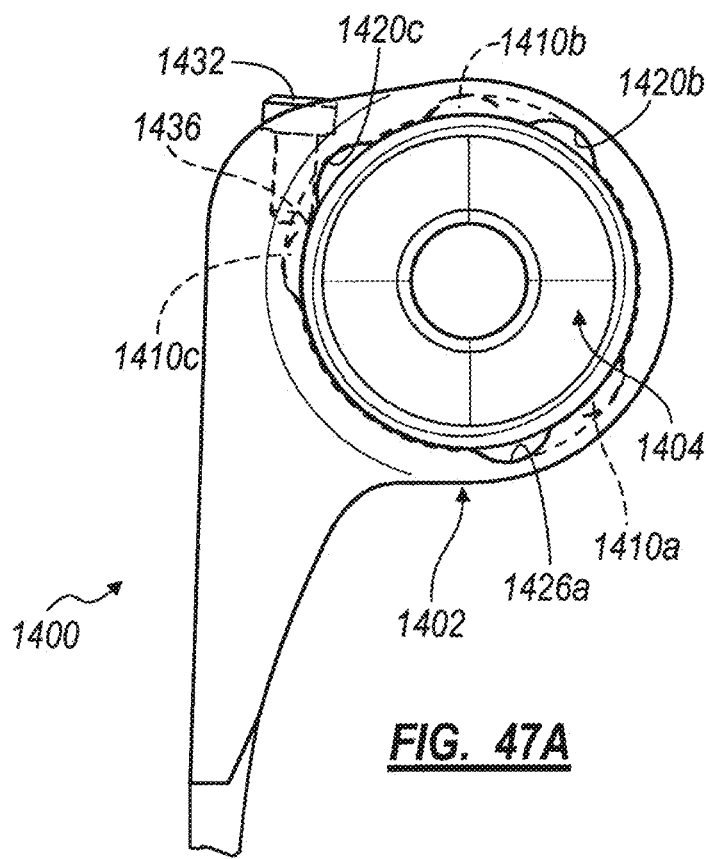
FIG. 47A is a plan view of an assembled stem structure of FIG. 45 in a second orientation.
Figure 47B:
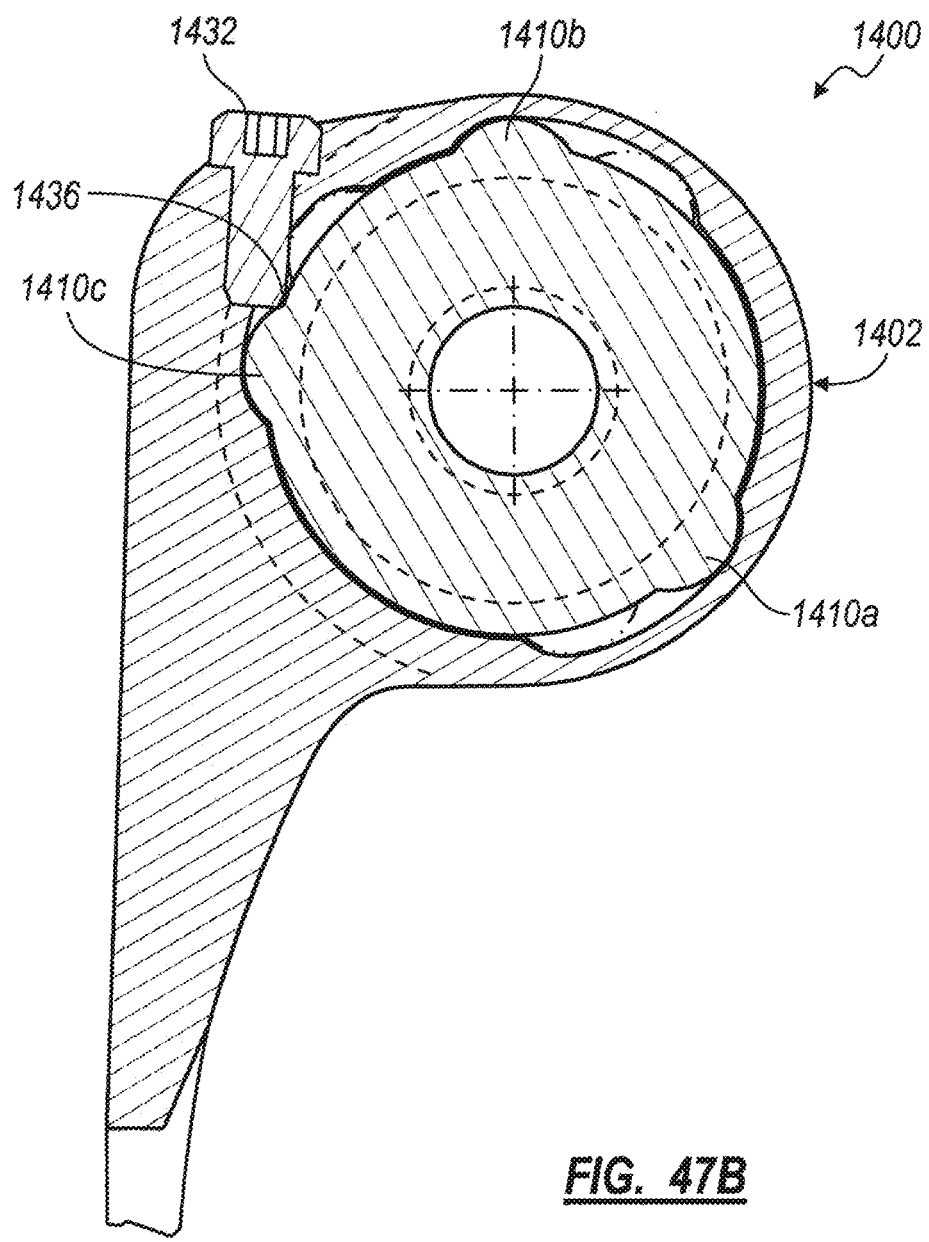
FIG. 47B is a cross-sectional view of the assembled stem structure of FIG. 47A along line 47B-47B.
Figure 48:
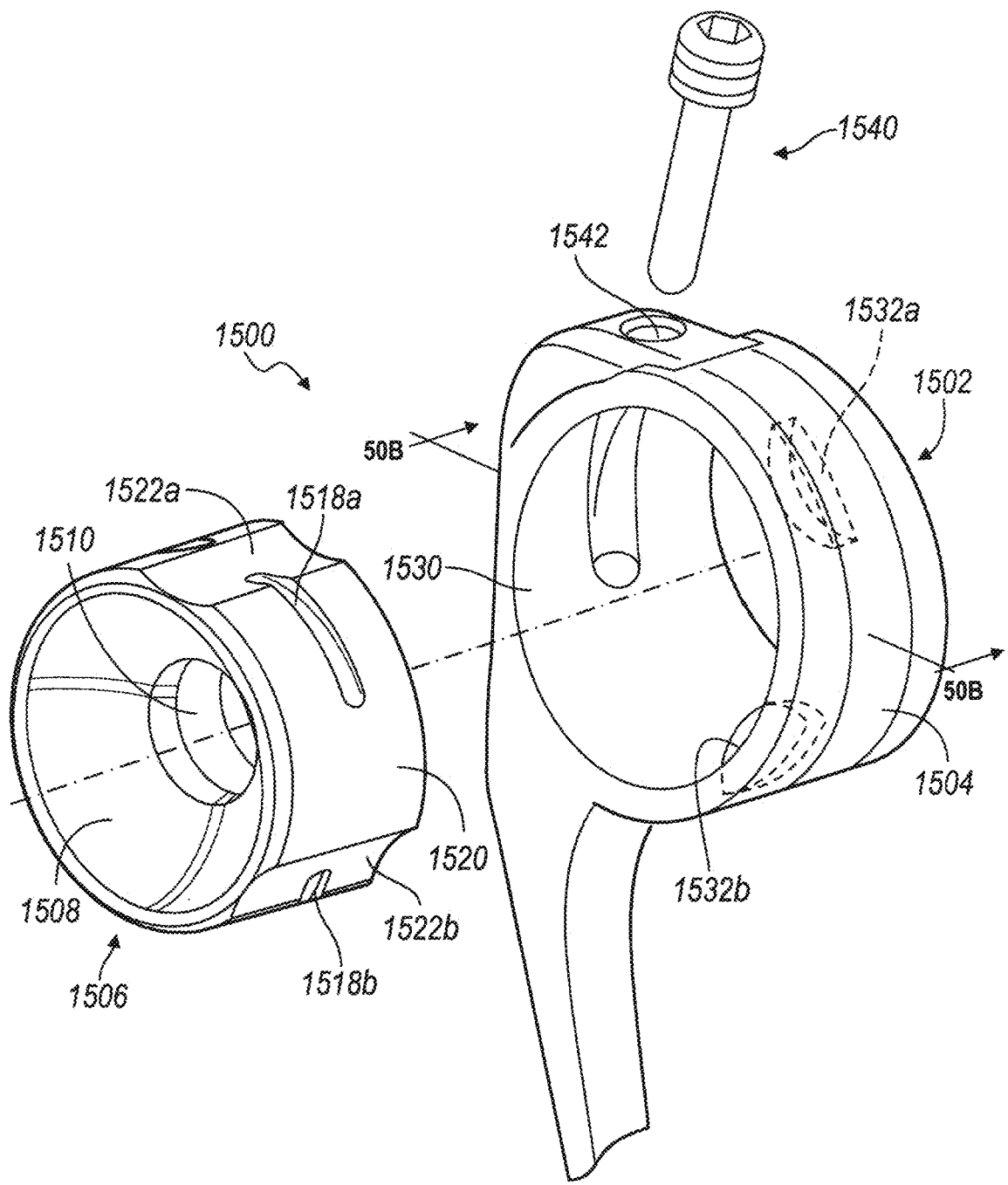
FIG. 48 is an exploded perspective view of a stem structure with modular bearing member.

Grooves or depressions 1426a-1426c are defined within an interior surface or below an interior surface 1428 of the cage 1403. The groove 1426a-1426c can engage or cooperate with the tabs 1410a-1410c, as illustrated in FIG. 47A. The tabs 1410a-1410c can be made to engage or cooperate with the grooves 1426a-1426c by moving the bearing member 1404 into the cage 1403 by positioning or aligning the tabs 1410a with the tab entries 1420a-1420c. The bearing member 1404 can then be rotated in a selected direction, such as the direction indicated by arrow 1429 in FIG. 46, to move the tabs 1410a-1410c within the grooves 1426a-1426c. The direction that the bearing member 1404 is moved can be any appropriate direction, and the direction of arrow 1429 is merely exemplary. The bearing member 1404 is inserted into the cage 1403 in an insertion position and is rotated to an implanted or fixed position.

Once the bearing member 1404 is rotated to a selected or locked position relative to the cage 1403, a locking or set screw 1432 can be positioned in the second stem structure 1400 to fix or hold the bearing member 1404 in the implanted position. The set screw 1432 can pass through or cooperate with a stem passage 1434 to engage or cooperate with a set region 1436 of the bearing member 1404. The set region 1436 can include a cam or other appropriate surface to be engaged or contacted by the set screw 1432.

The set screw 1432 can be positioned to resist rotation of the bearing member 1404. In other words, the set screw can stop the bearing member 1404 from returning to the insertion position, which is contrary to the direction of the arrow 1429. Therefore, the bearing member 1404 can be held within the cage 1403 by the tabs 1410a-1410c cooperating with the respective grooves 1426a-1426c of the cage 1403.

The bearing member 1404, therefore, can be a substantially modular bearing member that is selected for appropriate materials, configurations, sizes, and the like during an implantation procedure. For example, as discussed above, the bearing surfaces 1406 can include a multiple and angled bearing surface portions. A plurality of bearing members 1404 can be provided to include a plurality of angles between respective central axes of the bearing surfaces defining the bearing surface 1406. The user can select the bearing member 1404 prior to or during a procedure based upon the patient's anatomy. Various other purposes for providing modular bearing members 1404 can also be provided and are discussed above.

With reference to FIGS. 48-50B, a second stem assembly 1500, according to various embodiments, is illustrated. The second stem structure 1500 includes a second bearing component 1502 that includes a cage 1504 in a bearing member 1506. The bearing member 1506 can be similar to the bearing member 1404, discussed above, including a bearing surface having multiple bearing surface configurations 1508 and a passage 1510. The bearing member 1506, however, can differ from the bearing member 1404 at least in that bearing member 1506 includes one or a plurality of grooves 1518a-1518b that are part of a holding member or mechanism. The grooves 1518a-1518b can be defined below a surface or defined to extend from an exterior surface 1520 of the bearing member 1506. The bearing member 1506 can also include tab entry regions 1522a-1522b also defined relative to the exterior surface 1520 of the bearing member 1506.

The cage 1504 of the second bearing component 1502 can also be similar to the cage 1403 discussed above. The cage 1504 can include an interior surface 1530 with one or a plurality of tabs 1532a and 1532b that also form part of the holding member or mechanism. The bearing member 1506 is positioned within the cage 1504 by moving the tabs 1532a and 1532b into the tab entry grooves 1522a and 1522b.

Figure 49:
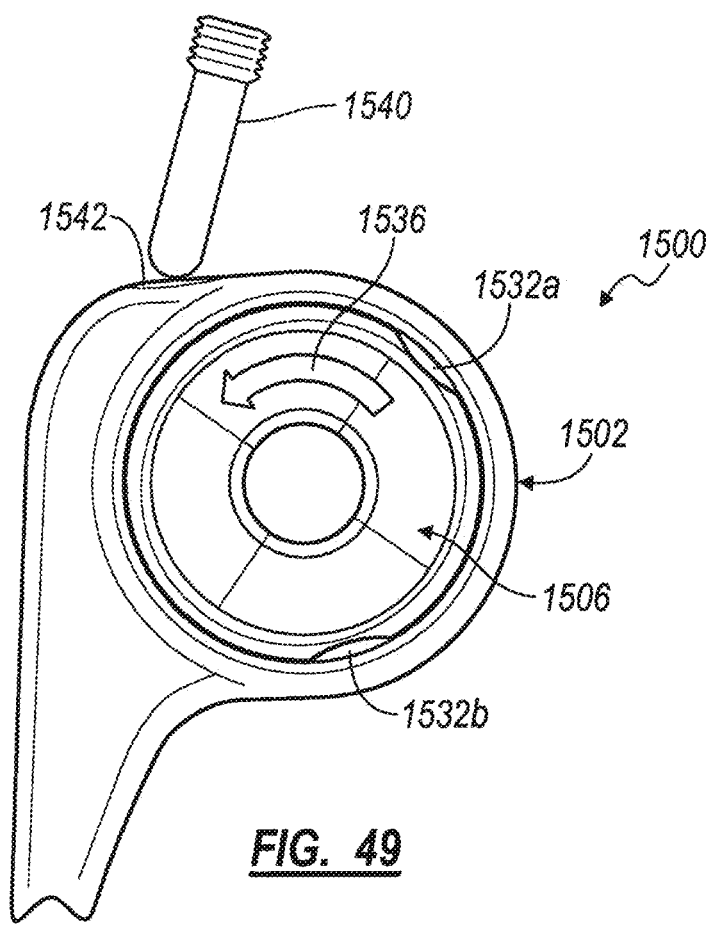
FIG. 49 is a plan view of an assembled stem structure of FIG. 48 in a first orientation.
Figure 50A:
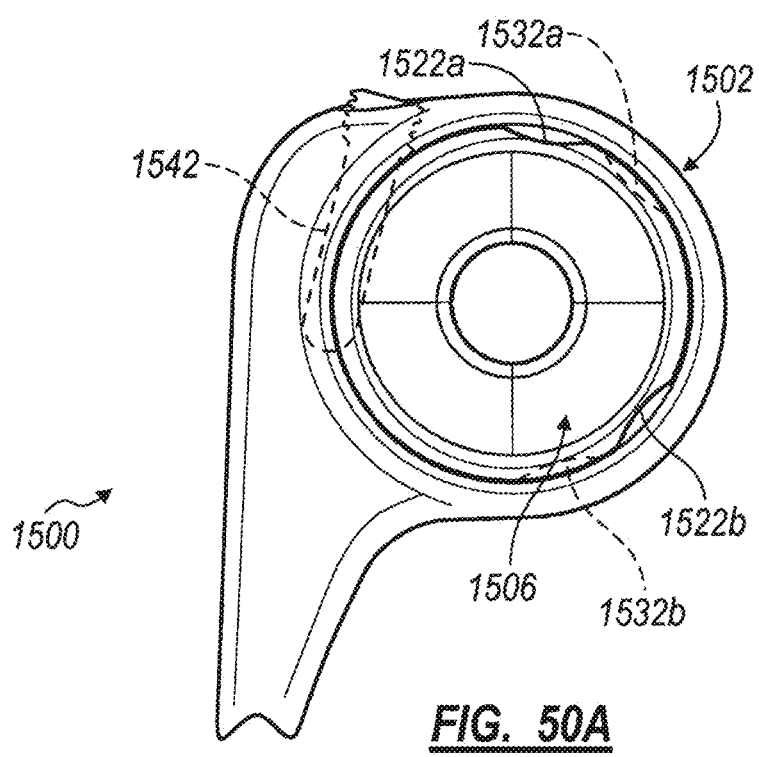
FIG. 50A is a plan view of an assembled stem structure of FIG. 48 in a second orientation.
Figure 50B:
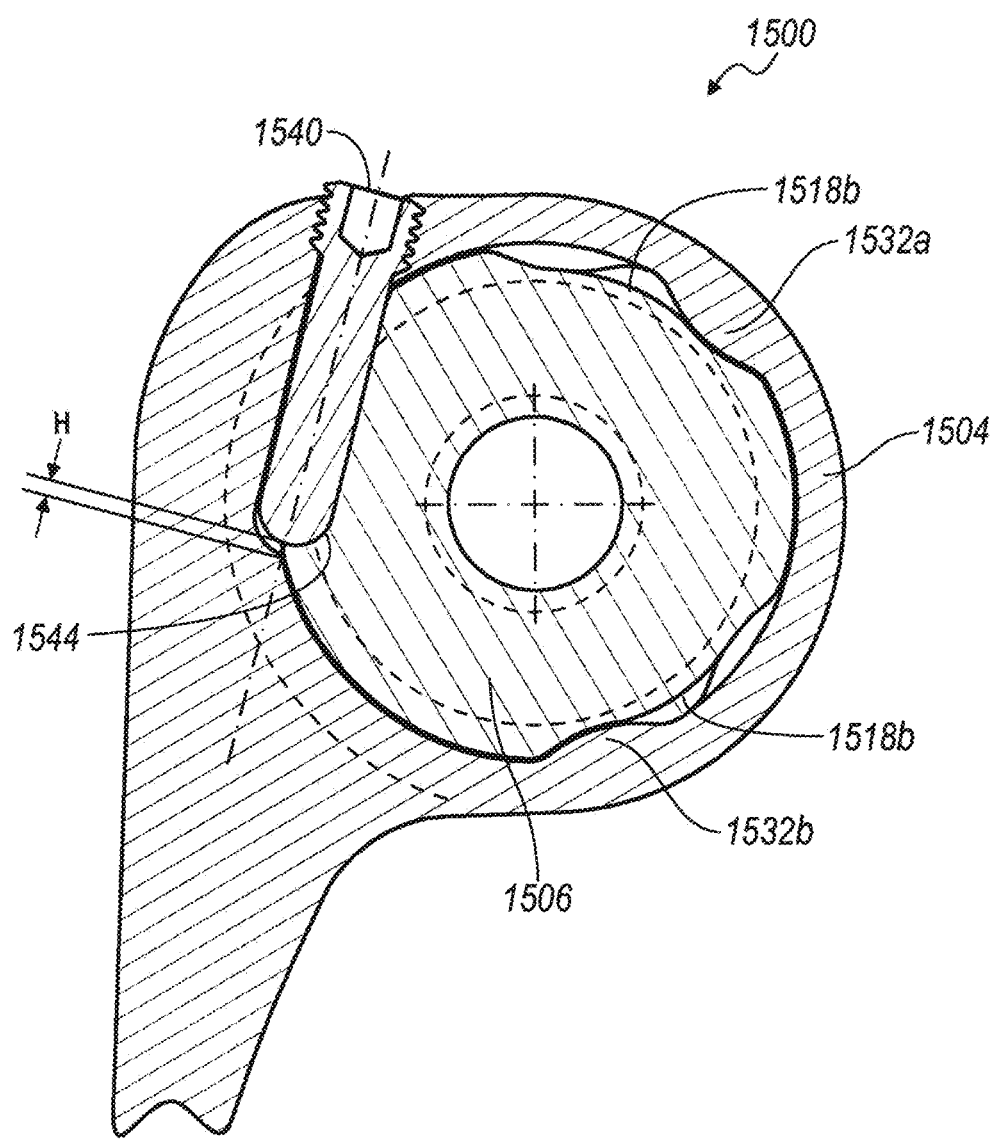
FIG. 50B is a cross-sectional view of the assembled stem structure of FIG. 50A along line 50B-50B.

Once the bearing member 1506 is within the cage 1504, the bearing member 1506 can be rotated in the direction of arrow 1536 illustrated in FIG. 49, resulting in the tabs 1532a-1532b being positioned within the locking or holding grooves 1518a and 1518b, as illustrated in FIGS. 50A and 50B. The bearing member 1506 is inserted into the cage 1504 in an insertion position and then rotated to an implanted or fixed position.

Once the bearing member 1506 is rotated to the selected lock or implanted position, a locking or set screw 1540 can be passed through a passage or opening 1542 to hold or resist the bearing member 1506 from rotating in a direction contrary to the arrow 1536. As discussed and illustrated above in FIG. 47B, the set screw 1432 of the second bearing component 1402 can resist rotation of the bearing member 1404 and assist in holding the bearing member 1404 relative to the cage 1403. Similarly, the set screw 1540 can hold the bearing member 1506 in the selected or implanted position relative to the cage 1504. The bearing member 1506 can then be held within the cage 1504 by the interaction of the tabs 1532a and 1532b with the grooves 1518a and 1518b. Further, in the depicted embodiment, the locking or set screw 1540 can engage surface 1544 to prevent rotation of the bearing member 1506. The locking or set screws, according to various embodiments, can be part of the holding or locking mechanism of the second bearing.

As discussed above, the second stem structure 1500 can be an ulnar stem structure. The bearing surfaces 1508 of the bearing member 1506 can define opposed dual spherical, semi-spherical or partially spherical bearing surfaces. In addition, each of the opposing faces can define a plurality of bearing surfaces that include angled central axes, as discussed above. Accordingly, the second bearing component 1502 can be provided as an ulnar bearing for an elbow prosthesis.

Figure 51:
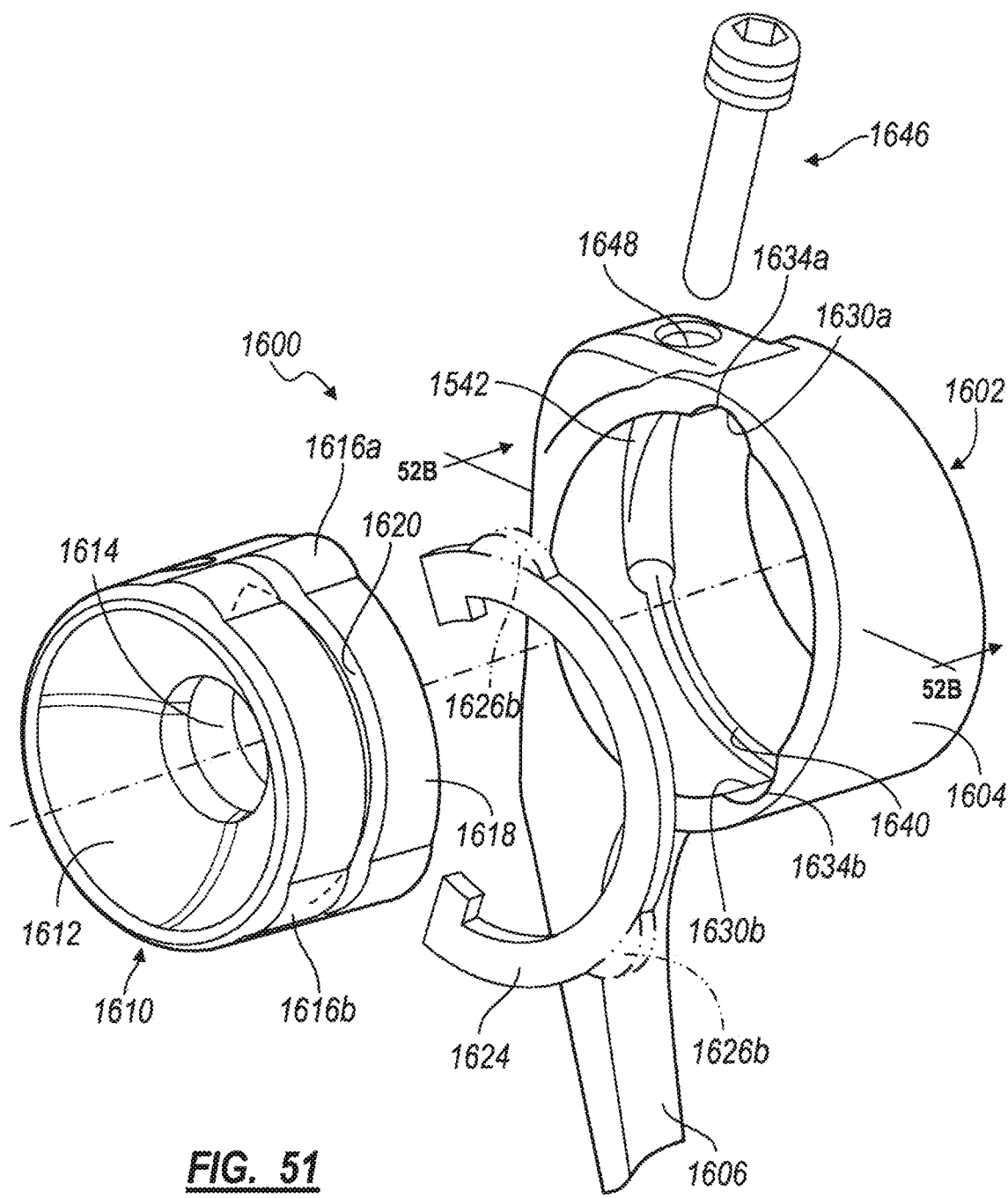
FIG. 51 is an exploded perspective view of a stem structure with modular bearing member.
Figures 52A, 52B:
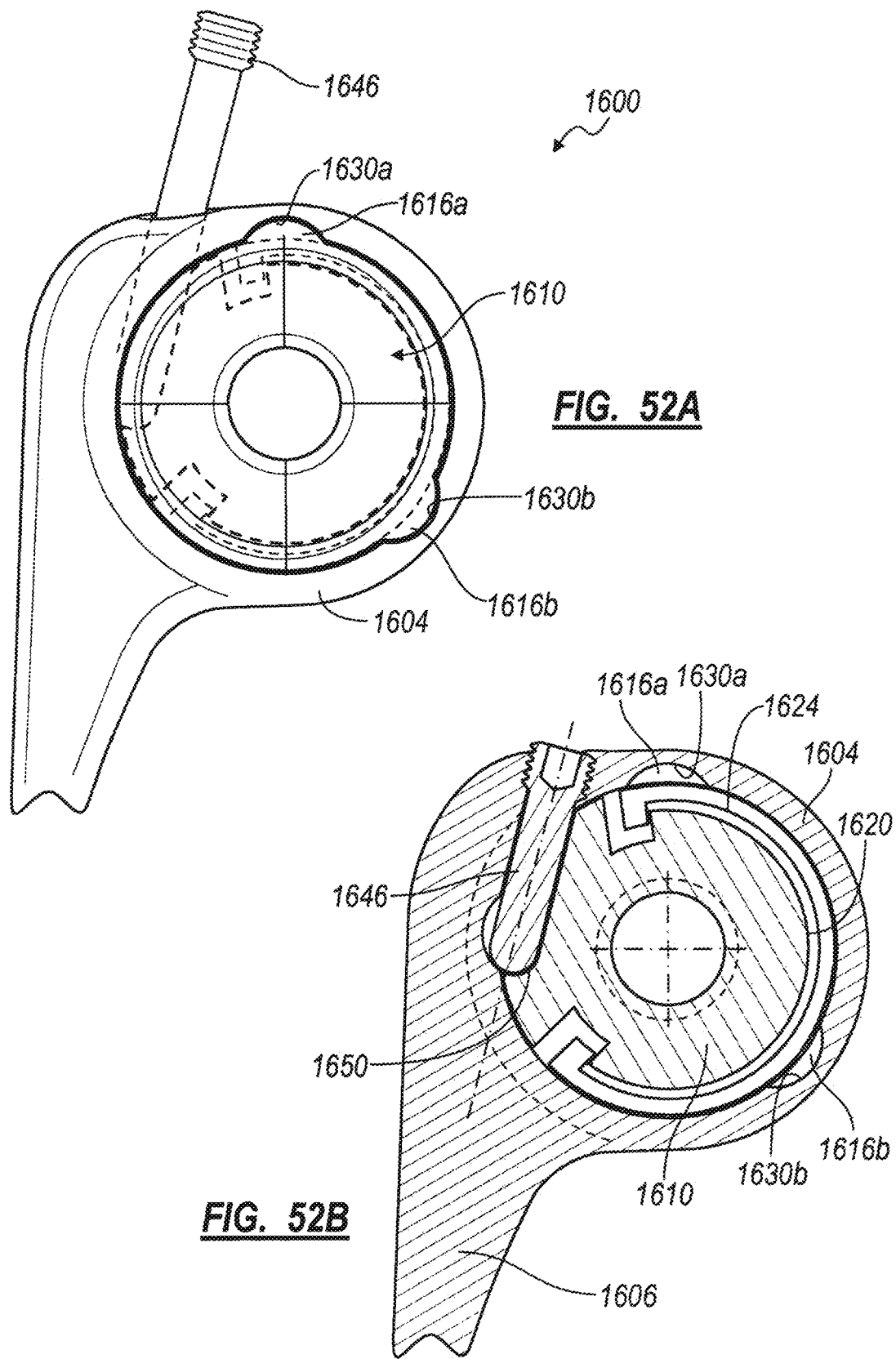
FIG. 52A is a plan view of an assembled stem structure of FIG. 51.
FIG. 52B is a cross-sectional view of the assembled stem structure of FIG. 52A along line 52B-52B.
Figure 53:
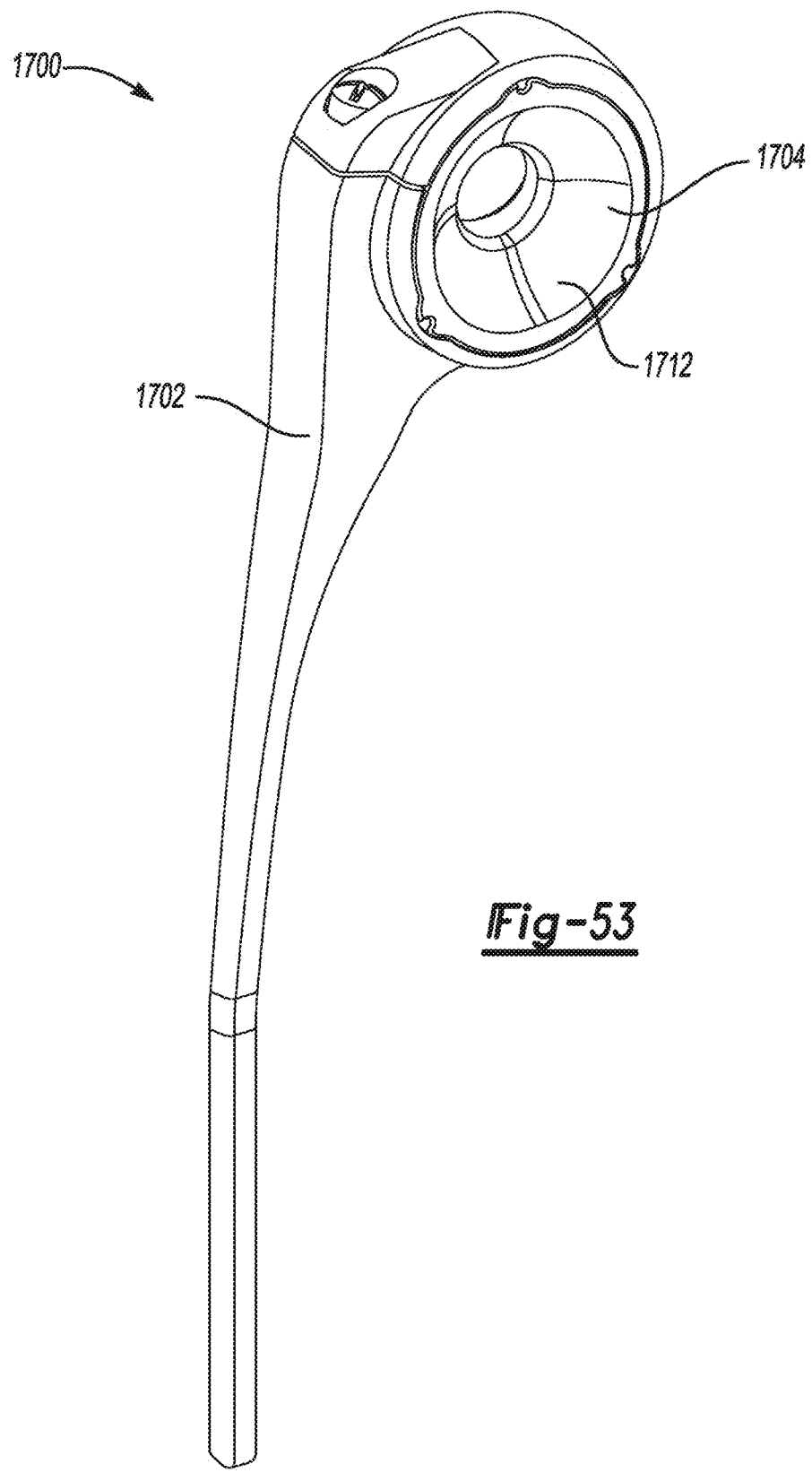
FIG. 53 is a perspective view of a stem assembly constructed in accordance to additional features of the present teachings.
Figure 54:
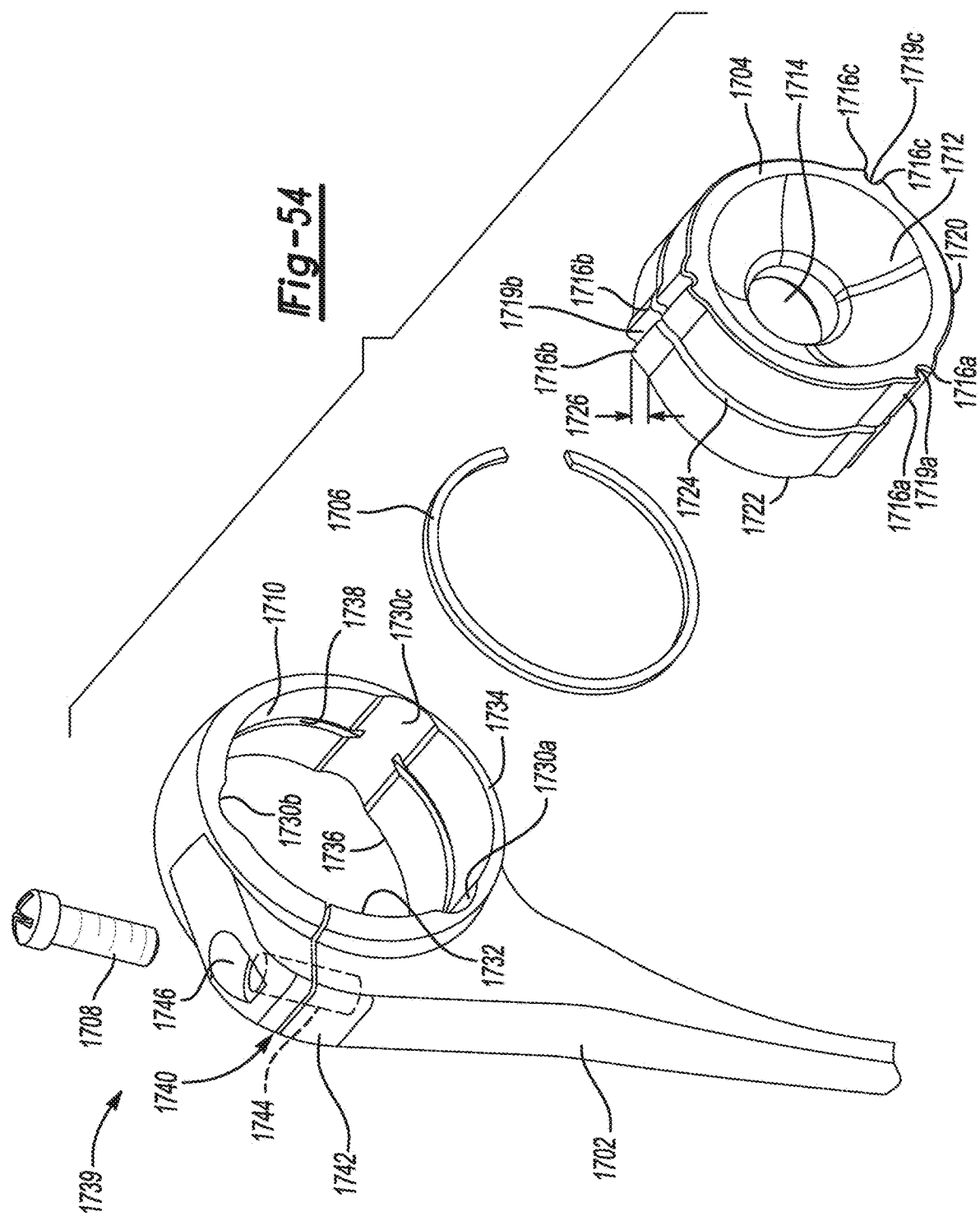
FIG. 54 is an exploded perspective view of the stem assembly of FIG. 53.

With reference to FIGS. 51-52B, a second stem structure 1600 is illustrated. The second stem structure 1600 can be provided as an ulnar prosthesis. The second stem structure 1600 includes a second bearing component 1602 including a cage 1604 interconnected with or affixed to the distal stem portion 1606.

The second bearing components 1602 can further include a bearing member 1610 including selected portions, similar to the portions of the bearing member 1404 discussed above. Generally, the bearing member 1610 can include a bearing surface 1612 or a plurality of bearing surfaces, such as opposed at least partially spherical bearing surfaces. The bearing member 1610 can further define a passage or bore 1614.

The bearing member 1610 includes one or more anti-rotation projections 1616a and 1616b. Anti-rotation projection 1616a and 1616b can project from an exterior surface 1618 of the bearing member 1610. The exterior surface 1618 of the bearing member 1610 includes groove 1620. The groove 1620 can cooperate or hold a locking or fixation ring 1624 relative to the bearing member 1610. The groove 1620 and the locking ring 1624 are a holding member or mechanism to assist in holding the bearing member 1610 within the cage 1604. The locking ring 1624 can also optionally include anti-rotation projections 1626a and 1626b.

Either the anti-rotation projections 1616a and 1616b or the anti-rotation projections 1626a and 1626b, can engage anti-rotation depressions or grooves 1630a and 1630b included in an interior surface 1632 of the cage 1604. Passage or entry region 1634a and 1634b can also be defined in a sidewall of the cage 1604. The interior surface 1632 includes a locking or fixation groove 1640 can also forms part of the holding member or mechanism.

The bearing member 1610 can be positioned in the cage 1604 before or after the locking ring 1624 is positioned within the groove 1620 of the bearing member 1610. According to various embodiments, however, the locking ring 1624 can be positioned within the locking ring groove 1620. The locking ring 1624 can then be compressed prior to or during movement of the bearing member 1610 and locking ring 1624 into the cage 1604. When the locking ring 1624 engages or is positioned near the groove 1640, the locking ring 1624 can relax or expand to engage at least a portion of or move into a portion of a groove 1640.

The locking ring 1624 has a ring thickness 1644 allowing a first portion of the ring 1624 to be positioned within the groove 1640 and a second portion of the ring 1624 to be positioned within the groove 1620 substantially simultaneously. By positioning the locking ring 1624 in both of the grooves 1620 and 1640, the locking ring 1624 holds the bearing member 1610 within the cage 1604. Thus, the locking ring 1624, alone, can be provided to hold the bearing member 1610 in the cage 1604. Other holding mechanisms can, however, be provided.

The anti-rotation projections, such as the anti-rotation projection 1616a and 1616b, can assist in minimizing or eliminating rotation of the bearing member 1610 within the cage 1604. A set or locking screw 1646 can, however, also be positioned within a passage 1648 defined in the second stem structure 1600 to engage an anti-rotation cam or surface 1650 of the bearing member 1610. The set screw 1646 can also work as the holding member or mechanism. In this way, the bearing member 1610 can be held, with respect to the cage 1604, both transversely, preventing movement out of the cage 1604, and rotationally once the bearing member 1610 is positioned within the cage 1604.

As discussed above, the bearing member 1610 can be provide as an ulnar bearing member, and the second stem assembly 1600 can be provided as an ulnar prosthesis for implantation into a human patient. Accordingly, the bearing member 1610 can include the various features, discussed above. In addition, bearing member 1610 is modular or separate from the cage 1604 and can provide for flexibility and selection by the user during a procedure. For example, the kit can include a plurality of the bearing members 1610 each including different characteristics, such as different bearing surfaces defined around central axes at varying angles. The user can then select the appropriate bearing member for implantation into the patient. Additionally, the modular members or portions allow for trialing to determine or achieve the best or optimum configuration of a prosthesis during an operative procedure.

It will be understood that first and second stem structures and bearing components are described according to various embodiments. The various stem structures, however, can also be combined in selected and appropriate manners for a selected procedure. Thus, each stem structure can be augmented to include any or all features discussed above. Similarly, each of the bearing components can be augments to include any or all of the features discussed above.

With reference now to FIGS. 53-59, a linked stem assembly 1700 according to additional features is shown. The stem assembly 1700 can include an ulna stem component 1702, a bearing member 1704, a ring member 1706 (FIG. 54) and a fastener 1708. The ulna stem component 1702 can include an annular cage or enclosed structure 1710 that can couple with or hold the bearing member 1704 in a selected position. The bearing member 1704 can have a bearing surface 1712 that can include two faces or opposing partially- or semi-spherical bearing surfaces. A throughbore or passage 1714 can also be defined through the bearing member 1704. The bearing surfaces 1712 and the passage 1714 can have any appropriate configuration, including those discussed above. In one example, the bearing surface 1712 can include two opposed bearing sections defined around axes that are at an angle relative to one another.

The bearing member 1704 can include radially extending tabs 1716a-1716c formed on an exterior surface 1718. In one example, the tabs 1716a-1716c can extend to medial and lateral edges 1720 and 1722, respectively, of the bearing member 1704. Each tab 1716a, 1716b and 1716c are collectively defined by a pair of tabs 1716a, 1716b and 1716c separated by a depression 1719a, 1719b and 1719c, respectively. A groove 1724 can be formed around the outer diameter of the bearing member 1704. In one example, the groove 1724 can be generally centered between the medial and lateral edges 1720 and 1722 of the bearing member 1704. As will become appreciated, the groove 1724 is configured to at least partially receive the ring member 1706. The tabs 1716a-1716c can be positioned 120° apart around the bearing member 1704. The tabs 1716a-1716c can extend at a height 1726 above the exterior surface 1718 of the bearing member 1704. The bearing member 1704 can be formed of ultra high molecular weight polyethylene (UHMWPE) or polyetheretherketone (PEEK).

The tabs 1716a-1716c can pass through corresponding tab entries 1730a-1730c formed in a sidewall 1732 of the annular cage 1710. The sidewall 1732 can extend between a medial edge 1734 and a lateral edge 1736 of the annular cage 1710. A groove 1738 can be formed concentrically around the inner diameter or sidewall 1732 of the annular cage 1710. In one example, the groove 1738 can be generally centered between the medial edge 1734 and the lateral edge 1736. As will be discussed herein, the bearing member 1704 can be held within the annular cage 1710 with the ring member 1706 partially nesting into the groove 1724 provided on the bearing member 1704 and the groove 1738 provided on the annular cage 1710.

The ulna stem component 1702 can include a radially compressible locking mechanism 1739. The radially compressible locking mechanism 1739 includes a disconnect or cut 1740 formed completely through the annular cage structure 1710 from an outer surface 1742 to the sidewall 1732. In one example, the cut 1740 can be machined in a subsequent step after machining the ulna stem component 1702. The radially compressible locking mechanism 1739 can also include a threaded fastener passage 1744 that is provided in the ulna stem component 1702 and traverses the cut 1740. A counter-bore 1746 can be formed on the ulna stem component 1702 for nestingly receiving the fastener 1708. As will become appreciated from the following discussion, the annular cage 1710 is configured to slightly expand the sidewall 1732 radially outwardly during assembly of the bearing member 1704 and subsequently retract radially inwardly upon advancement of the fastener 1708 through the fastener passage 1744 in the assembled position.

With specific reference to FIGS. 55-59, an exemplary method of assembling the bearing member 1704 into the annular cage 1710 of the ulna stem component 1702 will now be discussed. Initially, the bearing member 1704 can be selected from a group or kit of bearing members, such that an appropriate material, configuration, size and other material or geometrical considerations can be satisfied. For example, as discussed above, the bearing surfaces 1712 can include a multiple and angled bearing surface portion. A plurality of bearing members 1704 can be provided to include a plurality of angles between respective central axes of the bearing surfaces defining the bearing surface 1712. The user can select the bearing member 1704 prior to or during a procedure based upon the patient's anatomy. Various other purposes for providing modular bearing members 1704 can also be provided and are discussed above.

Figure 57:
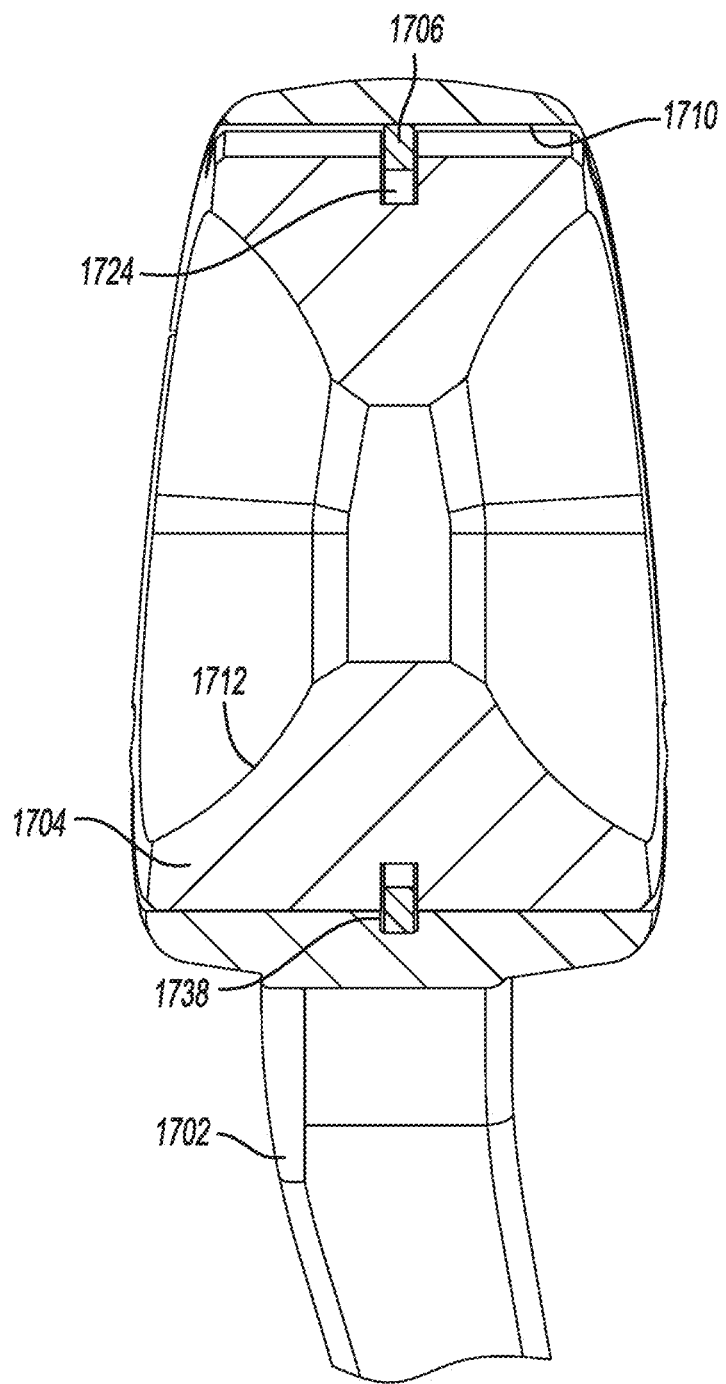
FIG. 57 is a cross-sectional view of the stem assembly of FIGS. 55 and 56 and shown with the bearing in an assembled position relative to the stem component.

Once the desired bearing member 1704 has been selected, the ring member 1706 can be positioned at least partially into the groove 1724 formed on the bearing member 1704 (FIG. 55). In some examples, the ring member 1706 can be slightly expanded radially outwardly to advance past the tabs 1716a-1716c until reaching a location aligned with the groove 1724. Next, a surgeon can positively align the tabs 1716a-1716c of the bearing member 1704 with the tab entries 1730a-1730c of the ulna stem component 1702. The lateral edge 1722 of the bearing member 1704 can then be advanced past the medial edge 1734 of the ulna stem component 1702 until a position where the ring member 1706 comes into contact with the medial edge 1734 of the ulna stem component 1702. At this point, a surgeon can compress manually the ring member 1706 further into the groove 1724 on the bearing member 1704 and/or, continue to advance the bearing member 1704 into the annular cage 1710 causing the ring member 1706 to compress further into the groove 1724 and reach an outer diameter that is generally less than the inner diameter of the sidewall 1732 (FIG. 56). The bearing member 1704 is then further advanced into the annular cage 1710 until reaching a position where the ring member 1706 aligns with the groove 1738 formed around the sidewall 1732 of the annular cage 1710. Once the ring member 1706 aligns with the groove 1738 on the sidewall 1732, the ring member 1706 will expand radially outwardly to its original static position where at least a portion of the ring member 1706 extends into the groove 1738 of the annular cage 1710 and at least partially extends into the groove 1724 of the bearing member 1704 (FIG. 57).

Figure 59:
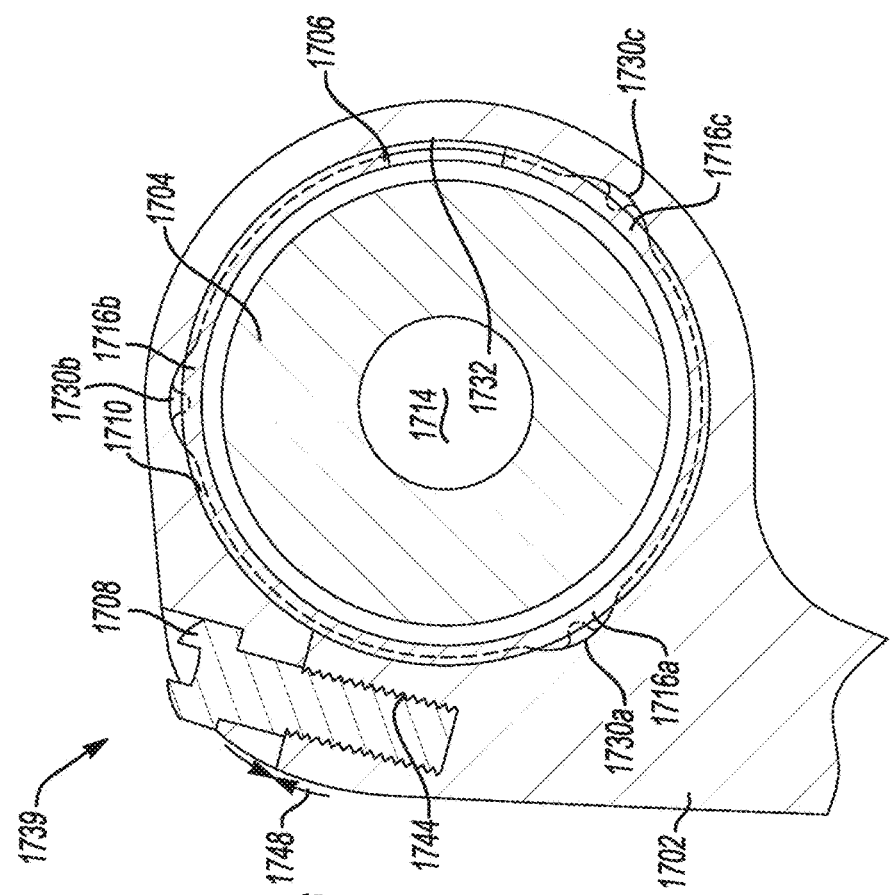
FIG. 59 is a cross-sectional view of the stem assembly of FIG. 58 and shown with the fastener threadably assembled.
Figure 58:
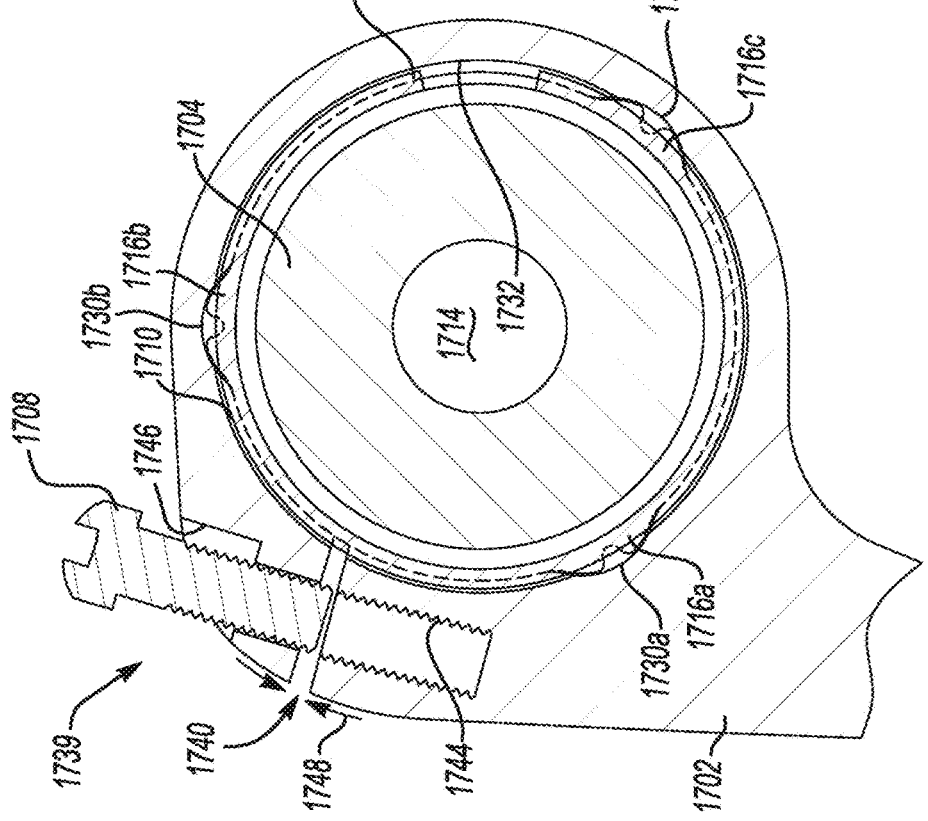
FIG. 58 is a cross-sectional view of the stem assembly prior to insertion of a fastener into the stem component.
Figure 62:
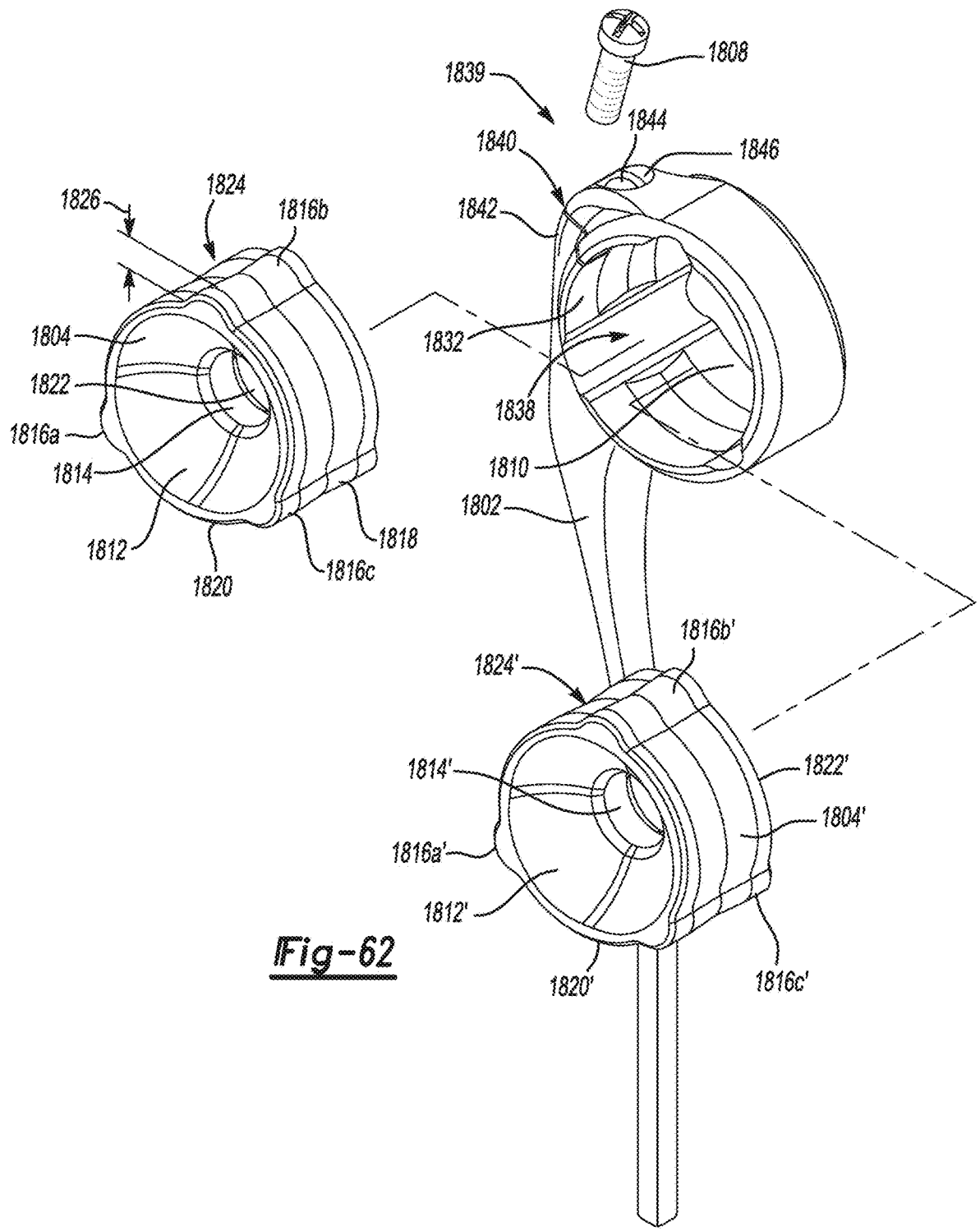
FIG. 62 is an exploded perspective view of the stem assembly of FIG. 61 and shown with an alternate bearing.

Next, with specific reference to FIGS. 58 and 59, the radially compressible locking mechanism 1739 will be further described. The fastener 1708 is threadably advanced into the fastener passage 1744 of the ulna stem component 1702. Threadable advancement of the fastener 1708 into the fastener passage 1744 causes the inner diameter of the sidewall 1732 to be reduced as a gap 1748 defined by opposing sidewalls of the cut 1740 closes. Once the fastener 1708 has been advanced sufficiently to close the gap provided by the cut 1740, the ring member 1706 becomes further nested within each of the grooves 1724 and 1738 of the bearing member 1704 and the annular cage 1710, respectively. In the assembled position, the ring member 1706 inhibits medial/lateral motion of the bearing member 1704 relative to the sidewall 1732 of the annular cage 1710. Additionally, the tabs 1716a-1716c of the bearing member 1704 cooperate with the tab entries 1730a-1730c to inhibit rotational motion of the bearing member 1704 within the annular cage 1710. The stem assembly 1700 can be used in conjunction with any of the bearing and/or stem components described herein. While the radially compressible locking mechanism 1739 has been described as compressing the annular cage 1710 by advancement of the fastener 1708 into the fastener passage 1744, other configurations and mechanisms may be employed to compress the annular cage 1710 around the bearing member 1704.

With reference now to FIG. 60, an ulna stem component 1702' constructed in accordance to additional features of the present teachings will now be described. Unless otherwise described, the ulna stem component 1702' is constructed similarly to the ulna stem component 1702 discussed above with respect to FIGS. 54-59. The ulna stem component 1702 can include an annular cage or enclosed structure 1710' that can couple with or hold the bearing member 1704 (not specifically shown in this figure) in a selected position. The annular cage 1710' can have an inner cylindrical sidewall 1732' that extends between a medial edge 1734' and a lateral edge 1736'. The ulna stem component 1702' can have a disconnect or cut 1740' that is formed completely through the annular cage structure 1710' from an outer surface 1742' to the sidewall 1732'. The cut 1740' of the ulna stem component 1702' has a V-shaped profile. The V-shaped profile decreases shear loads experienced on the ulna stem component 1702'. In this way, any shear loads experienced between a bearing member 1704 assembled in the annular cage 1710' and the ulna stem component 1702' can be taken up by not only the fastener 1708 but by the structure of the ulna stem component 1702' as a result of the opposing surfaces created by the V-shaped profile in the cut 1740'. It will be appreciated that the cut 1740' having the V-shaped profile can be included on any of the ulna stem components disclosed herein.

With reference now to FIGS. 61-67, a linked stem assembly 1800 according to additional features is shown. The stem assembly 1800 can include an ulna stem component 1802, a bearing member 1804, and a fastener 1808. The ulna stem component 1802 can include an annular cage or enclosed structure 1810 that can couple with or hold the bearing member 1804 (or the bearing member 1804') in a selected position. The bearing member 1804 can have a bearing surface 1812 that can include two faces or opposing partially- or semi-spherical bearing surfaces. The throughbore or passage 1814 can also be defined through the bearing member 1804. The bearing surfaces 1812 and the passage 1814 can have any appropriate configuration, including those discussed above. In one example, the bearing surface 1812 can include two bearing sections defined around axes that are at an angle relative to one another. The bearing member 1804' can have similar features as the bearing member 1804. In this way, similar features are simply identified with a "prime" suffix on the reference numeral.

The bearing member 1804 can include tabs 1816a-1816c formed on an exterior surface 1818. In one example, the tabs 1816a-1816c can extend to medial and lateral edges 1820 and 1822, respectively, of the bearing member 1804. A radial depression 1824 can be formed around the outer diameter of the bearing member 1804. In one example, the radial depression 1824 can be in the form of a negative V-shape. The tabs 1816a-1816c can radially extend at a height 1826 above the exterior surface 1818 of the bearing member 1804. The bearing member 1804 can be formed of ultra high molecular weight polyethylene (UHMWPE) or polyetheretherketone (PEEK).

The tabs 1816a-1816c can pass through tab entries 1830a-1830c formed in a sidewall 1832 of the cage 1810 and rest therein. The sidewall 1832 can extend between a medial edge 1834 and a lateral edge 1836 of the cage 1810. A radial protrusion 1838 can be formed around the inner diameter or sidewall 1832 of the cage 1810. In one example, the radial protrusion 1838 can be in the form of a positive V-shape. In one example, the radial protrusion 1838 can be generally centered between the medial edge 1834 and the lateral edge 1836. As will be described herein, the radial depression 1824 formed on the bearing member 1804 can nestingly receive the radial protrusion 1838 formed on the sidewall 1832 of the cage 1810 to positively locate the bearing member 1804 inside the cage 1810.

The ulna stem component 1802 can include a radially compressible locking mechanism 1839. The radially compressible locking mechanism 1839 includes a disconnect or cut 1840 formed completely through the annular cage structure 1810 from an outer surface 1842 to the sidewall 1832. Again, the cut 1749 may be formed through the cage structure 1810 by a supplemental machining step. The radially compressible locking mechanism 1839 can include a threaded fastener passage 1844 that is provided in the ulna stem component 1802 and traverses the cut 1749. A counterbore 1846 can be formed on the ulna stem component 1802 for nestingly receiving the fastener 1808. As will become appreciated from the following discussion, the cage 1810 is configured to slightly expand the sidewall 1832 radially outwardly during assembly of the bearing member 1804 and subsequently retract radially inwardly upon advancement of the fastener 1808 through the fastener passage 1844 in the assembled position.

Figure 65:
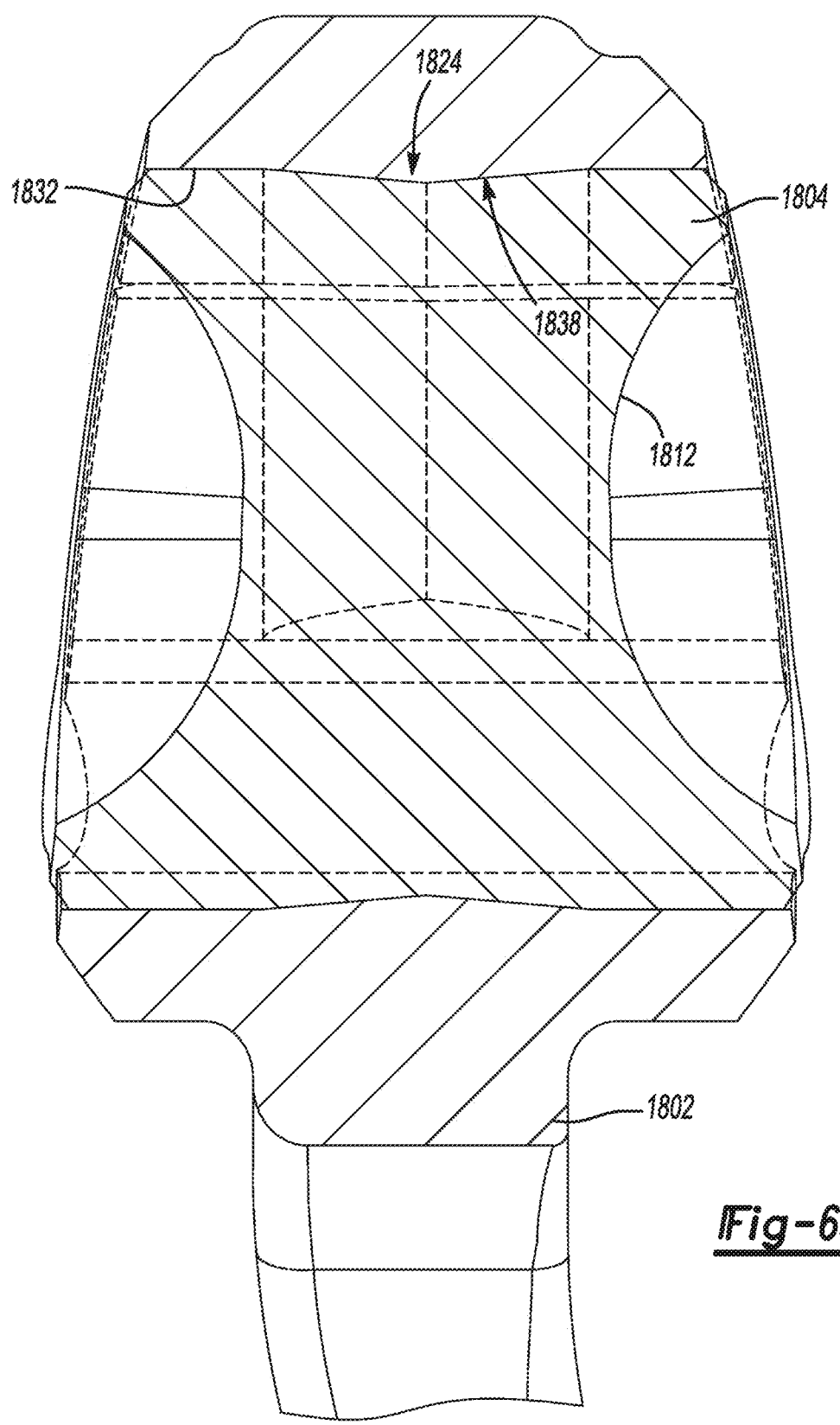
FIG. 65 is a cross-sectional view of the bearing and stem component of FIGS. 63 and 64 and shown with the bearing in an assembled position relative to the stem component.
Figure 68:
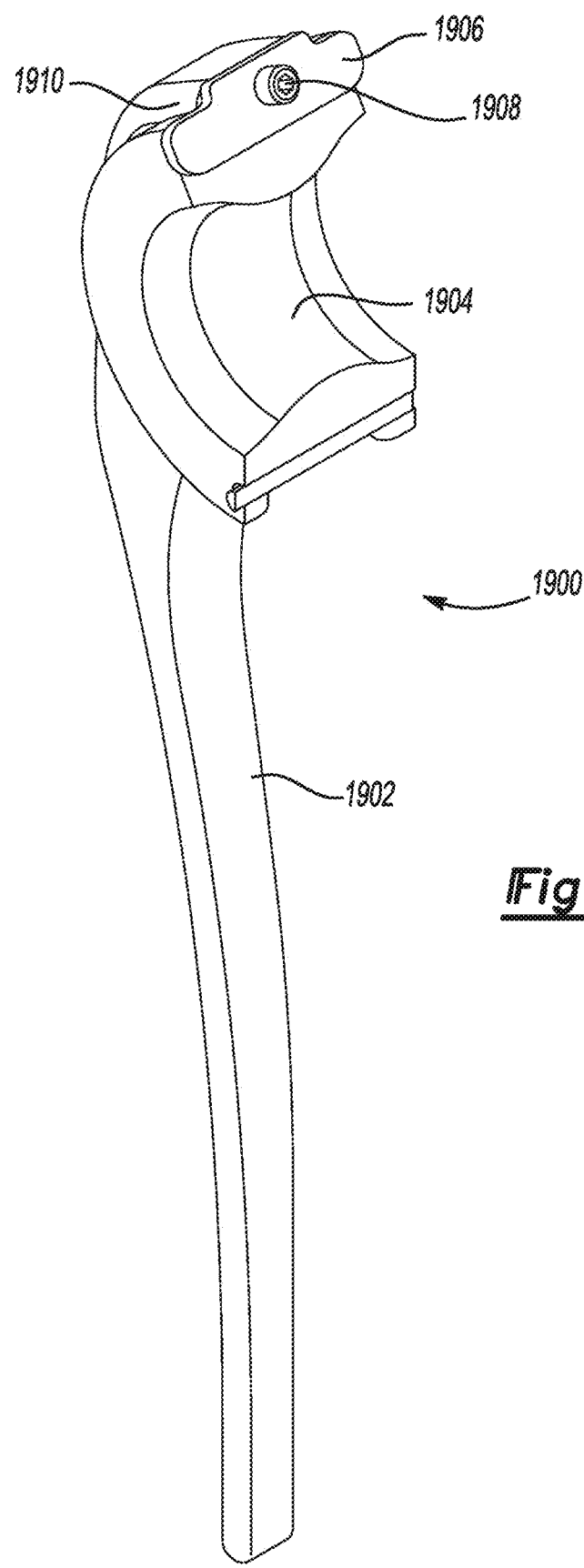
FIG. 68 is a perspective view of a modular unlinked ulnar stem assembly constructed in accordance to one example of the present teachings.

With specific reference now to FIGS. 63-65, an exemplary method of assembling the bearing member 1804 into the cage 1810 of the ulna stem component 1802 will be discussed. Initially, the bearing member 1804 can be selected from a group or kit of bearing members (such as including the bearing member 1804'), such that an appropriate material, configuration, size and other material or geometrical considerations can be satisfied. For example, as discussed above, the bearing surfaces 1812 can include a multiple and angled bearing surface portion. A plurality of bearing members 1804 can be provided to include a plurality of angles between respective central axes of the bearing surfaces defining the bearing surface 1812. The user can select the bearing member 1804 prior to or during a procedure based upon the patient's anatomy. Various other purposes for providing modular bearing members 1804 can also be provided and are discussed above.

Once the desired bearing member 1804 has been selected, a surgeon can align the tabs 1816a-1816c of the bearing member 1804 with the tab entries 1830a-1830c of the ulna stem component 1802. The lateral edge 1822 of the bearing member 1804 can then be advanced passed the medial edge 1834 of the ulna stem component 1802 until a position where the radial protrusion 1838 of the cage 1810 is aligned with the radial depression 1824 of the bearing member 1804. Because the radial protrusion 1838 is in the form of a positive V-shape and the radial depression 1824 is in the form of a complementary negative V-shape, a user is given positive tactile feedback when the radial protrusion 1838 is satisfactorily received into the radial depression 1824 of the bearing member 1804. It will be appreciated by those skilled in the art that while the radial depression 1824 has been described as being provided on the bearing member 1804 and the radial protrusion 1838 has been described as being provided on the cage 1810, the respective depression and protrusion may be located on opposite components. Furthermore, while the respective depression 1824 and protrusion 1838 have been illustrated and described as having a V-shape geometry, other geometries may be provided that can establish a complementary interlocking profile.

Next, with specific reference to FIGS. 66 and 67, the radially compressible locking mechanism 1839 will be further described. The fastener 1808 can be threadably advanced into the fastener passage 1844 of the ulna stem component 1802. Threadable advancement of the fastener 1808 into the fastener passage 1844 causes the inner diameter of the sidewall 1832 to be reduced as a gap 1848 defined by the cut 1840 closes. Once the fastener 1808 has been advanced sufficiently to close the gap provided by the cut 1840, the bearing member 1804 is further secured in a confined position within the cage 1810. In the assembled position, the interface between the radial depression 1824 and the radial protrusion 1838 inhibits medial/lateral motion of the bearing member 1804 relative to the sidewall 1832 of the cage 1810. Additionally, the tabs 1816a-1816c of the bearing member 1804 cooperate with the tab entries 1830a-1830c to inhibit rotational motion of the bearing member 1804 within the cage 1810. The stem assembly 1800 can be used in conjunction with any of the bearing and/or stem components described herein. While the radially compressible locking mechanism 1839 has been described as compressing the cage 1810 by advancement of the fastener 1808 into the fastener passage 1844, other configurations and mechanisms may be employed to compress the cage 1810 around the bearing member 1804.

With reference now to FIGS. 68-72, a modular unlinked ulnar stem assembly 1900 according to one example of the present teachings will be described. In general, the modular unlinked ulnar stem assembly 1900 can include a stem 1902, an articulating component 1904, a plate 1906 and a fastener 1908. As will become appreciated from the following discussion, the articulating component 1904 can be modular such that a series of articulating components can be provided that are selectively attachable to the stem 1902 according to a specific patient's needs. The modular unlinked ulnar stem assembly 1900 can be favorable in some circumstances as it has the potential to remove less native bone than other elbow prostheses such as a semi-constrained total elbow, for example. Furthermore, the modular unlinked ulnar stem assembly 1900 can be favorable in circumstances where one side of the elbow joint includes satisfactory bone and/or cartilage and it is only desirable to replace the other side of the elbow joint.

Figure 69:
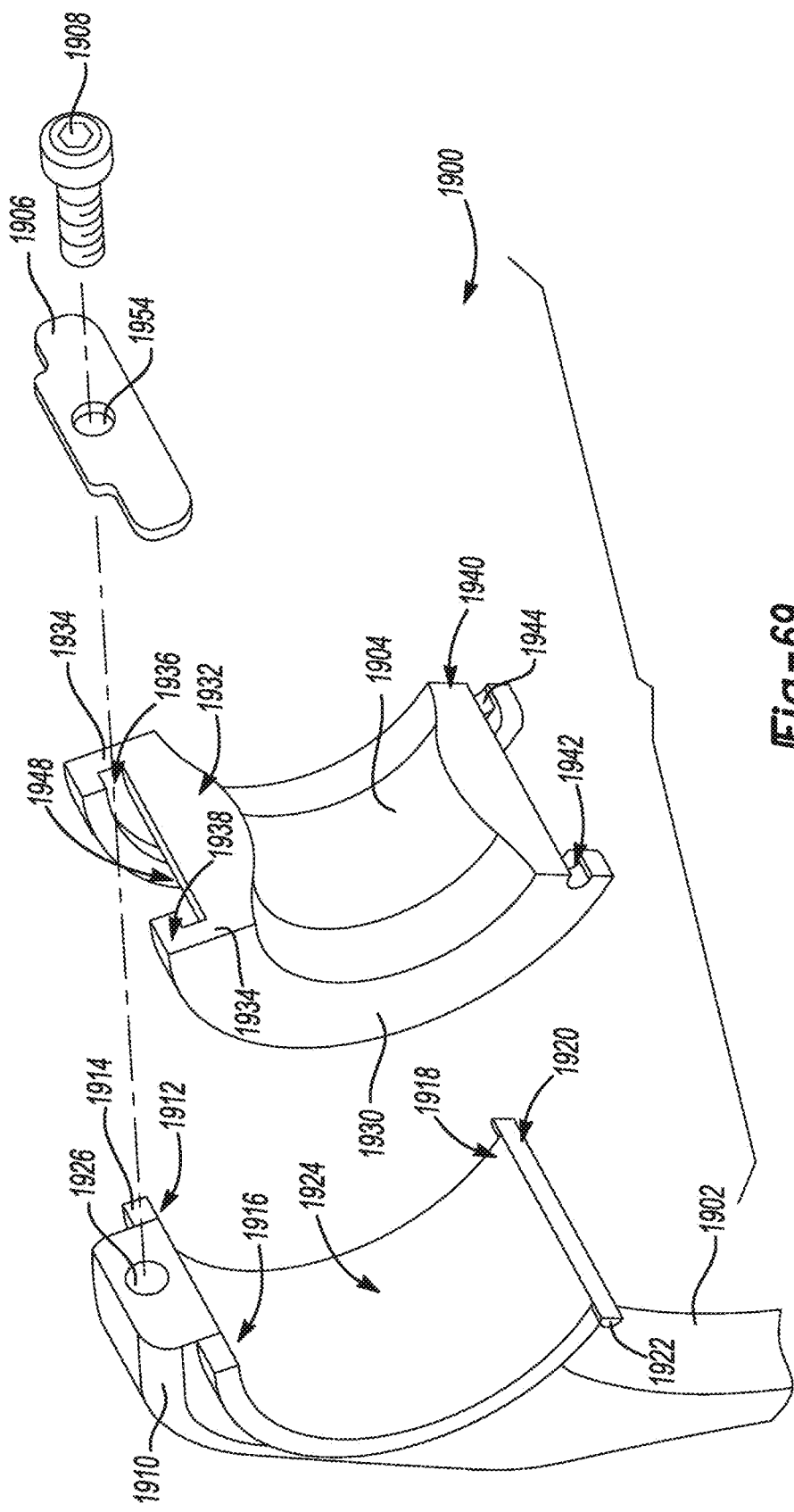
FIG. 69 is an exploded perspective view of portions of the ulnar stem assembly of FIG. 68.

With specific reference now to FIG. 69, exemplary features of the stem 1902 will be described. The stem 1902 can generally include an ulnar ring 1910 that is in the form of a partial or semi-circular cylinder. The stem 1902 can further comprise a first retaining mechanism 1912 having laterally extending rails 1914 that extend around the ulnar ring 1910 from a first end 1916 to a second end 1918. The second end 1918 of the rails 1914 can include a stop 1920 that has a pair of outwardly extending stop surfaces 1922. The ulnar ring 1910 can also include a concave slide surface 1924 and a threaded bore 1926 formed thereon.

With continued reference to FIG. 69, the articulating component 1904 will be described in greater detail. In general, the articulating component 1904 can include a body 1930 that generally takes the shape of a partial or semi-circular cylinder complementary to the shape of the ulnar ring 1910. The articulating component 1904 includes a second retaining mechanism 1932 having a pair of lateral walls 1934 that cooperate to define a semi-circular arcuate channel 1936. The lateral walls 1934 extend from a first end 1938 to a second end 1940. A pair of catches 1942 are formed at the respective second ends 1940 of the arms 1934.

The catches 1942 have catch surfaces 1944. The articulating component 1904 includes a convex slide surface 1948 that extends between the respective lateral arms 1934. The articulating component 1904 can be formed of ultra high molecular weight polyethylene (UHMWPE) or polyetheretherketone (PEEK).

Figure 72:
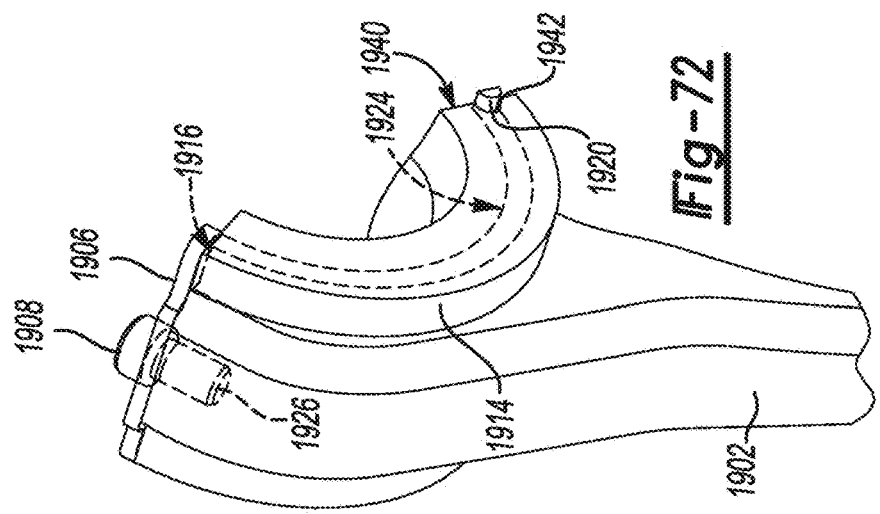
FIGS. 70-72 is an assembly sequence showing an articulating component or bearing being selectively secured to the stem component.
Figure 71:
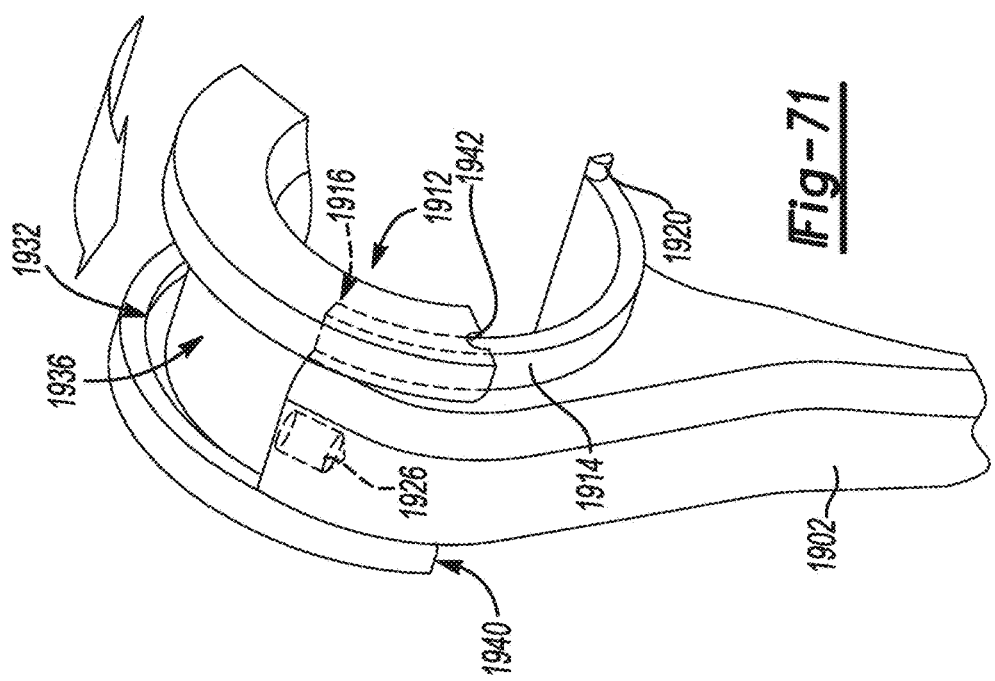
Figure 70:
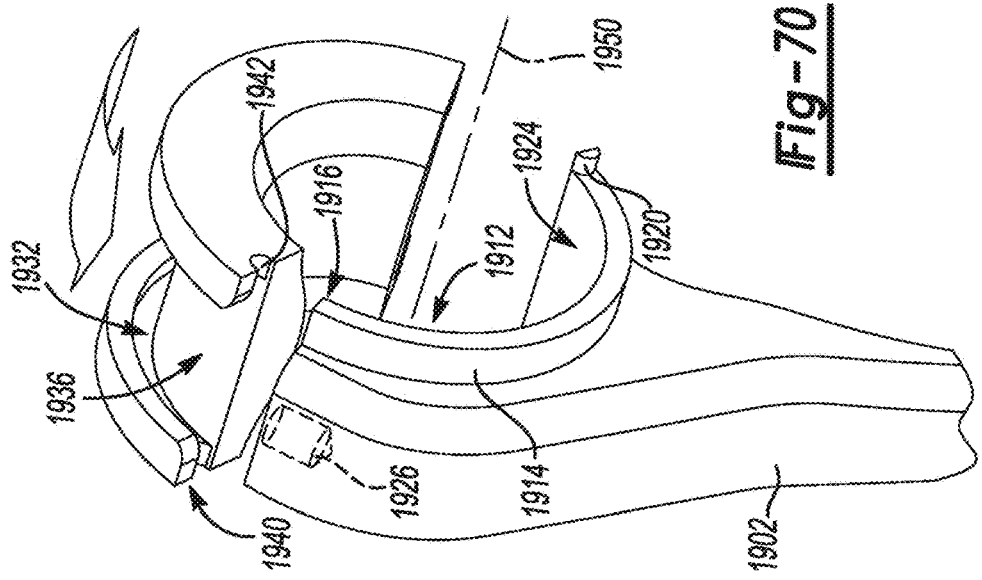
Figure 73:
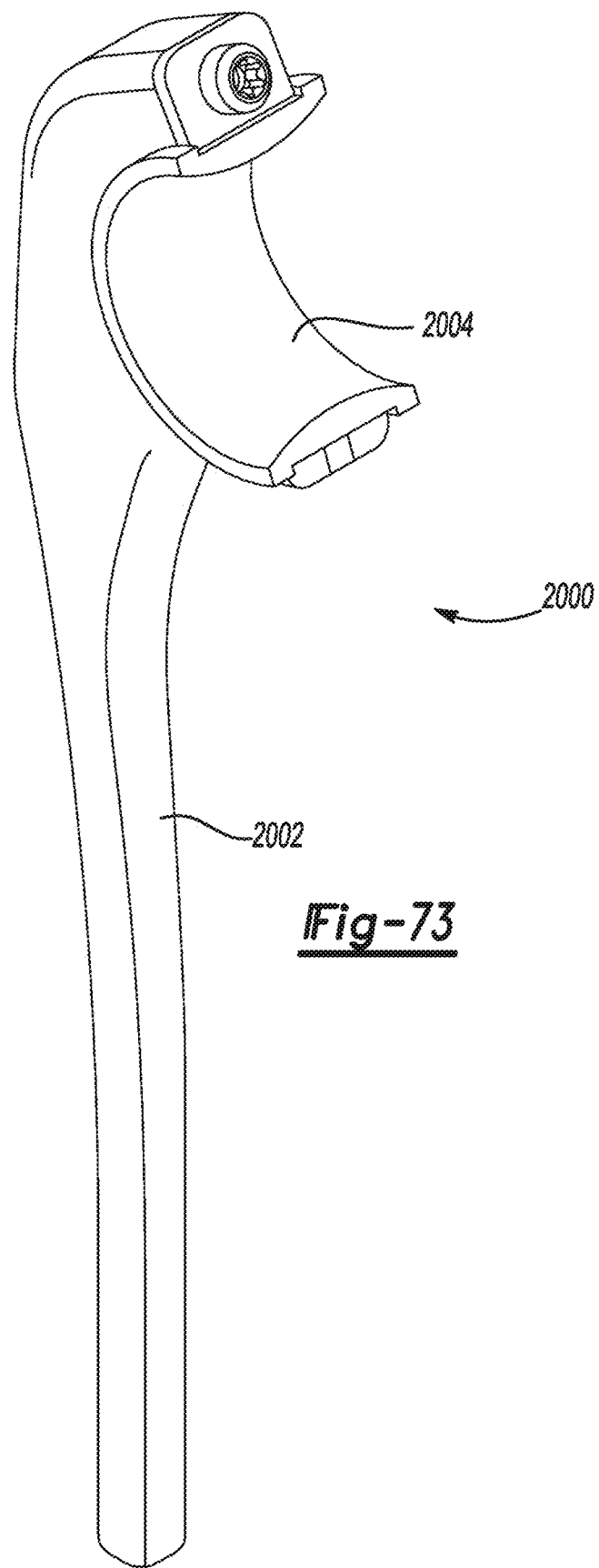
FIG. 73 is a perspective view of a modular unlinked ulnar stem assembly constructed in accordance to additional features of the present teachings.

Turning now to FIGS. 70-72, an exemplary method of attaching the articulating component 1904 to the stem 1902 will be described. At the outset, once a surgeon has selected the appropriate articulating component 1904 that satisfies a desired articulating surface geometry for a particular patient, the second end 1940 is located generally adjacent to the first end 1916 of the rails 1914 of the stem 1902 (FIG. 70). Next, the surgeon rotates the articulating component 1904 in a counter-clockwise direction about an axis 1950 (as viewed in FIGS. 70-71) such that the rails 1914 of the first retaining mechanism 1912 locate into the channel 1936 of a second retaining mechanism 1932. Continued rotation of the articulating component 1904 around the rails 1914 can additionally include slidable engagement of the convex slide surface 1948 of the articulating component 1904 along the concave slide surface 1924 of the ulnar ring 1910. The articulating component 1904 is further rotated until the catch 1942 on the articulating component 1904 engages the stop 1920 provided on the second end 1918 of the rails 1914. In this way, the catch surfaces 1944 of the articulating component 1904 can rest on the stop surfaces 1922 of the rails 1914 (FIG. 72). Next, a surgeon can advance the fastener 1908 through a passage 1954 (as best shown in FIG. 69) of the plate 1906 and threadably advance the fastener 1908 into the threaded bore 1926 of the stem 1902 to capture and retain the articulating component 1904.

With reference now to FIGS. 73-77, another exemplary modular unlinked ulnar stem assembly 2000 constructed in accordance to additional features of the present teachings will be described. The modular unlinked ulnar stem assembly 2000 can generally comprise a stem 2002, an articulating component 2004, an intermediate rail component 2006, and a fastener 2008. The drawings depict the articulating component 2004 and the intermediate rail component 2006 as separate for illustrative purposes. The articulating component 2004 and the intermediate rail component 2006 are molded together as a single piece. The stem 1902 can include an ulnar ring 2010 that is generally in the shape of a partial or semi-circular cylinder. The stem 2002 can include a first retaining mechanism 2012 that includes a groove 2014 formed in the ulnar ring 2010. A lip 2016 is provided at a terminal end of the groove 2014 on the first retaining mechanism 2012. The ulnar ring 2010 can further comprise a threaded bore 2026.

As with the configurations described above, the articulating component 2004 can be modular. In this way, a series of articulating components can be provided that each have various geometries that can be selected according to a particular patient's needs. Furthermore, while the articulating component 2004 and the rail component 2006 are shown as distinct components, they may be provided as an integrally formed piece. In one example, the rail component 2006 can be formed of biocompatible metal material such as titanium and the articulating component 2004 can be formed of UHMWPE or PEEK. As described above, in one example, the rail component 2006 can be molded to the articulating component 2004. Other techniques may be utilized to connect the rail component 2006 to the articulating component 2004.

The rail component 2006 can generally comprise a second retaining mechanism 2032 in the form of a rail 2036. The second retaining mechanism 2032 can further comprise a finger 2038 that is formed at a terminal end of the rail 2036. On an end opposite of the finger 2038, the rail component 2006 can include a plate 2040 having an eyelet 2042 formed there through. The rail component 2006 includes an annular channel 2044 that can facilitate molding with the articulating component 2004.

With specific reference now to FIG. 75, another modular unlinked ulnar stem assembly 2000' is shown. Like features are illustrated with similar reference numerals as shown and described above with respect to FIG. 74 and having a "prime" suffix. The stem assembly 2000' can include a rail component 2006' shown having a second retaining mechanism 2032' that includes a rail 2036' and a finger 2038'. An eyelet 2042' is provided on the rail component 2006'. The articulating component 2004' and the rail component 2006' are shown as separate pieces however they are molded together as a single unit.

Turning now to FIGS. 76 and 77, an exemplary method of assembling the articulating component 2004 to the ulnar ring 2010 of the stem 2002 will be described. In the examples shown in FIGS. 76 and 77, the articulating component 2004 and the rail component 2006 are shown as an integral piece. At the outset, a rail 2036 of the rail component 2006 is aligned for receipt into the groove 2014 provided on the ulnar ring 2010. Next, the articulating component 2004 and rail component 2006 are advanced into contact with the first retaining mechanism 2012 of the stem 2002. Explained further, the rail 2036 is advanced into the groove 2014 while the finger 2038 locates around the lip 2016 on the ulnar ring 2010. At this point, the fastener 2008 is advanced through the eyelet 2042 and threadably advanced into the threaded bore 2026. As can be appreciated, the first and second retaining mechanisms 2012 and 2032 cooperate to maintain the articulating component 2004 in a secure position.

With reference now to FIGS. 78 and 79, another modular unlinked ulnar stem assembly 2100 according to additional features of the present teachings will be described. The modular unlinked ulnar stem assembly 2100 can generally include a stem 2102, an articulating component 2104, and a fastener 2108. The articulating component 2104 further comprises a rail 2136. The stem 2102 can include an ulnar ring 2110 that is generally in the form of a partial cylinder and has a catch 2120 formed at an end thereof. A groove 2114 is formed in the ulnar ring 2110. In one example, the catch 2120 can cooperate with the fastener 2108 to provide a first retaining mechanism 2112. The articulating component 2104 can include a second retaining mechanism 2132 that includes a foot portion 2140 formed at an opposite end of a neck portion 2142. According to one example of assembling the articulating component 2104 to the ulnar ring 2110 of the stem 2102, the articulating component 2104 can be rotated in a counter-clockwise direction as viewed in FIG. 78 until the foot portion 2140 engages the catch 2120. Next, the fastener 2108 is threadably advanced into the threaded bore 2126 to further capture the articulating component 2104 relative to the ulnar ring 2110 of the stem 2102.

Figure 80:
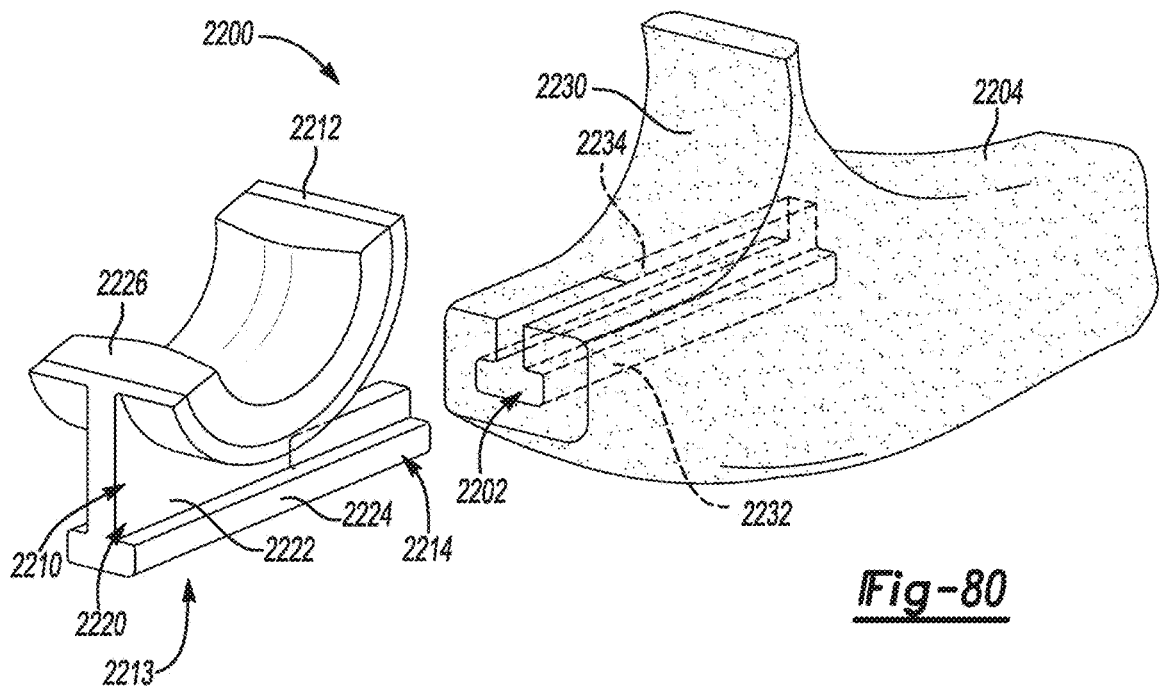
FIGS. 80 and 81 illustrate an exemplary assembly sequence of another unlinked ulnar stem assembly according to additional features.
Figure 81:
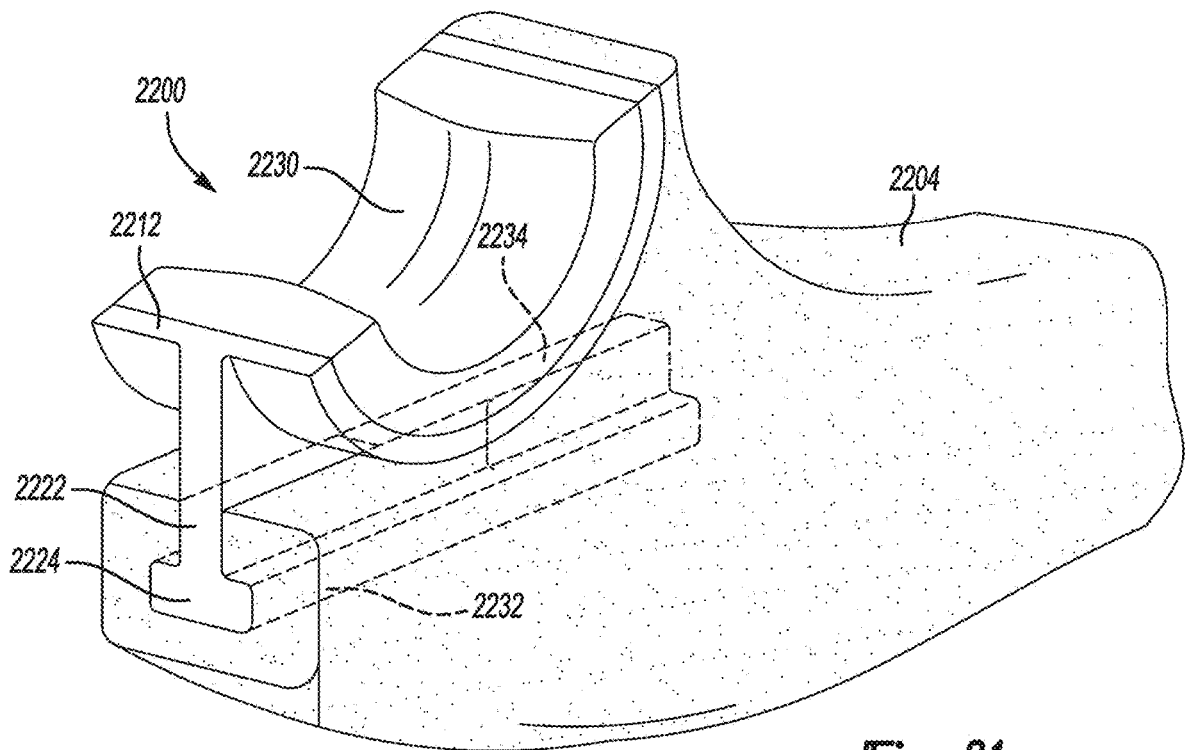

With reference now to FIGS. 80 and 81, another unlinked ulnar stem assembly 2200 according to additional features of the present teachings will be described. The unlinked ulnar stem assembly 2200 can be configured to be inserted into a prepared opening 2202 of an ulna 2204. The unlinked ulnar stem assembly 2200 generally comprises a body portion 2210 and a C-shaped support frame 2212. The body portion 2210 can be in the form of a stem structure 2213 that includes a stem portion 2214. The body portion 2210 can have a retaining mechanism 2220 formed thereon. The retaining mechanism 2220 can generally include a first portion or longitudinal member 2222 and a second portion or longitudinal member 2224. An articulating component 2226 can be connected to the C-shaped support frame 2212. In one example, the first longitudinal member 2222 can generally be in the form of an elongated planar member extending in a superior/inferior direction. The first longitudinal member 2222 can have a first medial/lateral dimension 2228. The second longitudinal member 2224 can generally be in the form of an elongated planar member that is transverse to the first longitudinal member 2222 and extends generally in the medial/lateral direction. The second longitudinal member 2224 can have a second medial/lateral dimension 2229. The second dimension 2229 is greater than the first dimension 2228.

The first and second longitudinal members 2222 and 2224, respectively, can cooperate to provide a T-shaped cross-section of the retaining mechanism 2220. In one example, the body portion 2210 can be formed of biocompatible metal material, such as titanium. The articulating component 2226 can be formed of UHMWPE or PEEK. According to one configuration, the articulating component 2226 can be molded to the C-shaped support frame 2212. Other methods may be used to interconnect the articulating component 2226 with the C-shaped support frame 2212. It is also contemplated that the articulating component 2226 can be modular relative to the C-shaped support frame 2212. In this way, in some examples, a surgeon may select an articulating component 2226 having properties suitable for a given patient's needs and intraoperatively connect the articulating component 2226 with the C-shaped support frame 2212.

With continued reference to FIGS. 80 and 81, the ulna 2204 will be described in greater detail. The ulna 2204 can be shaped to include a C-shaped receiving portion 2230 that has a geometry suitable to receive the C-shaped support frame 2212 of the unlinked ulnar stem assembly 2200. The opening 2202 can be formed, such as with a punch, reamer or other drilling device that is operable to form a cavity having a shape that is complementary with the retaining mechanism 2220. In this way, the opening 2202 generally has a first longitudinal cavity portion 2232 and a second longitudinal cavity portion 2234 that collectively provides an elongated T-shaped cavity for receiving the stem structure 2212 and retaining mechanism 2220 of the unlinked ulnar stem assembly 2200 as shown in FIG. 81. In one example, bone cement may be used in the opening 2202. Additionally, or alternatively, the outer surface of the retaining mechanism 2220 can be porous for facilitating boney ingrowth.

As best illustrated in FIG. 81, the second longitudinal member 2224 can be confined within the first longitudinal cavity portion 2232 to inhibit movement of the unlinked stem assembly 2200 in an anterior direction when implanted into the ulna 2204. The unlinked stem assembly 2200 is also inhibited from movement in other directions, such as the medial and lateral directions upon receipt into the opening 2202. It is appreciated that the T-shaped cross-section of the retaining mechanism 2220 and the corresponding opening 2202 may be formed differently. Other cross-sections are contemplated, such as a dove-tail cross-section, a curved cross-section or other cross-sections suitable to provide a secure relationship between the retaining mechanism 2220 and the opening 2202.

With reference now to FIGS. 82 and 83, another unlinked ulnar stem assembly 2250 according to additional features of the present teachings will be described. The unlinked ulnar stem assembly 2250 can be configured to be inserted into a prepared opening 2252 of an ulna 2204. The unlinked ulnar stem assembly 2250 generally comprises a body portion 2260 and a C-shaped support frame 2262. The body portion 2260 can be in the form of a stem structure 2263 that includes a stem portion 2264. The body portion 2260 can have a retaining mechanism 2270 formed thereon. The retaining mechanism 2270 can generally include a first portion or longitudinal member 2272 and a second portion or longitudinal member 2274. The second longitudinal member 2274 can generally be in the form of a cylinder 2275. An articulating component 2276 can be connected to the C-shaped support frame 2262. In one example, the first longitudinal member 2272 can generally be in the form of an elongated planar member extending in a superior/inferior direction. The first longitudinal member 2272 can have a first medial/lateral dimension 2277. The cylinder 2275 of the second longitudinal member 2274 can have portions that extend in a direction that is transverse to the first longitudinal member 2272. The second longitudinal member 2274 can have a second medial/lateral dimension 2278. The second dimension 2278 is greater than the first dimension 2277. The retaining mechanism 2270 can therefore provide a substantially non-linear cross-section.

In one example, the body portion 2260 can be formed of biocompatible metal material, such as titanium. The articulating component 2276 can be formed of UHMWPE or PEEK. According to one configuration, the articulating component 2276 can be molded to the C-shaped support frame 2262. Other methods may be used to interconnect the articulating component 2276 with the C-shaped support frame 2262. It is also contemplated that the articulating component 2276 can be modular relative to the C-shaped support frame 2272. In this way, in some examples, a surgeon may select an articulating component 2276 having properties suitable for a given patient's needs and intraoperatively connect the articulating component 2276 with the C-shaped support frame 2262.

With continued reference to FIGS. 82 and 83, the ulna 2254 will be described in greater detail. The ulna 2254 can be shaped to include a C-shaped receiving portion 2280 that has a geometry suitable to receive the C-shaped support frame 2262 of the unlinked ulnar stem assembly 2250. The opening 2252 can be formed, such as with a punch, reamer, or other drilling device that is operable to form a cavity having a shape that is complementary with the retaining mechanism 2270. In this way, the opening 2252 generally has a first longitudinal cavity portion 2282 having a cylindrical cross-section, and a second longitudinal cavity portion 2284 having a generally planar cross-section that collectively provide a shape that is suitable for receiving the stem structure 2263 and retaining mechanism 2270 of the unlinked ulnar stem assembly 2250 as shown in FIG. 82. Once the retaining mechanism 2270 is suitably inserted into the opening 2252, a bone screw 2240 is inserted into a throughbore 2242 provided in the cylinder 2275. The bone screw 2240 is then threadably advanced into the ulna 2254 until a head 2244 of the bone screw 2240 rests on a counterbore ledge 2246 formed in the cylinder 2275.

In one example, bone cement may be used in the opening 2252. Additionally, or alternatively, the outer surface of the retaining mechanism 2270 can be porous for facilitating bony ingrowth. As best illustrated in FIG. 83, the second longitudinal member 2274 can be confined within the first longitudinal cavity portion 2282 to inhibit movement of the unlinked ulnar stem assembly 2250 in an anterior direction when implanted into the ulna 2254. The unlinked ulnar stem assembly 2250 is also inhibited from movement in other directions, such as the medial and lateral directions upon receipt into the opening 2252. It is appreciated that the cylindrical shaped cross-section of the second longitudinal member 2274 of the retaining mechanism 2270 and the corresponding opening 2254 may be formed differently.

Figure 84:
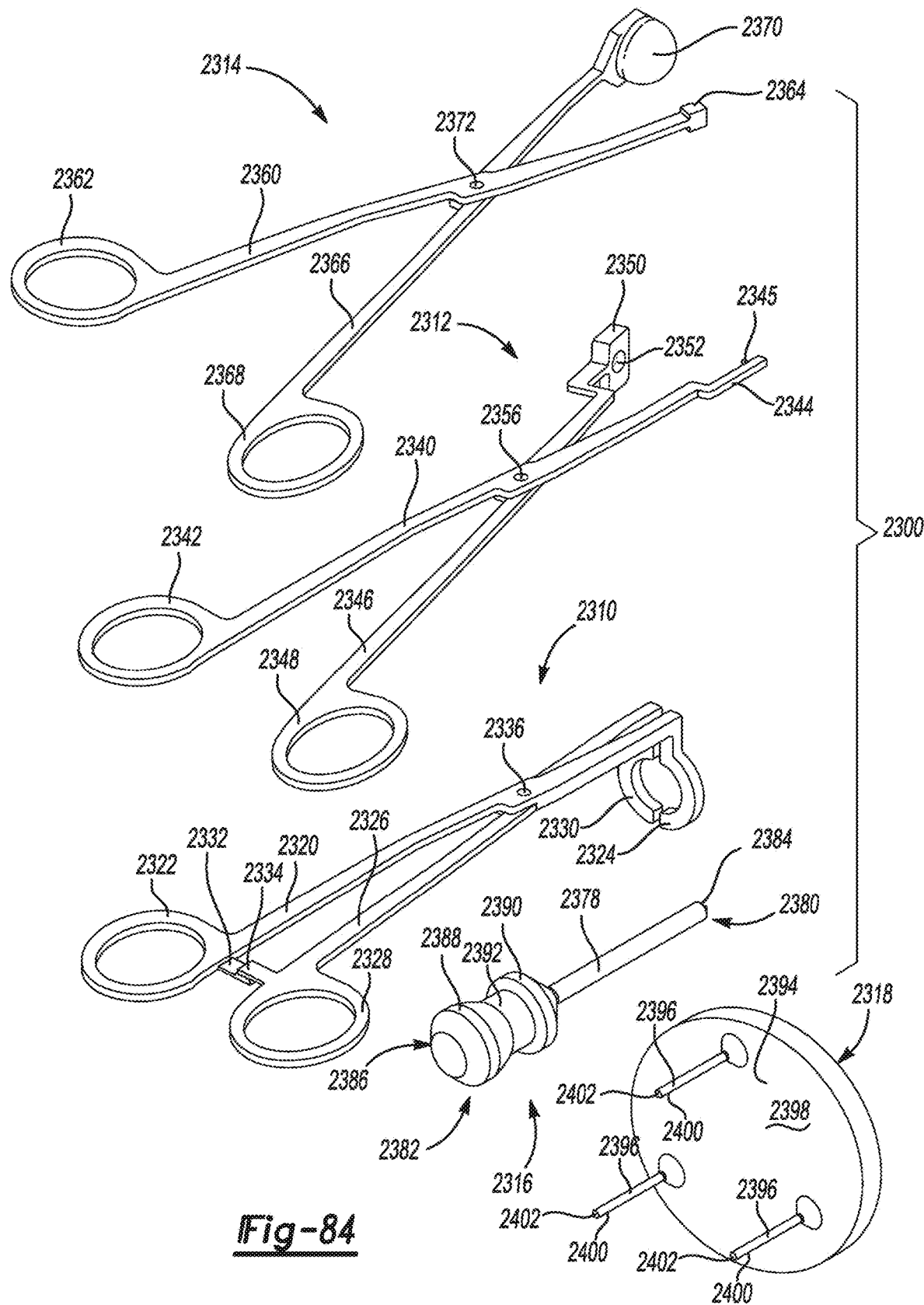
FIG. 84 is a perspective view of an exemplary bearing removal tool kit constructed in accordance to one example of the present teachings.
Figure 85:
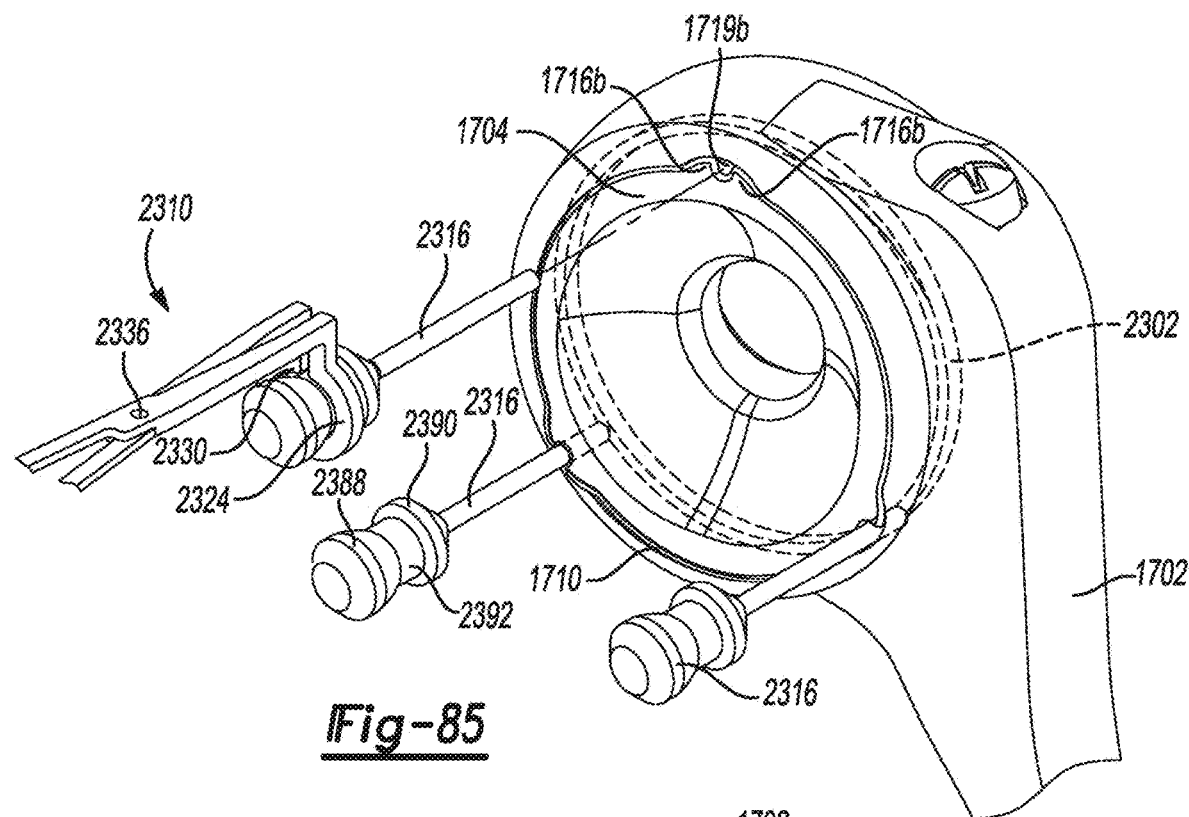
FIG. 85 is a medial perspective view of an exemplary ulna stem component and bearing member shown with a first tool of the bearing removal tool kit slidably inserting extractor pins according to one example.

With reference now to FIGS. 84 and 85, a bearing removal tool kit 2300 constructed in accordance to additional features of the present teachings will be described. In general, the bearing removal tool kit 2300 can include a series of tools that, in various combinations, can be used to assist a surgeon in compressing a lock ring 2302 (FIG. 85) such that a bearing member 1704 can be subsequently urged (in the medial/lateral direction) out of an annular cage 1710 of an ulna stem component 1702. As will be described, while the bearing removal tool kit 2300 is shown cooperating with the lock ring 2302 and ulna stem component 1702, the various tools of the bearing removal tool kit 2300 can be used to compress lock rings having different configurations, such as shown herein at reference numeral 1706 (FIG. 54) or at reference numeral 1624 (FIG. 51). Likewise, while the bearing removal tool kit 2300 is shown for use during removal of the bearing member 1704, the bearing removal tool kit 2300 can be used to urge other bearing members having various shapes, such as disclosed herein including the bearing member 1610 (FIG. 51).

The bearing removal tool kit 2300 can generally comprise a first tool 2310, a second tool 2312, a third tool 2314, a series of extractor pins 2316 and an extractor plate 2318. The first tool 2310 can generally take the shape of forceps and, as will be described, can be used to hold and position the extractor pins 2316 relative to the ulna stem component 1702 and the bearing member 1704. The first tool 2310 can include a first arm 2320 having a first handle 2322 at one end and a half ring 2324 on an opposite end. A second arm 2326 can have a second handle 2328 at one end and a half ring 2330 at an opposite end. A pair of locking members 2332 and 2334 can be formed on the first handle 2322 and the second handle 2328, respectively. The first and second arms 2320 and 2326 can be pivotally coupled at a pivot 2336. The opposed half rings 2324, 2330 have opposed arcuate surfaces that engage a cylindrical neck 2392 of the pins 2316 as will be described.

The second tool 2312 can be used to further urge the extractor pins 2316 between the annular cage 1710 of the ulna stem component 1702 and the bearing member 1704 as shown in FIGS. 87 and 88. The second tool 2312 can also be generally in the form of forceps. The second tool 2312 can have a first arm 2340 having a first handle 2342 at one end and an elongated locating finger 2344 at an opposite end. The locating finger 2344 can include a nub 2345 provided thereon. The second tool 2312 can further include a second arm 2346 having a second handle 2348 at one end and a rectangular locating pad 2350 at an opposite end. The locating pad 2350 can define a recess 2352. The first and second arms 2340 and 2346 can be pivotally coupled at a pivot 2356.

The third tool 2314 can be used to urge the bearing member 1704 out of the annular cage 1710 once the lock ring 2302 has been compressed as shown in FIGS. 91 and 92. The third tool 2314 can also take the general shape of forceps. The third tool 2314 can include a first arm 2360 having a first handle 2362 at one end and a rectangular locating pad 2364 at an opposite end. The third tool 2314 can also have a second arm 2366 having a second handle 2368 at one end and a spherical plunger 2370 at an opposite end. The first and second arms 2360 and 2366 can be pivotally coupled at a pivot 2372.

The extractor pin 2316 can be used to slidably advance between the annular cage 1710 of the ulna stem component 1702 and the bearing member 1704. During such slidable advancement, the extractor pin 2316 can ramp over an outer radial surface of the lock ring 2302 to compress the lock ring 2302 as will be further described. The extractor pin 2316 generally includes a shaft 2378 that has a first end 2380 and a second end 2382. The first end 2380 can have an interference portion 2384 in the general shape of a conical tip. The second end 2382 can include a head 2386 that includes a first collar 2388, a second collar 2390 and a cylindrical neck 2392 therebetween.

The extractor plate 2318 can be used similarly to the extractor pins 2316 when it is desired to concurrently or simultaneously advance a series of extractor pins between the annular cage 1710 of the ulna stem component 1702 and the bearing member 1704 instead of sequentially locating individual extractor pins 2316. In general, the extractor plate 2318 includes a plate body 2394 having a plurality of extractor pins 2396 extending from a first surface 2398 of the plate body 2394. Each of the extractor pins 2396 includes first ends 2400 having interference portions 2402.

Figure 86:
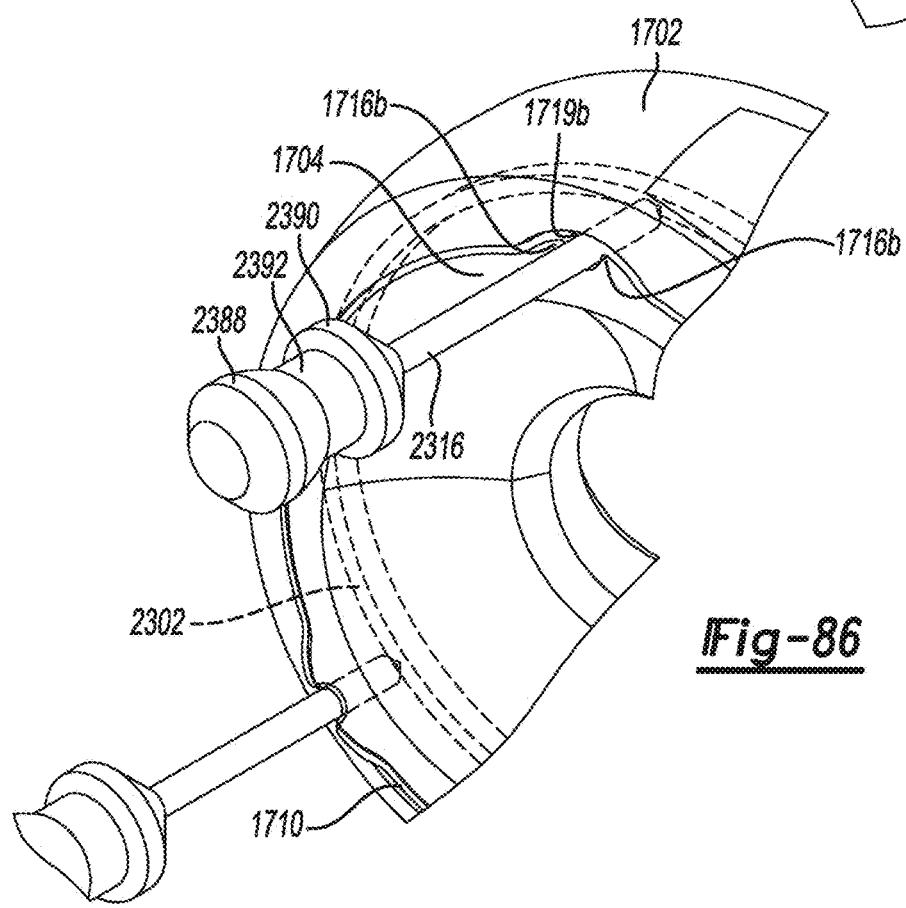
FIG. 86 is a detailed perspective view of a pair of extractor pins after being located into respective depressions of the bearing member by the first tool.

With reference now to FIGS. 85 and 86, initial positioning of the extractor pins 2316 with the first tool 2310 will be described according to one example. Again, it will be appreciated that while the first tool 2310 is being described as initially locating the extractor pins 2316, the extractor pins 2316 may be initially located with other tools or simply by a surgeon's fingers. At the outset, the half rings 2324 and 2330 of the first tool 2310 can be located around the neck 2392 at the second end 2382 of the extractor pin 2316. Next, the first end 2380 of the extractor pin 2316 can be advanced into the depression 1719*b* between the tabs 1716*b* of the bearing member 1704. According to one example, the extractor pin 2316 can be advanced in the medial/lateral direction a distance until initially engaging the lock ring 2302. While the second tool 2312 is described herein as further advancing the extractor pin to compress the lock ring 2302, it is contemplated that in some examples, the first tool 2310 can optionally be used to further advance the extractor pins 2316 to compress the lock ring.

With reference now to FIGS. 87 and 88, the second tool 2312 of the bearing removal tool kit 2300 will be described as further advancing the extractor pins 2316 between the annular cage 1710 of the ulna stem component 1702 and the bearing member 1704 to compress the lock ring 2302. Initially, the recess 2352 of the locating pad 2350 can be placed around the first collar 2388 of the second end 2382 of the extractor pin 2316. The nub 2345 of the locating finger 2344 can also be located at the depression 1719*b*. The first end second handles 2342 and 2348 can then be urged together, such that the first and second arms 2340 and 2346 rotate or pivot around the pivot 2356 to create a clamping force between the locating finger 2344 and the locating pad 2350. The clamping force causes the interference portion 2384 of the extractor pin 2316 to ramp across a radial outer surface 2410 of the lock ring 2302 and thereby compress the lock ring 2302 into the groove 1724 of the bearing member 1704. Once all of the extractor pins 2316 have been advanced, the lock ring 2302 will be compressed into the groove 1724 and therefore moved to a position out of the groove 1738 of the ulna stem component 1702. According to other methods, one extractor pin 2316 can be slidably advanced in the medial (or lateral) direction through the depression 1719*b* to the position shown in FIG. 88. Next, another longitudinal member (i.e., a pin, nail, shaft, etc.) can be slidably advanced in the opposite direction through the same depression 1719b to push out and take the place of the extractor pin 2316. In such a method, only one extractor pin 2316 is needed as it can be used in sequence through all of the depressions 1719a, 1719b and 1719c. It is also appreciated that while three depressions 1719a, 1719b and 1719c have been described as receiving three extractor pins 2316, using more or less extractor pins and depressions are contemplated.

Figure 90:
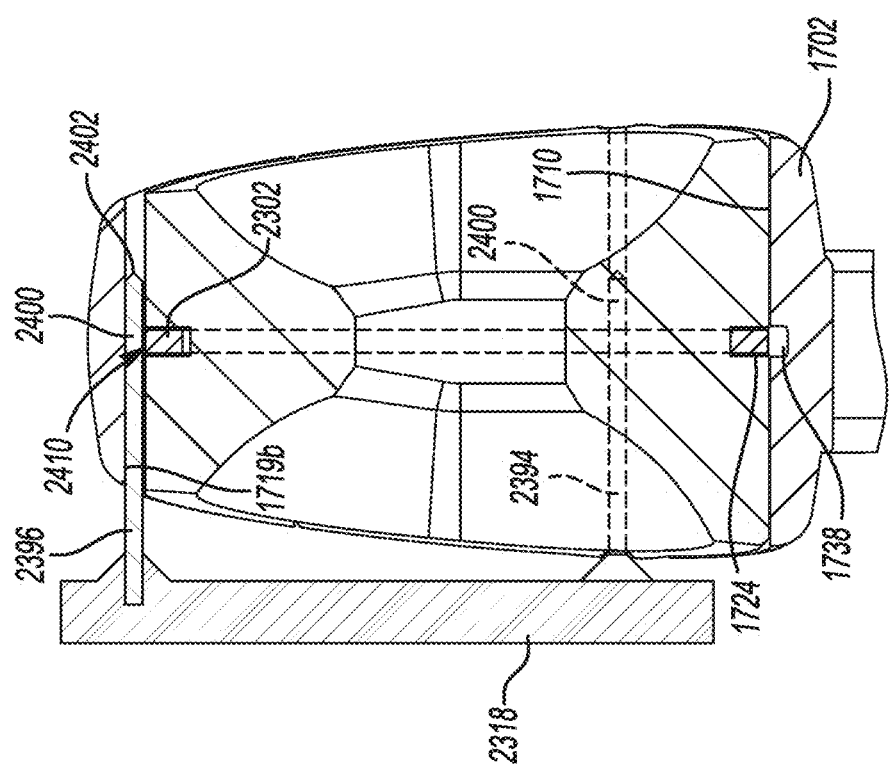
FIGS. 89 and 90 are an exemplary sequence illustrating an extractor plate used to concurrently advance a plurality of extractor pins across the lock ring to compress the lock ring into the groove of the ulna bearing according to additional features.
Figure 89:
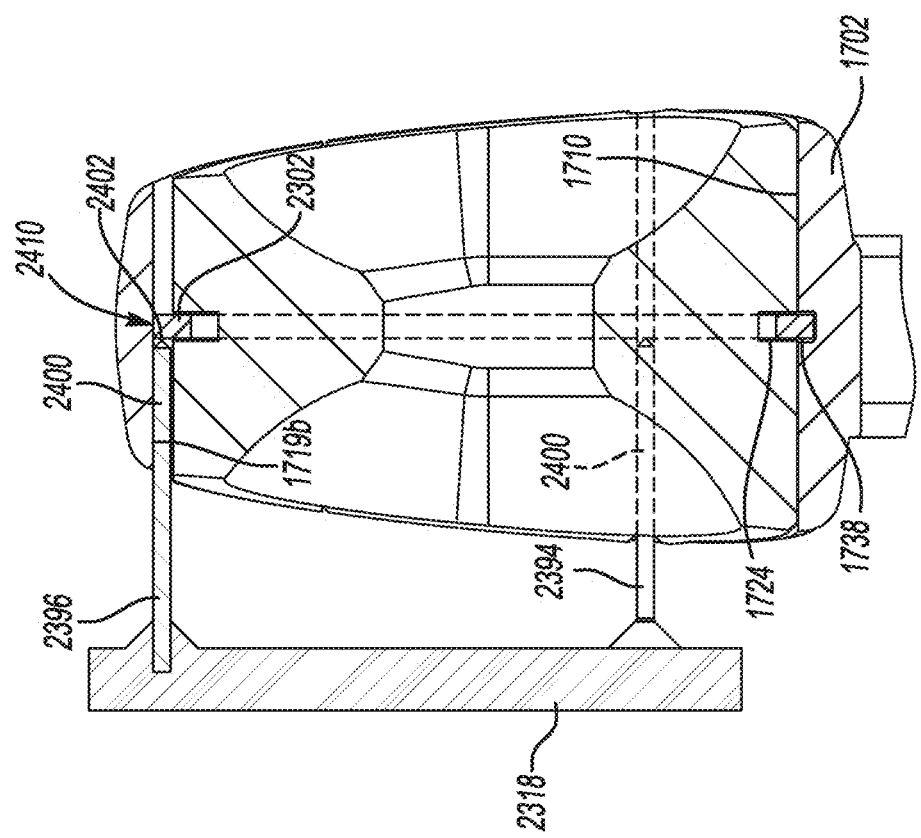

With reference now to FIGS. 89 and 90, an alternate method of compressing the lock ring 2302 using the extractor plate 2318 will be described. Again, the extractor plate 2318 can be used when it is desired to concurrently or simultaneously pass a series of pins between the annular cage 1710 of the ulna stem component 1702 and the bearing member 1704. When using the extractor plate 2318, a surgeon can initially position the respective first ends 2400 of the extractor pins 2396 into the corresponding depressions 1719a, 1719b and 1719c of the bearing member 1704. Next, the plate body 2394 of the extractor plate 2318 can be advanced further between the annular cage 1710 of the ulna stem component 1702 and the bearing member 1704. In doing so, the respective interference portions 2402 slidably advance along the outer surface 2410 of the lock ring 2302 causing it to compress into the groove 1724 of the bearing member 1704. By compressing the lock ring 2302 into the groove 1724 of the bearing member 1704, the lock ring 2302 is moved to a position away from the groove 1738 in the ulna stem component 1702. The extractor plate 2318 can be advanced in the medial/lateral direction by any suitable clamping instrument, such as those disclosed herein or by urging with a surgeon's fingers.

With reference now to FIGS. 91 and 92, use of the third tool 2314 to urge the bearing member 1704 out of the annular cage 1710 after the lock ring 2302 has been compressed will be described. In one example, the locating pad 2364 of the first arm 2360 can be located on one side of the ulna stem component 1702 and the plunger 2370 can be located on the opposite side of the ulna stem component 1702 and centrally aligned and nested into the bearing member 1704. In one example, a nub similar to the nub 2345 (FIG. 87) can be included on the locating pad 2364 for locating into the depression 1719b (FIG. 86). The plunger 2370 can be formed entirely or partially of resilient material. The plunger 2370 can include a metallic substrate having a nylon coating or be formed entirely of a metallic substrate. In other examples, a polymeric material can be provided on the plunger 2370. Next, the first and second handles 2362 and 2368 (see FIG. 84) can be urged together, such that the first and second arms 2360 and 2366 pivot around the pivot 2372 and create a clamping force between the locating pad 2364 and the plunger 2370. As a result, the plunger 2370 forcibly advances the bearing member 1704 in the medial/lateral direction out of the annular cage 1710 as shown in FIG. 92. Once the bearing member 1704 is urged out of the annular cage 1710, the extractor pins 2316 will simply fall away from the annular cage 1710 and can be later collected.

While the description in the specification and illustrated in the drawings are directed to various embodiments, it will be understood that various changes may be made and equivalents may be substituted for elements thereof without departing from the scope of the teachings and the appended claims. In addition, many modifications may be made to adapt a particular situation or material to the teachings without departing from the scope thereof. Therefore, it is intended that the teachings and claims are not be limited to any particular embodiment illustrated in the drawings and described in the specification, but that the teachings and claims can include any embodiments falling within the foregoing description and the appended claims.

What is claimed:

1. A joint prosthesis device, comprising:
   a first stem structure comprising a first end configured to be implanted into a first bone of a patient and an opposite second end terminating in a pair of furcations; and
   a first bearing component removably coupled to the second end of the first stem structure, the first bearing component comprising:
      a first condyle portion that is removably attached to a first of the pair of furcations, the first condyle portion being at least partially spherically shaped and including a first pin aperture,
      a second condyle portion that is removably attached to a second of the pair of furcations and separate from the first condyle portion, the second condyle portion being at least partially spherically shaped and including a second pin aperture, and
      a pin extending between the first condyle portion and the second condyle portion, a first end of the pin inserted into the first pin aperture and a second end of the pin inserted into the second pin aperture.

2. The device of claim 1, wherein:
   the first condyle portion comprises a first slotted aperture that slidingly engages the first of the pair of furcations; and
   the second condyle portion comprises a second slotted aperture that slidingly engages the second of the pair of furcations.

3. The device of claim 2, wherein:
   the first condyle portion comprises a first mounting aperture;
   the first of the pair of the furcations comprises a first threaded fastener aperture;
   the second condyle portion comprises a second mounting aperture;
   the second of the pair of the furcations comprises a second threaded fastener aperture;
   a first fastener is inserted through the first mounting aperture and into the first threaded fastener aperture to secure the first condyle portion to the first of the pair of furcations; and
   a second fastener is inserted through the second mounting aperture and into the second threaded fastener aperture to secure the second condyle portion to the second of the pair of furcations.

4. The device of claim 3, wherein the first fastener is configured to prevent the first condyle portion from rotating relative to the first of the pair of furcations, and the second fastener is configured to prevent the second condyle portion from rotating relative to the second of the pair of furcations.

5. The device of claim 3, wherein the first fastener extends along a first axis, the second fastener extends along a second axis, and the first axis and the second axis are substantially parallel.

6. The device of claim 5, wherein the pin extends along a pin axis, and the pin axis is substantially perpendicular to the first axis and the second axis.

7. The device of claim 1, wherein the first end of the first stem structure is configured to be implanted into a medullary canal of a humerus.

8. The device of claim 1, wherein a partially spherically shaped portion of the first condyle portion faces a partially spherically shaped portion of the second condyle portion.

9. The device of claim 8, wherein the first pin aperture is positioned at an apex of the partially spherically shaped portion of the first condyle portion, and the second pin aperture is positioned at an apex of the partially spherically shaped portion of the second condyle portion.

10. The device of claim 1, wherein the first end of the pin is fixedly attached to the first pin aperture and the second end of the pin is slidingly inserted into the second pin aperture.

11. The device of claim 1, wherein the first end of the pin is slidingly inserted into the first pin aperture and the second end of the pin is fixedly attached to the second pin aperture.

12. The device of claim 1, wherein the first end of the pin is slidingly inserted into the first pin aperture and the second end of the pin is slidingly inserted into the second pin aperture.

13. The device of claim 1, wherein the pin comprises a cobalt chromium alloy.

14. The device of claim 1, further comprising a second stem structure comprising:

a first end that is configured to fit within a second bone of the patient; and a second bearing component positioned on a second end of the second stem structure, the second bearing component comprising a first bearing face, a second bearing face, and a through hole extending therebetween.

15. The device of claim 14, wherein the first bearing face is positioned to face away from the second bearing face.

16. The device of claim 15, wherein the first bearing face articulates with the first condyle portion and the second bearing face articulates with the second condyle portion.

17. The device of claim 16, wherein the pin extends through the through hole.

18. The device of claim 17, wherein the second end of the second stem structure is configured to be implanted into a medullary canal of an ulna.

* * * * *